US010109027B1

(12) United States Patent
Stack

(10) Patent No.: US 10,109,027 B1
(45) Date of Patent: Oct. 23, 2018

(54) DATABASE ACCESS AND COMMUNITY ELECTRONIC MEDICAL RECORDS SYSTEM

(71) Applicant: Brian T. Stack, Carlisle, AR (US)

(72) Inventor: Brian T. Stack, Carlisle, AR (US)

( * ) Notice: Subject to any disclaimer, the term of this patent is extended or adjusted under 35 U.S.C. 154(b) by 0 days.

(21) Appl. No.: 14/147,441

(22) Filed: Jan. 3, 2014

Related U.S. Application Data

(63) Continuation-in-part of application No. 13/199,552, filed on Sep. 1, 2011, now abandoned.

(60) Provisional application No. 61/402,579, filed on Sep. 1, 2010.

(51) Int. Cl.
*G06Q 50/00* (2012.01)
*G06Q 50/24* (2012.01)
*G06Q 10/10* (2012.01)

(52) U.S. Cl.
CPC ............ *G06Q 50/24* (2013.01); *G06Q 10/10* (2013.01); *G06Q 50/00* (2013.01)

(58) Field of Classification Search
CPC ... G06F 19/3456; G06F 19/325; G06Q 50/22; G06Q 10/06316
USPC .......................................................... 705/2–3
See application file for complete search history.

(56) References Cited

U.S. PATENT DOCUMENTS

| | | | | |
|---|---|---|---|---|
| 2003/0036683 A1* | 2/2003 | Kehr | G06F 19/325 | 600/300 |
| 2005/0145257 A1* | 7/2005 | Barrera | G06Q 10/06316 | 128/898 |
| 2009/0076857 A1* | 3/2009 | Eletreby | G06Q 50/00 | 705/3 |

* cited by examiner

*Primary Examiner* — Joy Chng
(74) *Attorney, Agent, or Firm* — Schrantz Law Firm, PLLC; Stephen D. Schrantz

(57) ABSTRACT

A community electronic medical record provides access to a patient's records. A unity server of the present invention allows a user to enter a query requesting the information that a medical provider needs such as past history, allergies, billing information, and other medical data that may be related to the patient. The unity server queries at least one database, preferably many, to access the patient's records relevant to the provider's query. The unity server retrieves information from multiple sources to provide increased information for treatment of the patient.

20 Claims, 41 Drawing Sheets

DATABASE ACCESS AND COMMUNITY ELECTRONIC MEDICAL RECORDS SYSTEM

CROSS-REFERENCE TO RELATED APPLICATIONS

This application claims priority to and is a continuation in part of U.S. application Ser. No. 13/199,552 filed on Sep. 1, 2011 which is a continuation in part of U.S. Application Ser. No. 61/402,579 filed on Sep. 1, 2010.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND OF THE INVENTION

I. Field of the Invention

The present invention relates to an electronic medical records system that provides access to a patient's records. The present invention provides a more consistent record system making additional information available to other healthcare providers to improve the care of the patient.

II. Description of the Known Art

Patents and patent applications disclosing information relevant to computers are disclosed below (U.S. Pat. Nos. 5,815,717 and 6,864,779). These patents and patent applications are hereby expressly incorporated by reference in their entirety.

Therefore, the present invention is needed to improve access to a patient's records. The present invention is also needed to improve diagnosis and treatment of a patient by providing a medical care provider with relevant information from multiple different sources. The present invention is also needed to provide a consistent method of accessing database records.

SUMMARY OF THE INVENTION

The Unity server is a virtual environment that consists of real database of similar or disparate design. The form, function, structure, organization, content and actual database manager are no longer relevant to gaining access to information. The system creates an amorphous data environment by unifying applications and databases. Data access from a database is normally accomplished by knowing where and how the data is stored.

The Unity server accesses data based on context. In effect, data is accessed, updated or inserted based on why the data is needed. A set of context translators are employed to translate between how data is to be accessed and why it is to be accessed. Programs can gain access to information without knowing where or how the data is stored, only why the data is needed. In addition, the source of data as well as structure, competence or other "fixed" characteristics, can change without crippling the software or causing cascading failures across an enterprise of disparate databases.

All of the disparate databases become unified into a single data environment. Application software can be integrated without any interfaces and in many cases, without adding any software to the target system. Application software needs only know why the data is needed. The system will automatically translate to the location, connection and form in which that data is stored. Each application and its database live in a "system space". System spaces do not have an interface and do not require application awareness.

It is also possible for the unified system to "heal" itself when there are failures or unpublished changes in one of the unified system's design. Alternate databases and applications can be utilized to access data if one of the unified systems goes off-line. In fact, automatic rerouting is accomplished without the system ever encountering an error and without delay. Applications do not need a database connection and can be isolated from the network in general. Likewise databases need not be exposed to the network or other opportunities for access to be compromised.

Complete access to information can be accomplished with only two programmatic Objects. 1) NetObject and 2) Client. An example in program code is:

```
client=new Client( );
netObject=new NetObject(<internal context>, <directive>);
netObject=client.communicate(netObject);
```

In the above example, data can exist in databases at any location over the network or locally. Alterations to an implemented database will not cause the application to fail or require any programmatic changes. The translation can be adjusted to match or the system can interpolate the most likely correction. Data transportation via a NetObject has no metadata or any specifications about a database. The context is translated into database references at the last step before handing the data (or request) to any given database server. The detailed steps on the process are discussed later in this document.

Regarding the virtual logic, the system acts like an amorphous logic engine that can be implemented on any machine in a network (including direct access as a client). The Virtual Logic Server is actually a melding of two technological approaches to application generation: 1) Object interpreter 2) Useorder interpreter. Object Interpreter, the first melded technology, is an interpreter that is driven by flat records in which each of the records contains a fixed number of fields. Each visible object to be installed on the pasteboard is represented by one of these records with a fixed number of fields. These visible objects are instances of a given widget, when taken together represent a collection. The collection does not exist in the same sense as a program/class file or as a single data record. It only exists by virtue of a populated set of widgets which have been assigned to the same collection.

Database Unification (Amorphous Data Environment)

Combine the databases of disparate applications into a single, unified data store accessible as if all of the attached databases were designed and implemented identically.

Data can be used and managed without respect to the actual database design. Applications can be "database unaware" freeing the application to conform to the user's need.

Background

Application vendors regularly change their software and database designs as a normal part of evolving their products. References to data can therefore become broken when sharing data across multiple systems. Traditionally, unexpected changes cause SQL errors which halt processing causing loss of data for updates and causing data to be unavailable for queries. Such broken references can also include failure to access other tables which would have been accessed after the failed table.

For example, in the medical industry, a plethora of tables are used for different aspects of a given patient. Failure in one table can hide valuable medical information stored in other tables.

Traditional solutions rely on reference tables in which the differences in the databases are defined. Changes discovered in a referenced database requires changes to the definitions, frequently after a failure has been detected, leaving data access unavailable until the problem is addressed by a technician.

Solution (Context-Based)

Direct to database connections can survive and continue to function after unexpected changes to the target databases. Context-based access allows applications from multiple vendors to function as a single system without the coordination of the respective vendors.

Application software can now operate unaware of the data structure or where the data is stored. The application need only understand the context in which it needs the data.

Data can be automatically re-routed to or from alternate databases when a given database is unavailable providing reliability in a federated model. Data can be centrally collected as a by-product of processing allowing an amalgamated model to remain current without batch updates. Both models can be mixed as needed.

Virtual Logic (Amorphous Logic Environment)

Background

Flexibility of implementation of complex logic or other aspect of system design is traditionally handled by program code generators, run-time interpreters or programmed-in options. For example, C.A.S.E tools, $4^{th}$ and $5^{th}$ generation languages or form generators.

Many of the tools provide great flexibility of design and implementation but leave a rigid user environment. In all cases the technologies force a trade-off between ease of implementation and resultant system capabilities. Systemic form and structure are normally dictated by the tool. For example, code generators are limited to generating those things for which they are intended and forms are limited to the confines of the form and available formats.

The current acceptable way to extend the tools capabilities beyond their own limitations frequently involves support for hand-written specialty code.

Solution (Amorphous Logic Environment)

Synthesizer creates an environment within which is conducive to the assembly of atomic elements of a needed process. Similar to programming languages boiling down to a small set of words, functionality also boils down to a static set of atomic functions.

The environment uses the actual problem to be solved as the framework to synthesize the solution. In effect, the needed process is described by the problem it solves. Atomic components assemble themselves into a process or other computer function from very high level specifications. For example, a GUI layout would require little more than the screen appearance, field references and rules. A process would require little more than the field relationships and rules.

The resultant process is scaffolded by a "soft-bus" which acts as both the glue and communication vehicle. The process, screen, output or other runs and then dissipates (although they could be saved).

The resultant system can then flex interactively as the user's needs change or expand. The synthesizing processes could easily be driven by proactive computer intelligence built into a user interface.

Chain-Based Architecture

Executing a model of an enterprise as the application automates the flow of information explicitly and does so dynamically. Data access becomes fluid and is automatically tailored to each situation and successive user as the need is encountered.

Background

Application software is constructed where each needed elemental function is represented in a set of program code built as routines/methods and classes/programs. The overall system design is only implied by the juxtaposition of all of the programs of that system. While the system architecture may have been explicitly designed, actual processing thus becomes a matter of one program creating output for the next in a coincidental chain of processes.

System enhancement becomes more and more restricted as more and more programs become interdependent. However, the programs are frequently unaware of other programs on which they rely or other programs for which they support.

Improvements or expanding capability frequently break the system in unexpected ways usually down-stream from the changes. Application software becomes more static as changes become more difficult and more expensive. The result of which can limit the usable life-span of the software or simply hit a point of diminishing returns idling future development efforts.

In addition, traditional systems tend to be reliant on a static database model and divided into input, process and output.

The database is usually a mirror of the application where multiple programs independently rely on rigidly defined shared tables. Changes to tables can therefore cause problems in other parts of the system adding an additional dimension where cost can accelerate faster than the benefits of improvements or changes.

Additionally, system design is hamstrung by cost where each step of traditional development becomes a tradeoff between functionality and cost/development time. There is a stark disconnect between system design and actual use caused by time and perspective.

Solution

Chain processor interprets a complete enterprise model dynamically creating an explicit processing environment replacing the coincidental arrangement of programs and processes. Elemental functions become more implied as does input and output. The effect of which is that the need for rigid screen design is virtually eliminated as the data becomes fluid.

The data seems to follow the user since the data is moving in accordance with chained events and tasks. Data converges where needed allowing the user to gain access to only the needed data in a single location. Application navigation is virtually eliminated since the convergence determines the presentation.

Significantly more of the solution can become automated allowing directed design to supplant traditional output ranging and sorting. The flow of information, processes, workflows and work steps can be automated at a fine level of granularity bringing processes normally left manual on-line. System architecture becomes a simple matter of modeling the work flow and processes in and between departments and enterprises. In fact, the model can extend across multiple enterprises an entire community or industry.

A by-product of this approach is added data security. User access credentials can be relegated to only accessing the system and not the data. Chain transactions can represent authority to gain access to a specific set of data limited topically. For example a single patient record which can include data from any of the connected systems.

Chain-Based Reasoning

Fluid presentation of data can be altered and reconstituted dynamically to follow and support the specific user's reasoning activities. The same display real estate is re-used dynamically in succession to support successive tasks and answer successive questions.

Background

Traditionally systems rely on formatted screens and reports as a way to present specific and related data. The capabilities of reporting/inquiry are then extended through user specified run-time sorts, ranges and potentially column options.

Users can therefore be forced to collect data or answer questions by navigating through different screens and reports. Users then have a tendency to observe the values on each screen or report in a constant order when performing the same task or answering the same question. The same is true for the user's movements between screens and reports, particularly in systems where there is a preponderance of data supporting a single instance. For example, in medical systems tens or perhaps hundreds of tables can be the source if data for a single patient. In hospitals, nurses normally log onto 6 different systems to support a single patient.

Solution

Reasoning support dynamically moves the appropriate data formatted and ordered as needed into a given location per the user's needs and dictates. While chain-based architecture dynamically moves data and controls between users, systems and enterprises, chain-based reasoning amorphously adjusts the system to meet successive needs of the same user.

The organization of any data being managed by the system can be topically displayed, organized and sorted dynamically. Changes can be interactive allowing the user ad-hoc access to any data that the user is privileged to view or be presented in pre-defined ways.

Users "teach" the system how to answer specific questions or support work-steps using the same interface as the ad-hoc interaction. Data is then presented as needed where the different organization and presentation change successively with a user action or an amount of time.

It is also possible for the system to interview the user based on known templates to develop the reasoning chain steps.

Topic interpretation (note: this is the current vehicle for implementing a GUI driven by the both chains)

Fluid presentation requires a fluid processor capable of responding and altering itself on-the-fly. The same flexibility is needed to accommodate new database columns or tables.

The user experience is generated in real-time starting from a default presentation. The presentation can be completely "soft" allowing easy system design change or easy accommodation of new databases or changes within. Likewise, the system itself can make alterations based on the activities driven by steps in a work-flow or reasoning chain.

Background

User interaction is traditionally cast as part of system design which is then translated by human programmers into code to make a working system. The system design is therefore only implied when working or modifying the resultant system. Documentation or original design work is then used as source from which to work when changing the system. Design flexibility requires a process or human intervention to support changes in user need or system flow.

Adding true and unfettered dynamics to a system would require unifying the design with the system to make them one and the same or an automated vehicle for generating the system from a design.

Solution

Topic interpretation translates needed structure of available data into a presentation in real-time. Removing the limitation of enforcing a system design from the screens and reports frees the interpreter to present information as a fluid flow. The need of the data is determined by topically and presented based on pre-determined soft layouts or by interpreting earlier user actions.

For example, the location, organization, formatting and order of a set of data elements are automatically organized by topic and presented as needed. The user can then change the presentation interactively. Changes can be recorded and saved as part of a process or as stand-alone. Presentations can then be played back in succession whenever needed.

It is an object of the present invention to improve access to a patient's records.

It is another object of the present invention to improve diagnosis and treatment of a patient by providing a medical care provider with relevant information from multiple different sources.

It is another object of the present invention to provide a consistent method of accessing database records.

These and other objects and advantages of the present invention, along with features of novelty appurtenant thereto, will appear or become apparent by reviewing the following detailed description of the invention.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views:

FIG. 41 also shows a hierarchy defining the existence of a data structure of one embodiment of the present invention.

DETAILED DESCRIPTION

Figure 1:
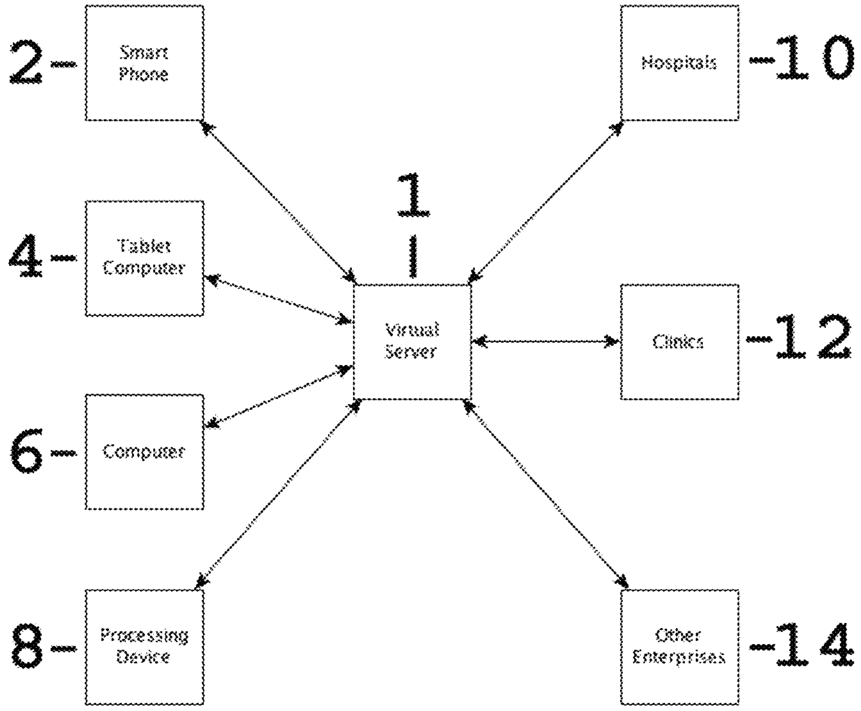
FIG. 1 is an environmental view of one embodiment of the present invention.

FIG. 1 shows an environmental view of the present invention, generally shown as 1. A user at a computing system, such as a computer 6, tablet pc 4, smart phone 2, or other processing device 8 may access information stored in a database. The database may be local or remote. In one embodiment, the present invention accesses multiple databases to obtain information and to store information. The virtual server 1 of the present invention allows the user to enter a query that will either retrieve or store information within the one or more databases. Such databases can contain information for a business or any other entity that may use a database, such as hospitals 10, clinics 12, or other enterprises 14.

Figure 2:
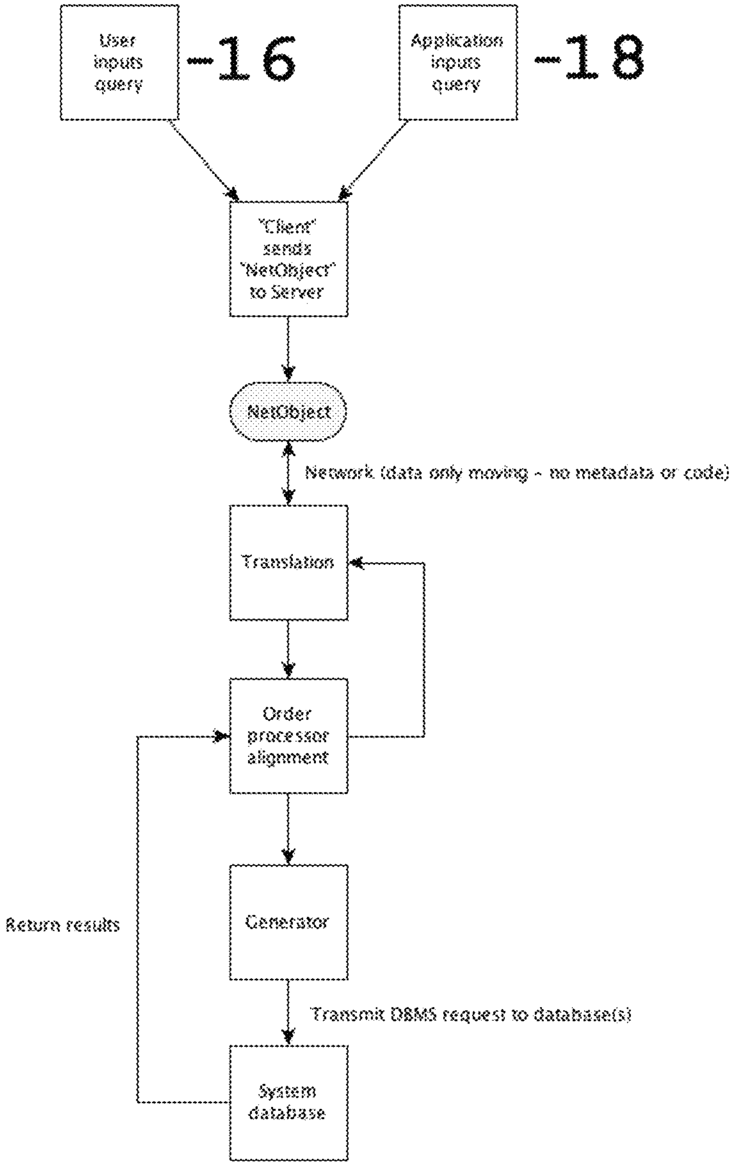
FIG. 2 is a flow chart showing the functioning of the present invention.

FIG. 2 shows a flow chart illustrating how the information is accessed. In one embodiment, the present invention is implemented on an applet. The user may enter a query 16 or the application may input a query 18 to access, update, delete, or otherwise modify information stored in a database. The client sends a netobject to the server. The netobject will be described below.

Figure 3:
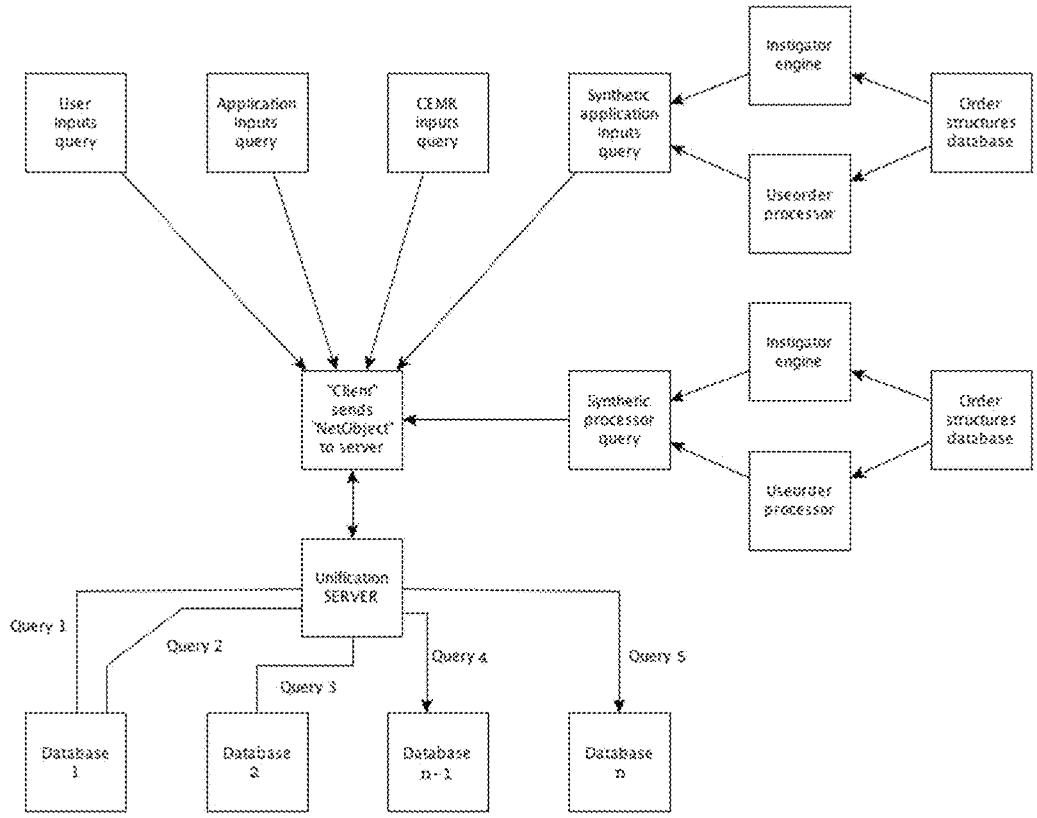
FIG. 3 is a flow chart showing the functioning of the present invention.
Figure 4A:
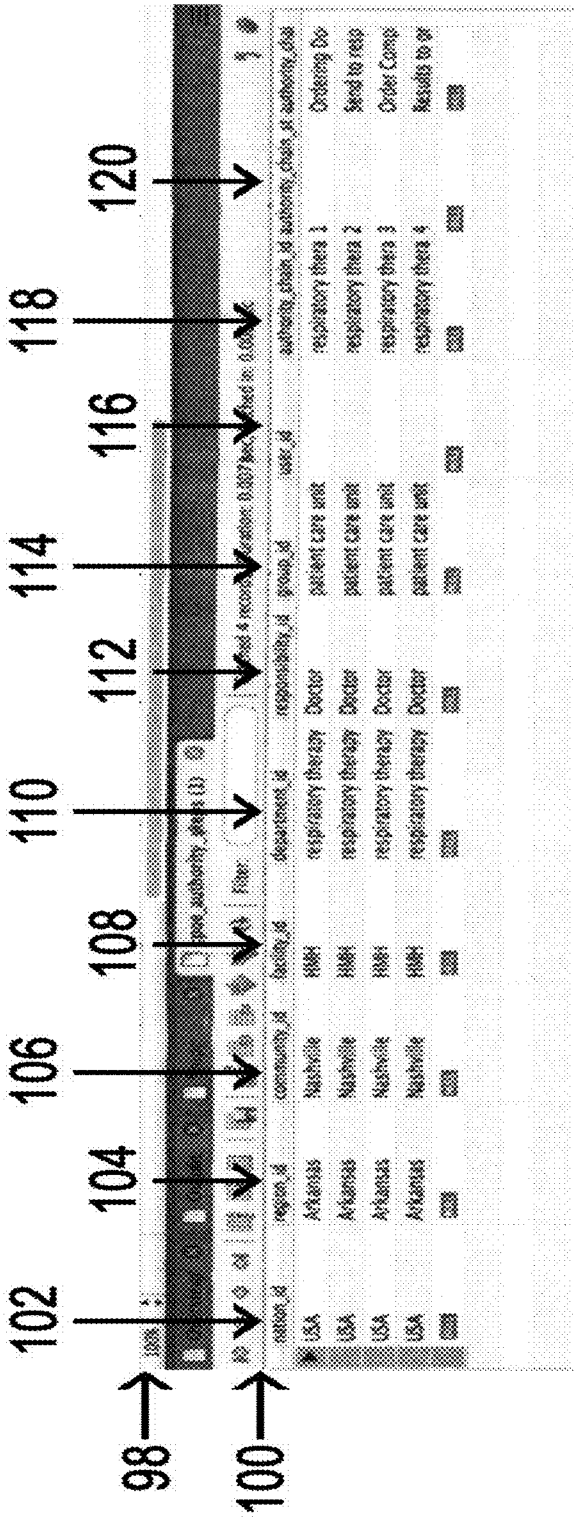
FIGS. 4A-4D are views of an authority chain of one embodiment of the present invention. The chains of one embodiment of the present invention drive the functions and tasks. The chain processor has a library of elemental functions from which a given chain step can initiate. Functions can be components from which more complex or complete tasks can be constructed. Direct functions are also supported
Figure 4B:
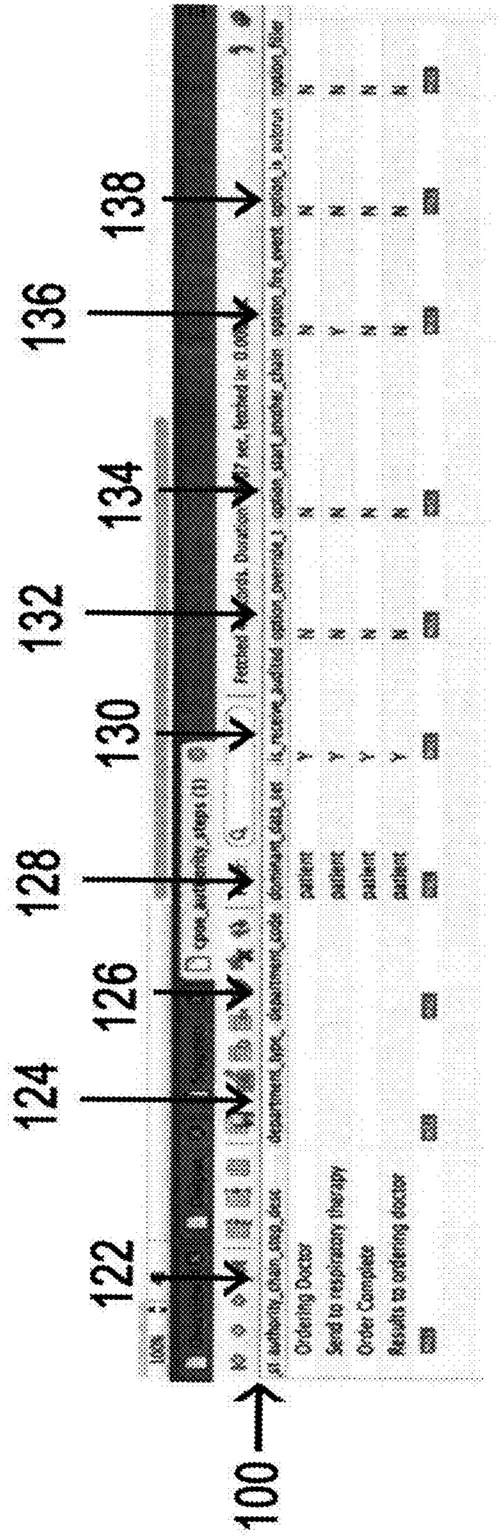
Figure 4C:
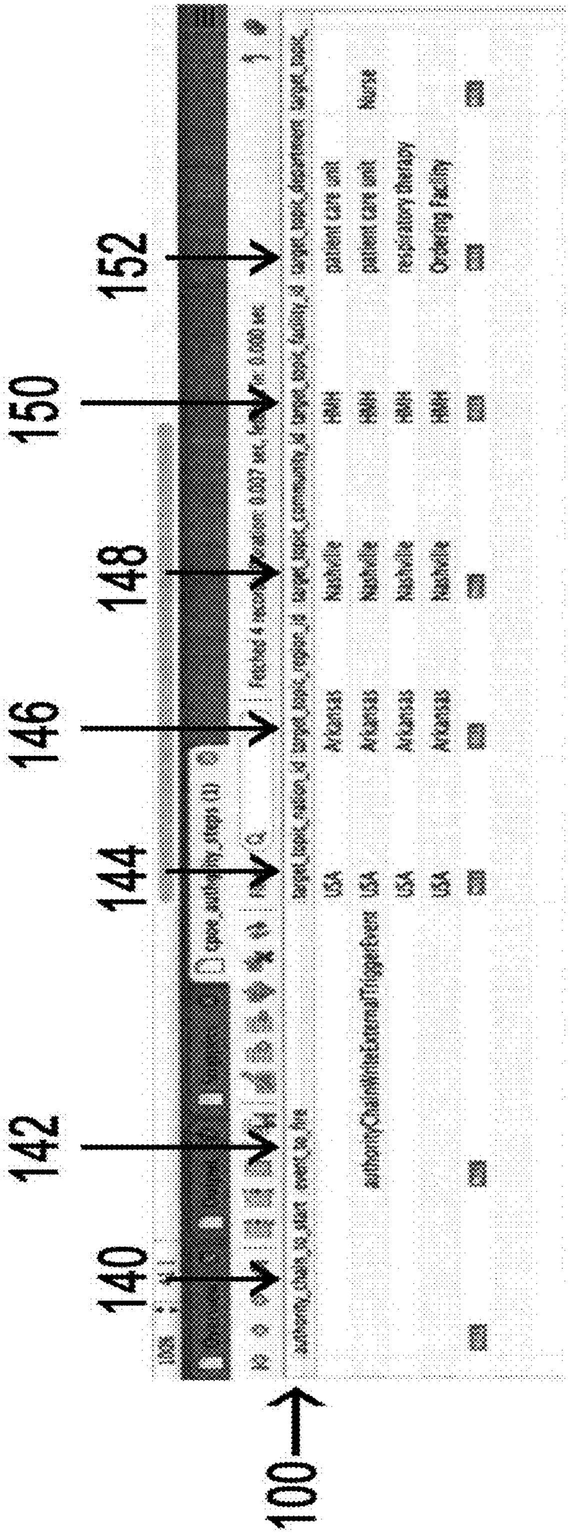
Figure 4D:
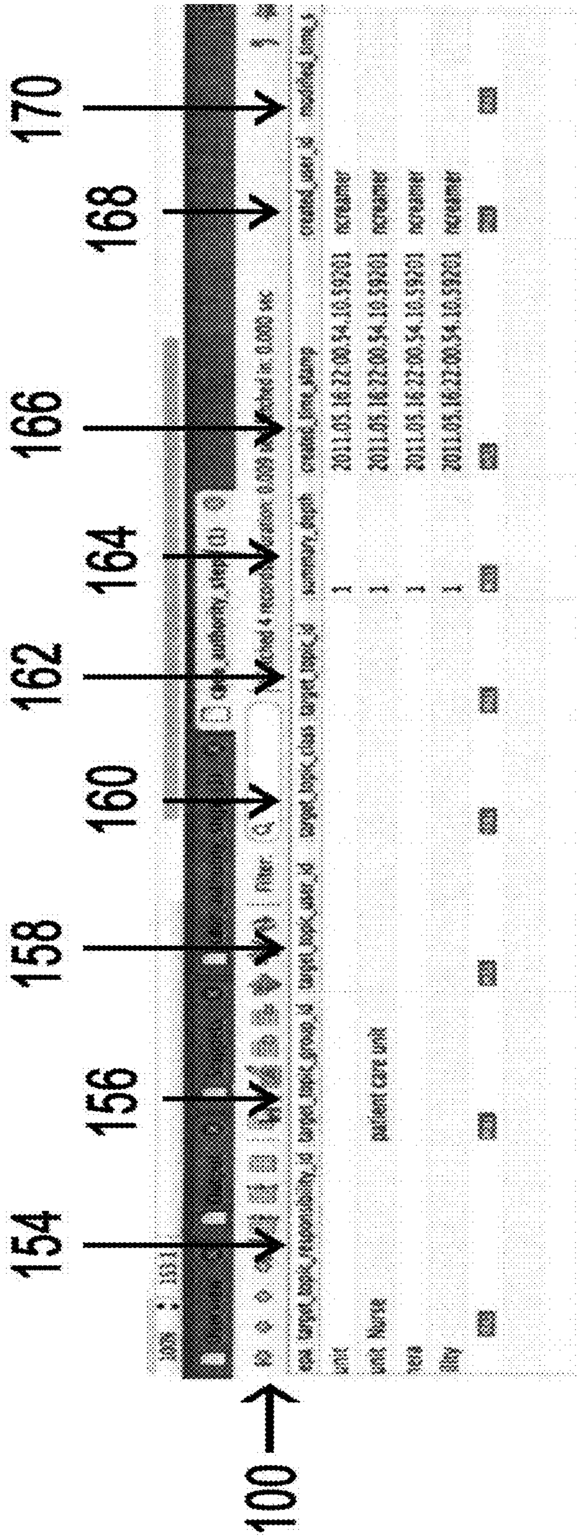

FIG. 3 shows the present invention accessing multiple databases

FIGS. 4A-4D provide information concerning one embodiment of the authority chains of the present invention.

FIGS. 29-41 provide additional information regarding the virtual logic of the present invention.

Figure 15:
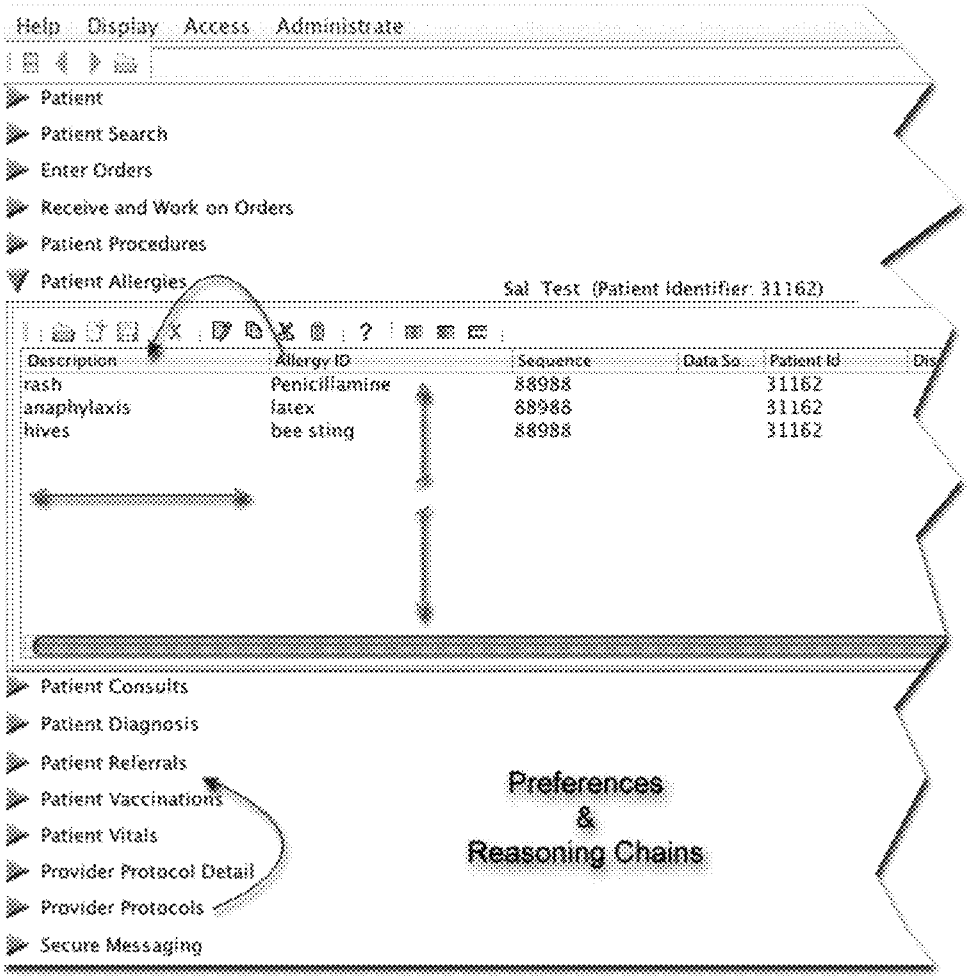
FIG. 15 shows the preferences and reasoning chains of one embodiment of the present invention.
Figure 16:
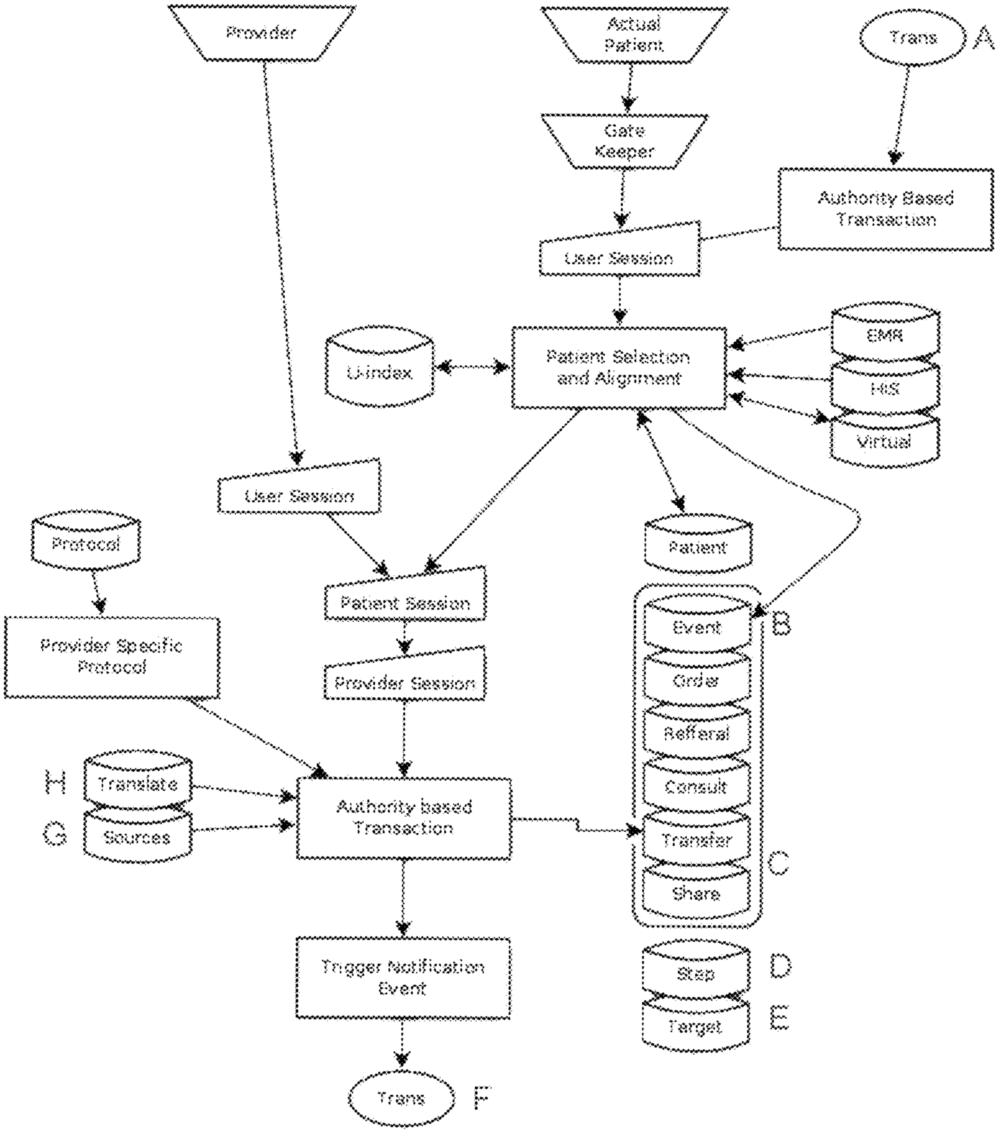
FIG. 16 shows one embodiment of an electronic medical record of the present invention.

CEMR, shown in greater detail in FIGS. 15-16, is a community-wide Electronic Medical Records access system. The system provides direct access to information in existing systems, plus the Virtual Clinic and access to HIS (Hospital Information Systems) creates a complete patient picture of medical records in a community, region or nation.

Physicians have the option of continuing to use their existing system to access patient medical information or via CEMR's web-based access portal.

As a design concept, the access portal is assumed to provide a greater set of benefits than the access methodology currently used by the medical providers within their current systems.

To that end the system provides:

- Unified views of patient information from any or all systems unified via the Unityware Unification server.
- Litigation support via automatic snap-shots of patient information as available at the moment in time when used—including indications of unavailable information.
- Access control and auditing (including a managed chain of authority)
- Standard support for patient referrals and professional consults
- CPOE (Computerized Physician Order Entry)
- Starting place for the Community Electronic Medical Records (CEMR) system. This environment is the graphics container onto which the various graphical topic modules are installed.

This environment also contains the control logic needed to operate the system and react to user events.

One of the guiding principles of the CEMR system is that Authority follows the patient, Security follows the user and Access follows the facility. The system controls the Authority to access to medical information based on need-to-know.

Authority is transferred or shared so that there is a Chain of Authority which will track back to the initial point where sharing started (say for a consult). The chain is intended to remain unbroken from the point at which the patient granted the authority to share medical records by proxy, until the last place those records were shared or referenced (say for a physician order). The concept that the authority follows the patient is called a "Chain of Authority". In other words the Authority follows the patient.

Another principal of the present invention is that the security follows the user, authority follows the patient and access follows the facility.

Separating the authority from the security provides a more fined-grain control on access to information. Security can allow a user access to the system, the facility (location of the user) limits system access, but authority is then needed to gain access to the data.

In medicine (or financial information) users may have equal access from a security point of view, but should only have access to some records, even though all of the records live within the same level of security.

C-EMR (Community Electronic Medical Records) Access System

The present invention is a community-wide Electronic Medical Records access system. The system provides direct access to information in existing systems and the Virtual Clinic. The present invention also provides access to HIS (Hospital Information Systems) to create a complete patient picture of medical records in a community, region or nation.

The present invention also allows physicians to continue using their existing system to access patient medical information. Physicians can also access patient medical information via the web-based access portal of the present invention.

As a design concept, the access portal is assumed to provide a greater set of benefits than the access methodology currently used by the medical providers within their current systems.

The system provides:

- Unified views of patient information from any or all systems unified via the Unityware Unification server of the present invention.
- Litigation support via automatic snap-shots of patient information as available at the moment in time when used—including indications of unavailable information.
- Access control and auditing (including a managed chain of authority)
- Standard support for patient referrals and professional consults
- CPOE (Computerized Physician Order Entry)
- Starting place for the Community Electronic Medical Records (CEMR) system. This environment is the graphics container onto which the various graphical topic modules are installed.

This environment also contains the control logic needed to operate the system and react to user events.

One of the guiding principles of the CEMR system is that Authority follows the patient, Security follows the user and Access follows the facility. The system controls the Authority to access to medical information based on need-to-know.

Authority is transferred or shared so that there is a Chain of Authority which will track back to the initial point where sharing started (say for a consult). The chain is intended to remain unbroken from the point at which the patient granted the authority to share medical records by proxy, until the last place those records were shared or referenced (say for a physician order).

The concept that the authority follows the patient is called a "Chain of Authority". In other words the Authority follows the patient.

Another principal of the present invention is that the security follows the user, authority follows the patient and access follows the facility.

Separating the authority from the security provides a more fined-grain control on access to information. Security can allow a user access to the system, the facility (location of the user) limits system access, but authority is then needed to gain access to the data.

In medicine (or financial information) users may have equal access from a security point of view, but should only have access to some records, even though all of the records live within the same level of security.

For example, a patient is referred from one doctor's clinic to another. The current solutions are to either ship some of the patient's record or provide access to the referring doctor's computer. Sharing parts of a patients record still requires faxes (for security reasons other electronic methods are not permitted and system to system interfaces are too expensive) or the patient carrying paper. The alternative practice in clinics today is to share access and passwords to each other's computers. In the first case the patient is under documented and in the second case too many patients' records are exposed to access without authority.

The system detects the location (facility) by the host web-page used by the user to gain access. The user logs onto the system with normal security credentials, but can only gain access to patient information if the patient is that user's patient or when a medical professional with the proxy of authority from the patient sends the authority (via an authority transaction).

The web page contains parameters which dictate the behavior of a user session. Some of the parameters are keys to tables which define which parts of the system (or parts of a screen) are to be made available.

The system administration staff can add new web-pages to fine-tune system access for any logical collection of users (i.e. department or skill level). For example, different pages for the clinician, attending physician, admission staff, information technology department, in-hospital nurse, billing or the patient.

Users are associated with access groups, departments, skill using a Unix-like security approach. Any form of traditional security for the user will work.

Access authority of the present invention is based on actual permission. A patient gives a physician in a clinic the authority to see that patient's medical records (usually by signing a form). The patient's permission can then be transmitted to other physicians or medical services as a proxy through the present invention. Authority transactions work using the same idea in electronic form. Doctor A asks doctor B for a consult and, by doing so, passes authority to see the medical records. An authority transaction passes the patient's authority proxy which automatically grants access to the patient's records.

Authority transactions are not required to be patient-centric. The same process could transact authority for information about the physician, facility or non-medical processes like ordering inventory.

One embodiment of the data access system starts from a web browser using a pre-defined webpage that calls the applet and the initial parameters. (See AppletParameters for the names of the parameters and possible values).

Authority—the data access system uses a patient centric method. In one embodiment, the patient centric method provides the security measures.

The system requires authority before a user can access a given patient record. The authority is generated by the physical activities surrounding a real patient. For example, reviewing the historical diagnosis of a patient would only be required when seeing or working with a specific patient.

Controlling access to the records of a patient requires that any action involving a patient has specific permission for the current patient related event.

The patient, legal guardian, or another person with legal authority must grant permission to access the patient's records. Such permission is accomplished via patient admission or gate-keeper staff and recorded via a protocol using physical paper and hand written signatures. Systems then conform to the patient directives for access authority.

Portable authority—Actual patients have a paper trail whether the provider is automated or not. Specific and reliably defined methods allow access to a patient record to be shared or transferred between providers.

Providers may need to know patient history when examining the actual patient or making decisions or determinations. The patient is given access to a care provider according to the same method that is accepted for controlling access to records. Patients grant access to their medical information as a requirement of receiving medical services. For example, a referral request may be faxed between doctors with the implication of sharing the patient's authority and the patient's records.

Authority Chains—

Authority chain steps control the order in which discrete user or system tasks are initiated and executed.

The authority transaction is an explicit communication of authority which allows access to the information that would have been on the form. The steps of a chain transport a proxy of the patient's authority from task to task. The authority connects to instances of medical information in a multitude of systems providing information that would otherwise be unavailable. The process is also applicable for non-medical information in other industries.

A collection of authority chain steps defines the ultimate "route" of a workflow from one person or system to another. The system does not require user to send the results of the work to the next step. The system automatically "knows" where the next step of a workflow is after the completion of any given step.

It is possible, at any point in the process where a human is interacting with an order that the user may decide based on circumstances that the order should follow a different chain of authority than the one that was originally assigned at the time of placement. The system will handle the requested diversion by simply allowing the person to select the next step, effectively creating another chain of authority including the selected step and the attendant steps associated with the selected step.

Authority transactions are initiated through the transaction entry process. Each transaction is assigned an action (i.e. task to be ordered or directives) for the transaction from a list of possible actions. For example, procedures may include X-ray, sleep study, drugs, or consult. The reasons are order-able items or other physician/professional directives. For the purposes of this document we will reference them as authority actions.

The user also assigns a reason for the ordered (can be a directive) task, item, or action including but not limited to a diagnosis or other authority reasons.

Chain Initiated—

Transactions are started by selecting a given authority chain. The systems lists the name of chains (that are applicable for the kind of user and facility) to be displayed in a menu-like list. For example in one embodiment, Order radiology for out-patient, order drugs for in-patient or move a patient to ICU may be included in the list. The menu is hierarchical allowing the user to "drill down" from the general to the specific.

Chains—

The authority chain is always initiated. There may be single step chains or a chain may start when a patient walks through the front door of a clinic. For example, a chain called "Patient visit" could start the necessary process for verifying patient demographics and insurance. The chain then starts the correct screen for recording vitals by a nurse and then starts the correct process for the exam room when the physician arrives.

Chains can also include protocols when transactions are chain initiated. However, protocols may require the steps to all be listed on a single screen/document from which the user chooses from options and sees the required items as a list of directives which are generated as authority chain steps. The directives are the authority chain steps which will guide workflow between tasks.

Routing—

Authority transactions are automatically routed to one or more users based on a geo-location key. Transactions can be generated so that the transactions are sent to every user within the nation or to a single person by name.

Examples of the routing include:

Single individual

People of the same skill set

All of the people in a department

People of the same skill in a specified department

People of a specific skill set, in a specific department in a range of time (shifts)

Processing Steps & Work-Flow—

Users are presented with a screen containing two lists. The first list includes items that are awaiting user action, "in baskets". The second list is the items which the current user has accepted for processing. The user selects an item from the first list to accept the item for processing. The second list includes the items currently in process for the current work step.

A user accepts an authority transaction by clicking on it in the "in basket" window. Accepting an authority transaction automatically removes the same copy of that chain step from the "in-baskets" of other recipients, thus accepting the authority and task for processing. The same line that also appears in other user's "in baskets" automatically disappears (unless chain step is set otherwise and that step should be terminal).

Optionally, a chain step may be used for notification. Selecting the item from the "in-basket" does not remove the same entry from the other recipients if the chain step was used for notification. The result of selection is an audit that it was selected at this work step. Audit will indicate that the recipients received the message, instructions, etc. when selected.

The user takes action to fulfill the requirements defined by the chain step item which that user had previously selected from the "in-basket". The user then adds any new information resulting from their efforts and clicks complete and the line automatically disappears. Easy access to a list of all processed steps is available as history.

The next step in the authority chain is automatically initiated when a user completes a line. Transactions flow into the top "in basket" list and out the bottom processing items list. Each step in the chain duplicates that process for each step in the workflow. In this way, transactions flow from one user to the next in a continuous work-flow.

The transaction is forwarded for each step in the chain including any new information collected along the way, for example, a radiology report or an indicator that a physician directive has been completed.

The new information resulting from a given work step in an authority chain step is added to the authority object transported from step to step. Users or processes have access to the information collected throughout the chain. The result is a transactional process which emulates the tasks normally associated with the processes within and between departmental software applications.

For example, a medical directive that specifies a radiology procedure for a given patient may first arrive in a hospital's scheduling department where a date is added. The authority transaction then automatically transfers to the department, where someone calls the insurance company and receives pre-authorization for treatment. The authorization is added to the authority transaction and automatically sent to an admissions councilor, where it awaits the arrival of a patient. The admissions representative may interview the patient and add some additional information about how the procedure is to be performed or billed. The transaction would then automatically transfer to the radiology department and await the patient arrival. The next steps include a radiologist who interprets and records an opinion and the originating physician receives the transaction as results.

In some instances, a user, who already accepted the authority transaction, must stop work or refer the work to another person of like or more appropriate skill. In this case, a new step is inserted into the authority chain and released to the new step previously inserted. A user can adjust the steps of the chain such that the chain appears as it was before the user had accepted the step. Therefore, the user's inability to complete the step will not affect the chain. Chains can be bi-directional. Chains can also fork and merge.

The inserted step is an ad-hoc step and can be focused to a single individual or a group at any level in the geo-location key. However, if the step is simply to transfer work between people in the same department the recipients will be the same as the current step.

The inserted or modified step is edited in the same window as a step that is being processed. For example, a tech in a pharmacy may release a step he or she is processing, but change the target from a nurse on the floor to the pharmacy. The system would then automatically insert the new step, update the audits and continue the chain.

Steps contain bi-directional identification codes for the next and previous step to allow the user to follow the chain in both forward and reverse order.

Variations of Workflow—

The users may adjust workflow by transferring authority to a step or user out of the defined chain of authority. Subsequent transfers can also forward the authority step off of the defined path (managed as sub-steps). The work-flow will automatically re-start at the next unprocessed step as defined by the original authority chain.

For example, the user may transfer authority to a process by another software system or device. A pharmacy system, for example, may be interfaced and presented with an order for drugs (as specified by a step). It is unknown when or if the pharmacy system will return a result that would trigger the chain to move onto the next step in the authority chain. The same is true for devices.

The authority chain then has a "forecast" step which acts as a placeholder at that point in which the pharmacy system is expected to return a result. An optional chain could be triggered after a suitable period of time which notifies the correct people that the pharmacy has lost the order or the pharmacy system simply failed to report. Other options include monitors for other chains which should only be running if the drug showed up on the hospital floor. The same is true for devices or manual steps.

Any defined response to a failed step can be defined including but not limited to terminating the chain, triggering other chains, merging chains or simply continuing to the next step. Any chain step can be defined to effect, change, diverge, merge, reverse, etc. the flow.

Changes in the work-flow automatically prompt the user for an explanation which is recorded in the normal audit generated by the authority chain processor.

In some situations, one or more required steps could be skipped. In these cases, the system will automatically prompt the user via a pop-up dialog. The pop-up dialog may include text either provided by the chain step or a central repository of reasons and solutions to explain the reasons and/or solutions.

Audits are generated automatically by the implementation of a protocol or each chain step executed.

Variable Routing—

Steps can specify the target down to a specific user, to all of the users or any range specified by the geo-location key (nation, region, facility, department, skill group or user). The authority chain processor also supports variable targets. Steps can bifurcate into other chains which run concurrently or exclusively of one another. In addition, multiple chains can be merged into one chain.

Breaks in the Chain—

It is also possible to "break" a chain to support other automation which does not have the capability to interact with chains. In this case the next step in the chain is set "pending" awaiting the completion of some external task. The external activities are represented by a single entry in the authority chain which is set to wait. The external process may involve as many systems and people as needed. The external process is represented by a single chain step. The user provides the system with the results of the external process to complete the pending step to trigger the next step of the authority chain.

In effect, the pending step is projected forward in time and waits for the completion of an unmanaged task. The pended step then waits as the external process is allowed to catch-up.

Links in the Chain—

Each step references the next step. Steps can collect additional steps along the way. Each of the appended steps reference the same step as the one to which they are appended, but have their own appended step id.

Reversing or re-processing a chain will display appended steps. Appended chain steps (sub steps) will not be processed if they were added during processing (e.g. transfer transaction between two pharmacists). Such (sub-steps) appended on the fly may be suspended during another pass for the same parent chain being processed in either forward or backward direction. Sub steps which are part of the source authority chain are processed in forward order when the chains are being processed in either forward or backwards order.

Steps—

An example of bifurcated chains would be when a chain splits to send the authority transaction to the coding department for billing and sends notification back to the originating user. In this example, the originator or coding department may process the chain before or after the other chain is available for processing.

The authority chain processor also allows chain steps to variable target facilities, users and the like. The chain steps are accomplished by having multiple sub-steps where each contains logic excluding the others. Chain steps which have appended sub-steps maintain a parent-child relationship where the parent is a normal step and the children are variations. Such chain steps allow a way to root a collection of possible chains to a single step in the chain. The child steps each connect to the start of a new chain. Forks are created when the logic associated with all of the children is mutually exclusive. Bifurcating the flow into multiple chains is handled by having logic which is not mutually exclusive.

However, there are conditions when the step targets a user based on one of the values contained in the authority transaction or a value from the system. For example, a user in a given facility originates the chain to return the results to the attending at the same facility.

In our example case, the authority chain processor references a variable from within the transaction. The geo-location key is not or is partially defined (the recipient of the step is not defined or is partially defined) until the authority transaction is processed. Logic or rules determine the actual recipient or recipients (range of definition in the geo-location key). The user at the previous step may also select the recipient(s). In the example above, the attending physician is automatically selected based on rules that point to one of the objects carried by the authority transaction (carries patient, provider, facility and the like) or a reference using data that is transported along with the authority transaction.

Steps can specify a target based on a system value, which includes system time and date. For example, on Mondays the transaction is sent to an outpatient radiology center, Tuesday through Friday, the transaction is sent to the hospital's radiology department. On weekends, the transaction is sent to the emergency room.

Sub-chains are expected to handle steps in the work-flow which are not predicted by the defined reasoning chain. For example, the system may transfer authority between two people in the same department in steps that allow either person to accept the authority. Sub-chains can define alternate options associated with a given step or initiate multiple other chains.

Branching chains initiate another chain which can run in parallel. Secondary or alternate work-flows process without respect to the timing of the originating chains. It is therefore possible for a secondary chain to reach completion when the initiating chain has not yet completed the next step.

Optional steps can forward the process beyond a given step based on logic. The logic can test values at the time the step is being tested for use or skipping. Skipping steps on logic can by-pass a specific work station or allow selection of one department/work station by having a collection of steps where the logic is mutually exclusive for each.

Multiple possible branches can exist where each is attached to a sub-step which has skip logic. The secondary chain starts when the logic returns true. It is perfectly acceptable to have various chains initiate one right after the other. For example, first alternate sends to coding/billing, next initiated chain goes to quality review while yet another goes to records.

Optional steps can be skipped based on user's response or selection. These steps predict the possibility of alternate work-flows and proactively prepare possible items that would have to be recorded. It is possible to attach a collection of possible optional steps as sub-steps to a single normal step that can be skipped at the user's option. Skipping the normal step will automatically skip all of the attached sub-steps. Optional steps can be skipped on logic without user interaction.

Temporary chain steps, such as notifying the CFO about an expensive procedure, that automatically turns off based on logic, number of times/date processed/logic (or example, user defined/temporary/self-expiring sub steps).

Temporary chains can be added by an authorized user. It is expected that the temporary chains provide notification. Temporary chains have all of the same capabilities as normal chains. The only visible difference between a temporary chain step and a normal one is a simple indicator in the message. Subsequent chains steps attached to a temporary chain step must also be temporary.

Subsequent chain steps cannot expire after the previous temporary chain step. The options are that the user is limited to the earliest previous expiration condition or that the previous expirations are updated when a subsequent chain step's logic exceeds the limits.

Temporary chain steps do not have to expire, but can do so based on logic. The logic can check time/date, value (such as cost drop below a set value), events including the first time something is encountered (such as a new procedure). Counting the number of events may also be supported.

Dynamic step target supports determining the actual next recipient based on values present at the time the step is processed.

The present invention may also select the target of a chain step based on logic. One example may include the originating physician and facility verses any physician in the community. Chain steps can control the flow of other chain steps based on logic or rules. Any chain step can initiate any chain function for example, switching to another chain, initiating a parallel chain (secondary), breaks in the chain, merging chains.

Automatic steps that do not cause user interaction. Automatic steps cause processing which does not (or may not) involve the user. One example includes picking up data from a modality or updating an automated drug dispensing machine. Automatic steps can act like programs moving data between systems or tables or adding new data as encountered in a given step.

Merge chains support alignment of independent work-flows which all must wind-up in the same place. For example, labs, radiology and the radiological consult all need to be collected in coding/billing. In cases where the HIS is not able to handle a set of departments the authority chains could suffice.

Chains can be merged when a chain is broken, steps are skipped, secondary chains merge or unrelated chains converge. In the cases of broken chains or skipped steps, the user is required to record a reason for audit, for both at the point where the chain becomes discontinuous and at the point where it re-starts or merges.

Chain transaction—Each step in the chain pushes the same authority transaction forward to the next step. However, any permutation/combination of steps can be processed including processing the chain in reverse. For example, notifying the originating user would be a closed loop following a chain from user to user until it arrives at the chain's end which, in this example, happens to be the originating user. Other non-display values are transported by the authority transaction to enable automatic processing, chain step flow and logic in later steps.

The chains of the present invention drive the functions and tasks of the present invention. The chain processor has a library of elemental functions from which a given chain step can initiate. Functions can be components from which more complex or complete tasks can be constructed. Direct functions are also supported (for example sending an SMS message or initiating a network or system event).

An action (user event, external system or timed event) initiates a chain. Each chain step can carry one or more values to indicate behavior. The values can be used to determine the conditions on which the chain starts, the behavior of the chain once started, or the next function (or step) to be executed.

A chain is started when a value is presented that matches a value within the first chain step. The chain step can carry definitions on where to look for that value (for example field in a list of values) and the conditions on which to affect behavior (default being match to a value).

The chain processor awaits the specified definitions to be satiated and then starts the appropriate chains. Chain steps can call functions with which the data may be processed or take other action. A given chain step will carry a name of a given ability which will tell the chain processor to fire that ability. The steps can await external stimulus (i.e. a user action) or operate independently of any external influence.

Chain steps can be told to read or write data or any other programmatic function. Processing works best when the callable functions are simplified to a single function. This allows the chain processor to combine abilities to create permutations dynamically instead of having to choose through a list of pre-programmed permutations.

Elemental functions can be as simple as math or character substitution. Logic is usually not required. The conditions present will simply cause one chain to fire over others. For example, receiving physician's progress notes from another system could fire different chains based on the state of physician's signature (not signed, not reviewed, not complete, or signed). The ability to model without expressed logic significantly simplifies chains and simplifies the process of enhancing and/or modifying the application.

The chain processor examines each chain step, in order, and then calls out the appropriate functions. Data is transmitted between the elements via a soft bus which provides a universal environment within which any element receives data, processes the data, and then passes the data. The present invention may also simply store the data within memory to share the data amongst the elements when the next element is loaded.

One or multiple chain steps may represent complete processes. Steps can be automatic (without need for external or user interaction) allowing for the definition of complex automation processes.

Step activity can be controlled from external systems, for example, awaiting a response from a remote system. In such an example, a step initiates a command to a remote system and then another step awaits the response.

Each step uses the same machinery to invoke behavior and then passes control to a tangential chain step (backward, forward, skip or another chain). Users can also affect chain processing order. By user action, a chain could be reversed or processing skipped to an earlier step. For example, rejecting a directive received from user A by user C could send the process back to user A or B.

Chains can carry data and transport transactions between tasks (people or machines). Chains can also collect new information at each step which may be carried forward or stored in a database. New data or situations can affect the processing of the chain (or start another chain and/or terminate a chain). As steps move between users, data is collected which benefits down-stream users. Chain steps can be defined at a very fine level of granularity creating a user environment which smoothly amalgamates information with less burden on any given user.

Chain steps can direct multiple types of behaviors at the same time, for example, an elemental function that translates data (or some other form of manipulation) and an event.

There is no natural limit to the kind of actions that can controlled by steps. For example, controlling equipment like test devices or a PLC. Likewise, there is also no natural limit as to how a chain is to be started. For example, a chain may be started because data was added or modified in a given database table.

Note: there need not be a separate system design from the model represented by the chains. The chains of the present invention are capable of replacing traditional system design. Systems can be pressed into service the instant an idea is recorded as a design (model).

Each chain 98 provides customization that enables the system to be quickly adapted for use in different environments. Each chain 98 has at least one chain step 100 as shown in FIGS. 4A-4D. The different chain steps 100 define the manner in which the information will flow. In one embodiment, each chain step 100 is associated with a nation identifier 102, a region identifier 104, a community identifier 106, a facility identifier 108, a department identifier 110, a responsibility identifier 112, a group identifier 114, a user identifier 116, an authority chain identifier 118, an authority chain step identifier 120, an authority chain step description 122, a department type identifier 124, a department code 126, a dominant data set 128, an is received audited field 130, an option override target field 132, an option start another chain field 134, an option fire event field 136, an option is autorun field, an option filler 138, an authority chain to start 140, an event to fire 142, a display visibility field, a target topic nation identifier 144, a target topic region identifier 146, a target topic community identifier 148, a target topic facility identifier 150, a target topic department identifier 152, a target topic responsibility identifier 154, a target topic group identifier 156, a target topic user identifier 158, a target topic class name 160, a target topic identifier, a summary depth 164, a created time stamp 166, a created user identifier 168, and a modified time stamp 170, a modified user identifier, a retired time stamp, and a retired user identifier.

Each chain step 100 associates the chain step 100 with a location, facility, and department. The chain steps 100 may be customized according to facility to allow the system to be quickly adapted for a particular facility. Each chain step 100 is also associated with a responsibility (professional type: such as doctor, nurse, anesthesiologist, specialty, etc.), a responsible group, a responsible user, a responsible department identified by type and code. Associating the chain step 100 with a responsible party enables the system to be implemented in different facilities more quickly and allows the system to be quickly customized according to the needs of the facility.

The chain step 100 also identifies the chain 98 to which the chain step 100 belongs at authority chain identifier 118. Each chain step 100 is assigned a step identifier 120 that indicates the chain step's 100 placement within the chain 118. To modify the steps of the chain 98, the user amends the step identifier 120 to adjust the steps of the chain 98. The step identifiers enable the system to progress through the chain.

Each chain step may initiate another chain as shown at option start another chain 134 and authority chain to start 140. The authority chain to start 140 identifies the authority chain to start. Each chain step may also fire an event as shown at option fire event 136 and event to fire 142. Similar to the authority chain to start 140, the event to fire 142 identifies the event to fire.

An is receive audited field is associated with each chain step. The is receive audited field indicates whether the chain step should receive information before progressing to the next chain step allowing the system to wait for an external event. If the chain step should receive information, the chain will not progress to the next step until the information is received.

Each chain step also provides a target facility and associated target fields. The target fields, including the target facility, a target topic nation identifier 144, a target topic region identifier 146, a target topic community identifier 148, a target topic facility identifier 150, a target topic department identifier 152, a target topic responsibility identifier 154, a target topic group identifier 156, a target topic user identifier 158, a target topic class 160, identify the target of the chain step. This target information defines the eventual terminus or goal of the process to which the eventual effect will be applied.

Figure 5:
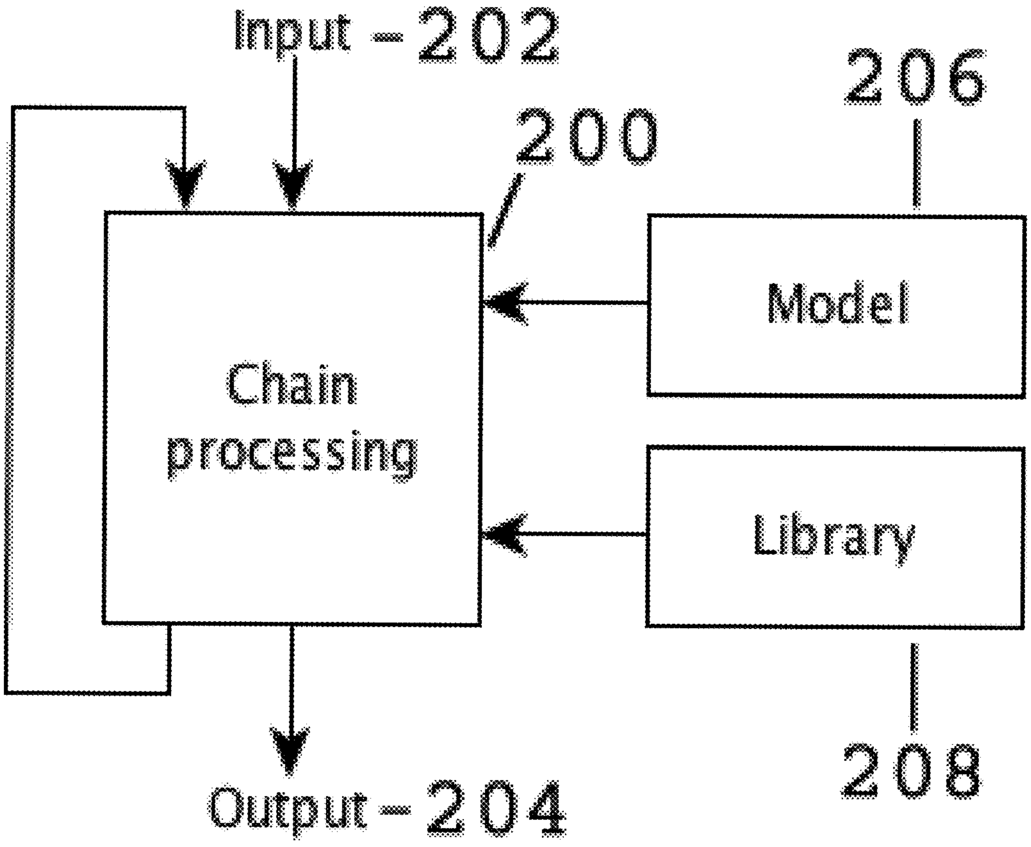
FIG. 5 is a flow chart showing the chain processing of one embodiment of the present invention.

FIG. 5 shows the chain processing of the present invention. The chain processing unit 200 accepts input 202 that may include data and/or a chain 98. The chain processing 200 applies rules defined in the model 206 and/or library 208 to the data and/or chain 98. The model 206 and library 208 identify the manner in which steps 100 of the chain will progress. Chain processing 200 applies the rules to the data, chain step 100, and/or chain 98 to achieve the appropriate output 204. The model 206 and library 208 identify the processes, functions, function calls, and other system protocols that will occur as the chain and the steps of the chain are processed. The model 206 and library 208 identify how the data will be processed, transmitted, and/or handled throughout the chain and the steps of the chain.

Figure 6:
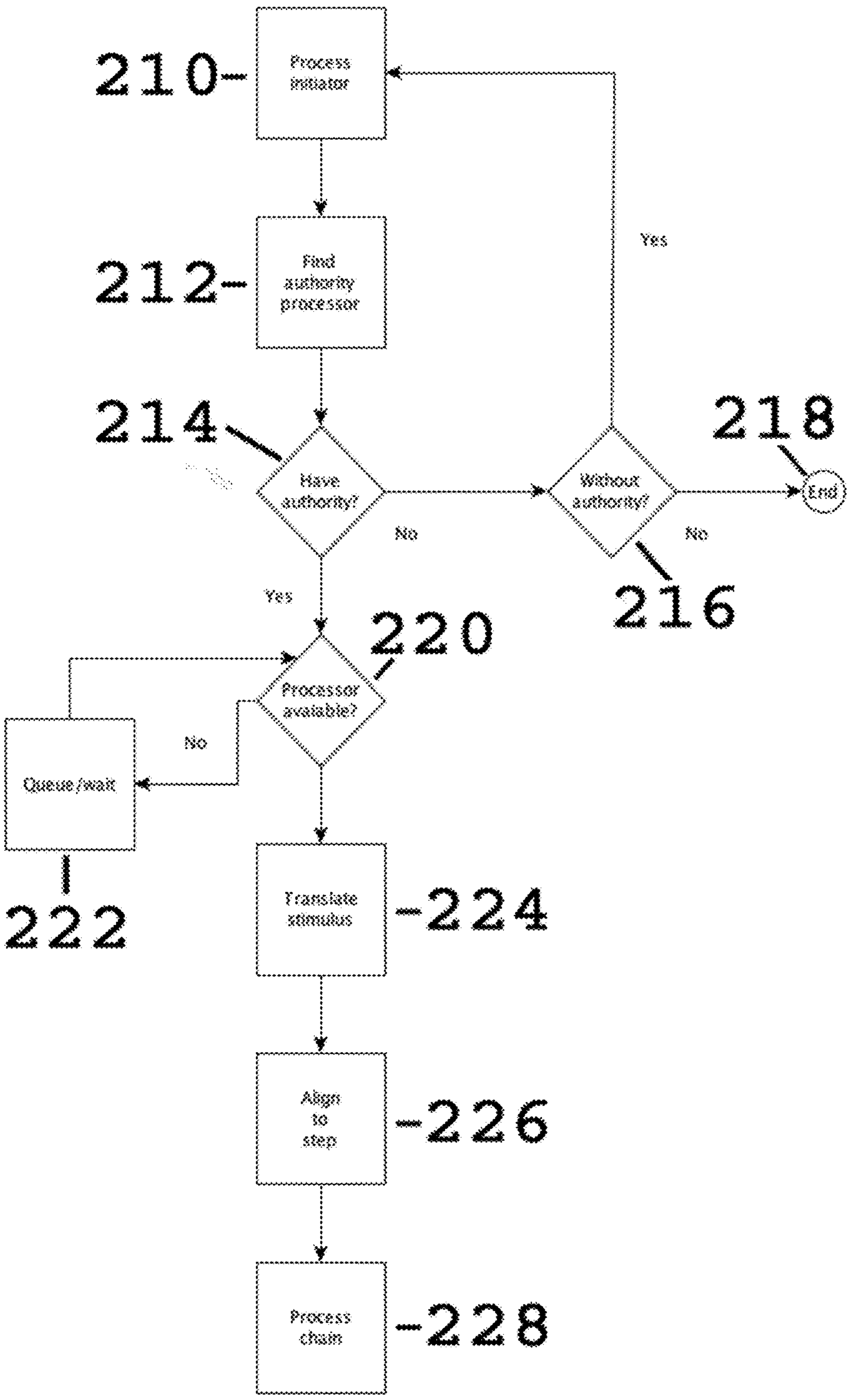
FIG. 6 is a flow chart showing the initiation of a process of one embodiment of the present invention.

FIG. 6 shows a process initiator 210 that initiates a process. The system identifies the user(s) who have authority at find authority processor 212. In one embodiment, the authority of the users is identified within the chain 98 and chain step 100. The authority may be based upon authority identifiers such as the nation identifier 102, region identifier 104, community identifier 106, facility identifier 108, the department identifier 110, the responsibility identifier 112, the group identifier 114, and/or the user identifier 116. Therefore, users who meet the qualifications of the authority identifiers may proceed with the chain. Other authority verification methods may be used. If the user has authority at authority query 214, the system progresses forward through the process to determine if the processor is available at processor available query 220. The process enters the queue or waits until the process is available at step 222 if the processor is not available.

When the processor is available, the system translates the stimulus at translate stimulus step 224. The stimulus may be user initiated or system initiated. The system identifies the stimulus, the authority chain identifier 118, the authority chain step 120, and the state to determine the manner in which the system should proceed. Considering the stimulus, the system aligns to the step to be executed at align to step 226 and processes the chain at process chain step 228. The stimulus initiates the chain and chain step to be processed. At translate stimulus 224, the system processes the stimulus to identify the chain and chain step to be processed. The system aligns to the step for processing the chain.

Figure 7A:
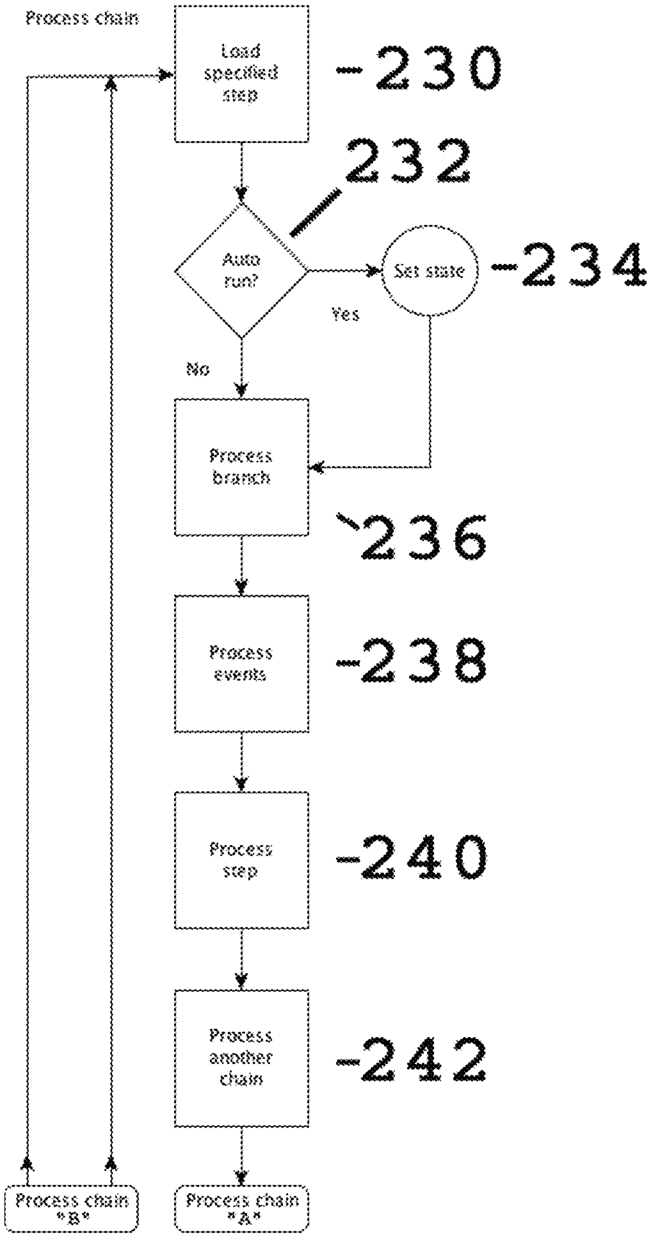
FIGS. 7A and 7B are a flow chart showing a process chain of one embodiment of the present invention.
Figure 7B:
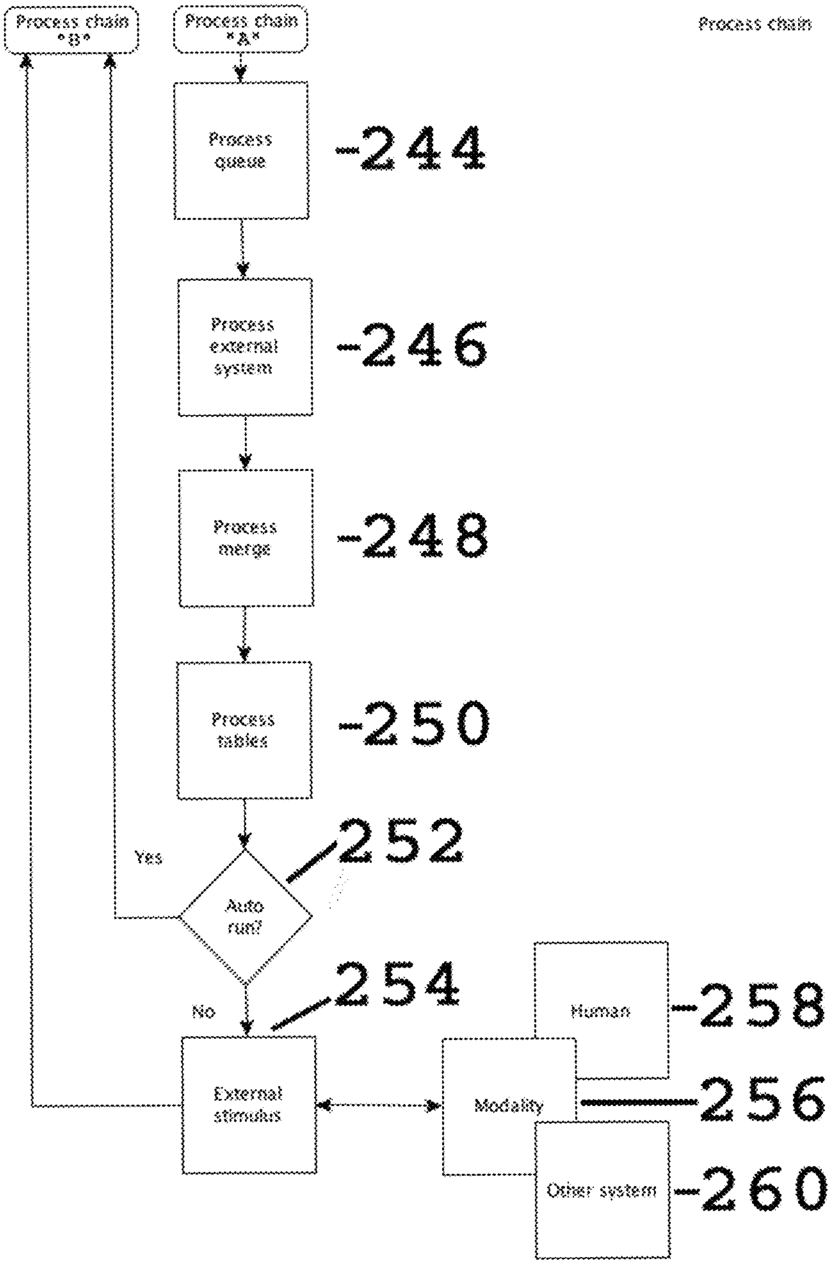

FIGS. 7A and 7B show the processing of the chain. The system loads the specified step at load step 230. The stimulus identifies the chain and chain step to be processed. This step may be identified based upon the authority chain identifier 118 and the authority chain step 120. The authority chain step identifier 120 distinguishes each step from the other steps within the chain. If the chain is to be auto run at auto run query 232, the system will set the state at step 234 and process the chain. The state identifies how the chain step will be processed. The system processes the chain at process branch 236 shown at FIG. 8, process events 238 shown at FIG. 9, process step 240 shown at FIG. 13, process another chain 242 shown at FIGS. 7A and 7B, process queue 244 shown at FIG. 12, process external system 246 shown at FIG. 10, process merge 248 shown at FIG. 11, process tables 250 shown at FIG. 14. If the state is set at autorun at autorun query 252, the system will move to the next step of the chain and continue processing the chain at load step 230. If the state is not set to autorun at query 252, the system will progress to step 254 where the system waits for a stimulus. Such a stimulus may be human 258, modality 256, or another system 260. Once the system receives the stimulus, the system moves to the next step of the chain and will continue processing the chain at load step 230.

Figure 8:
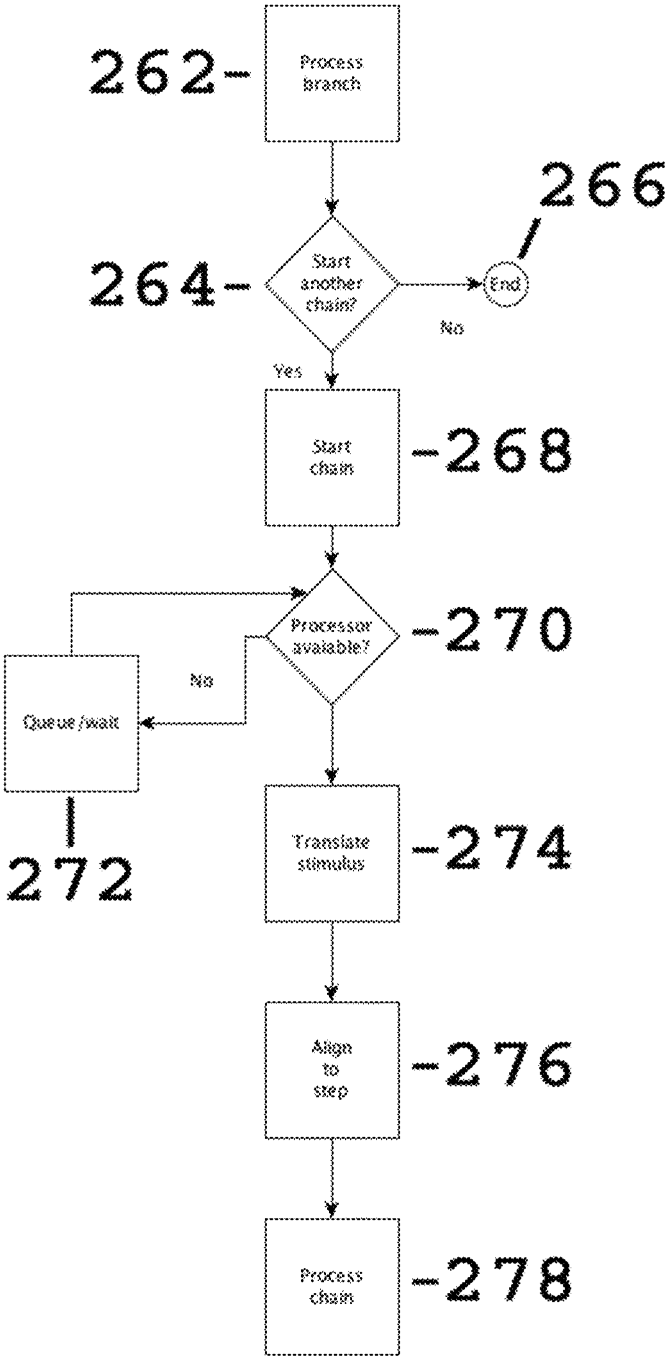
FIG. 8 is a flow chart showing a process branch of one embodiment of the present invention.

FIG. 8 shows a process branch 262 of one embodiment of the present invention. At start another chain query 264, the system checks to see if the chain step should start another chain. In one embodiment, each chain 98 stores information identifying whether the chain step should start another chain, option start_another_chain 134, and the identifier of the authority chain to start, authority_chain_to_start 140. In one embodiment, the system checks to see if the option_start_another_chain 134 indicates whether to start a chain and checks the authority_chain_to_start 140 to determine the identifier of the authority chain to start. In another embodiment, the system only checks that authority_chain_to_start 140 to determine the identifier of the chain to start. If authority_chain_to_start 140 field is null, empty, or blank, the system will not start another chain at the current step. Therefore, if the chain step indicates that the chain step should not start another chain, the process branch will end 266 and move to the next step of processing the chain.

If the chain step is to start another chain, the chain starts another chain at start chain 268. As described above, the processing of the chain 98 and chain step 100 continues when the processor is available at 270. The processing of the chain enters a queue and/or waits 272 until the processor is available. As described above, the system translates the stimulus 274, aligns to step 276, and processes the chain 278.

Figure 9:
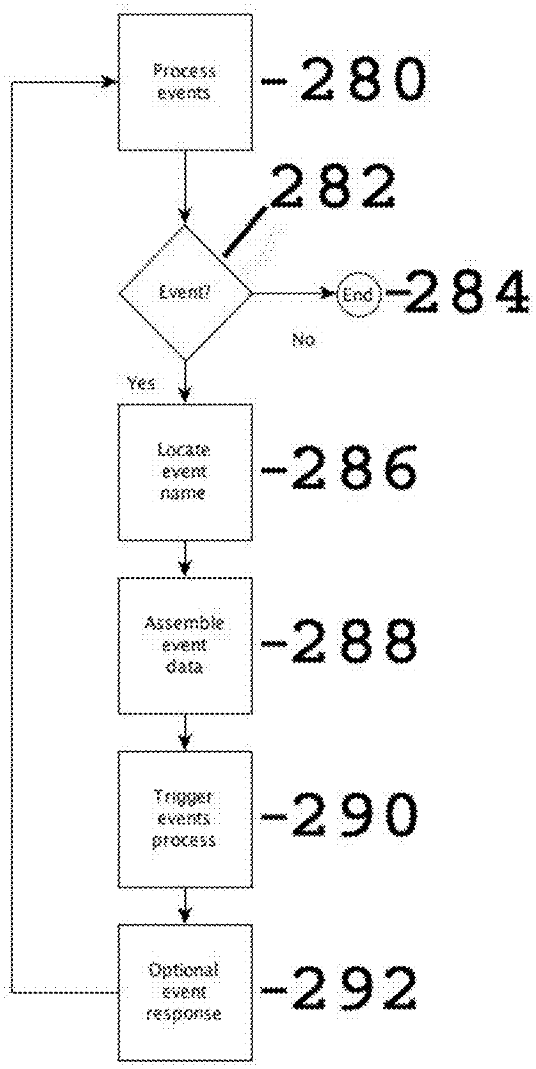
FIG. 9 is a flow chart showing a process event of one embodiment of the present invention.

FIG. 9 shows the process events 280 of the present invention. The system checks the chain step of the chain 98 to determine if the chain step should start an event at event query 282, the system will identify the event and start it. Otherwise, the process event ends at 284. The system checks the option_fire_event 136 and event_to_fire 142 of the chain step to determine the identity of the event to fire. The system locates the event name 286 within the chain step. The system assembles the event data that is needed to execute the event. The system triggers the processes of the event at trigger process 290. The system also determines if the event should provide an optional event response at response 292.

Figure 10:
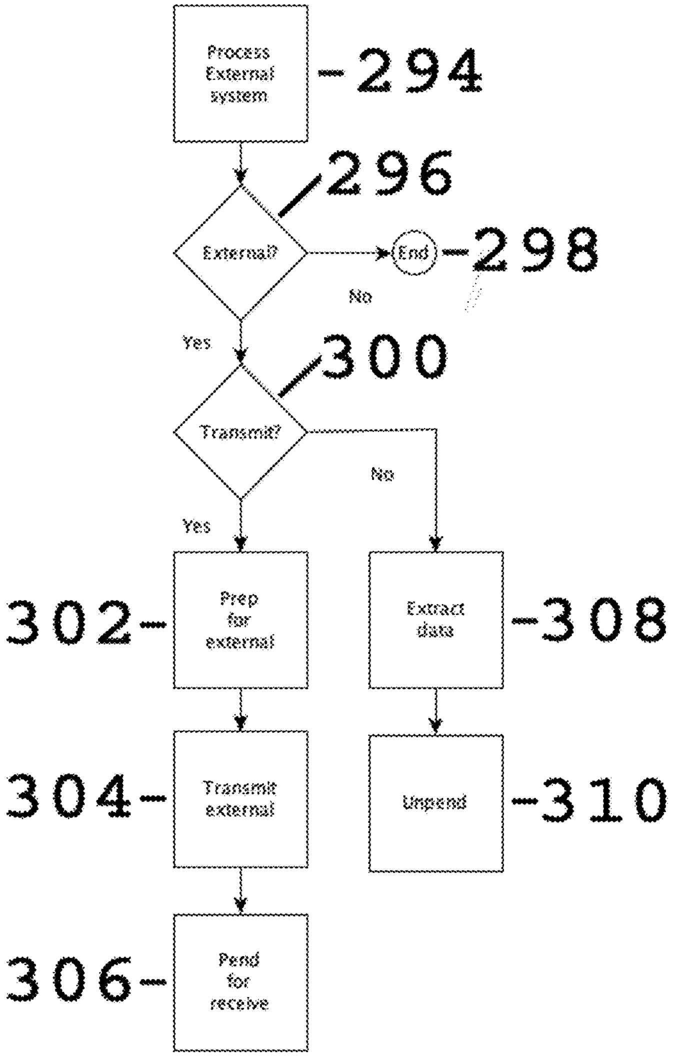
FIG. 10 is a flow chart showing a process external system of one embodiment of the present invention.

FIG. 10 shows the processing of an external system 294. If the chain step requires processing an external system at external query 296, the system proceeds forward with processing the external system. Otherwise, the process external system ends at end 298.

If the chain step requires processing an external system, the system determines whether the chain step requires transmission of data or other information at transmit query 300. If data or other information is to be transmitted, the system prepares for external processing 302, transmits the external data and/or other information 304, and waits for receipt of data and/or other information from the external processing if such data and or information is to be received at pend for receive 306.

If data or other information is not to be transmitted at transmit query 300, the system waits for the data to be received if data is to be received. The system then extracts the data at extract data 308 and upends the chain step for receive at unpend 310.

Figure 11:
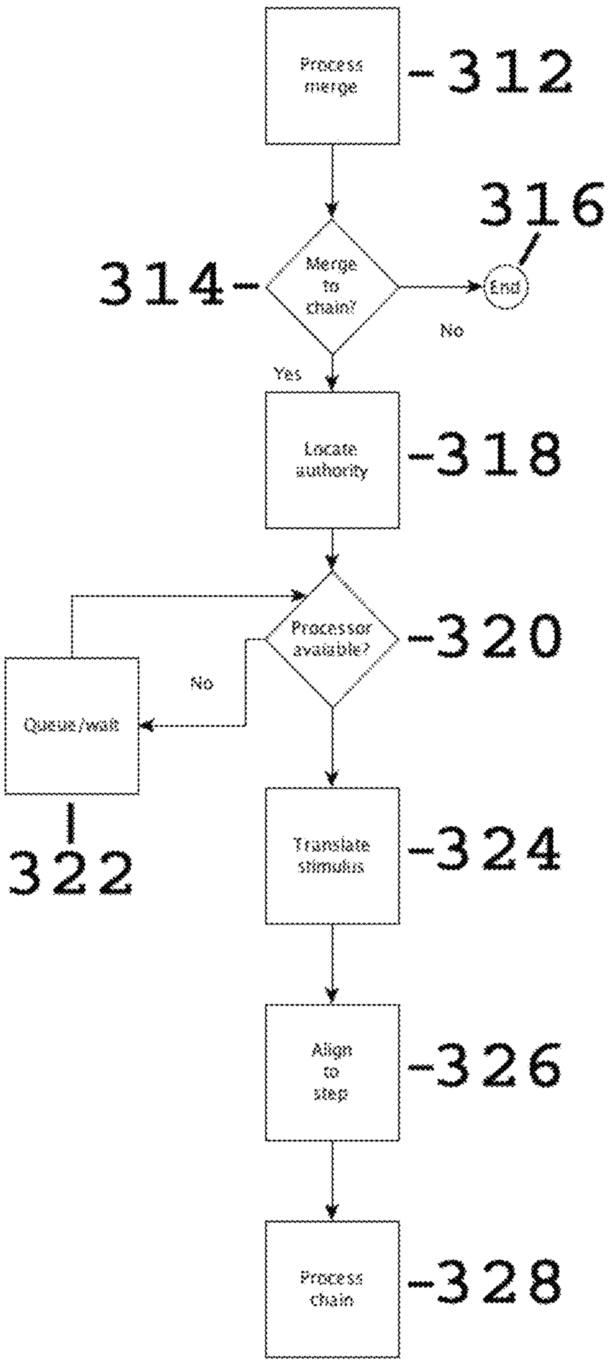
FIG. 11 is a flow chart showing a process merge of one embodiment of the present invention.

FIG. 11 shows the process merge 312 of one embodiment of the present invention. If the process is merged to the chain at merge query 314, the system locates authority at locate authority 318. If the process is not merged to chain, the process merge ends 316. The system locates authority by checking the authority of the user(s). As described above, the system checks the authority identifiers such as the nation identifier 102, region identifier 104, community identifier 106, facility identifier 108, the department identifier 110, the responsibility identifier 112, the group identifier 114, and/or the user identifier 116. As described above, the processing of the chain 98 and chain step 100 continues when the processor is available at 320. The processing of the chain enters a queue and/or waits 322 until the processor is available. As described above, the system translates the stimulus 324, aligns to step 326, and processes the chain 328.

Figure 12:
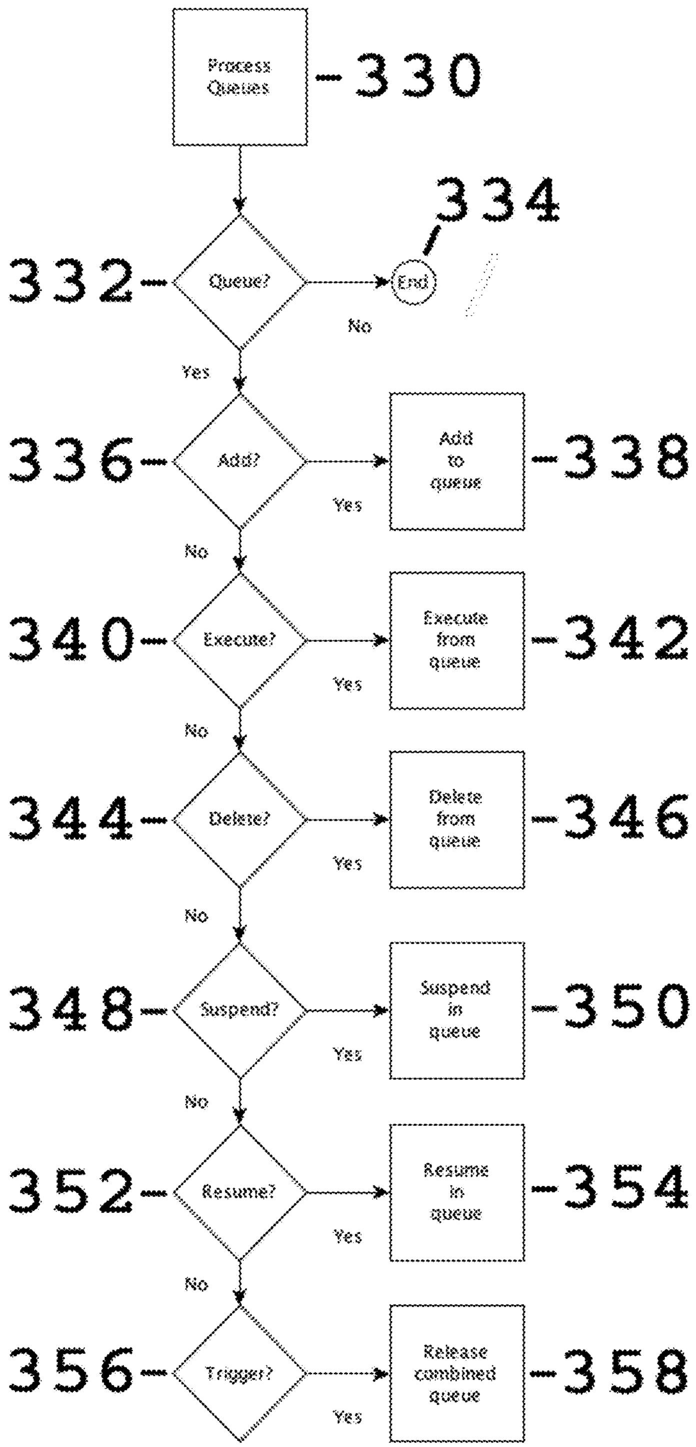
FIG. 12 is a flow chart showing process queues of one embodiment the present invention.

FIG. 12 shows the process of queues. If the queue is empty at queue query 332, the system stops processing the queue at end 334. Otherwise, the system processes the queue. The chain steps 100, the events, stimulus, and other processes may add items to the queue to be processed. The system checks whether an item should be added to the queue at add query 336 and adds to the queue at add 338 if appropriate. The system checks whether an item should be executed from the queue at execute query 340 and executes from the queue at execute 342. The system checks whether an item should be deleted from the queue at delete query 344 and deletes from the queue at delete 346. The system checks whether queue should be suspended at suspend query 348 and suspends the queue at suspend 350. The system checks whether the queue should be resumed at resume query 352 and resumes the queue at resume 354.

In one embodiment, the system checks whether a Trigger should release the combined queue for continued processing of the chain. In one embodiment, chains may be placed into a queue for processing. Chains may be placed into a queue because the system requires information, data, or some other action before the remaining chain steps can be processed. The queue continues to collect more processed chain steps until a trigger is detected. Detection of the trigger causes the system to process the steps that have been placed in the queue. In one embodiment, the trigger may release the pent-up queue. For example, they system may require collection of enough of the medical record to release to the hospital's coding department for billing. Triggers may affect the processing of other chains, chain steps, and activities to be performed by the system.

Figure 13:
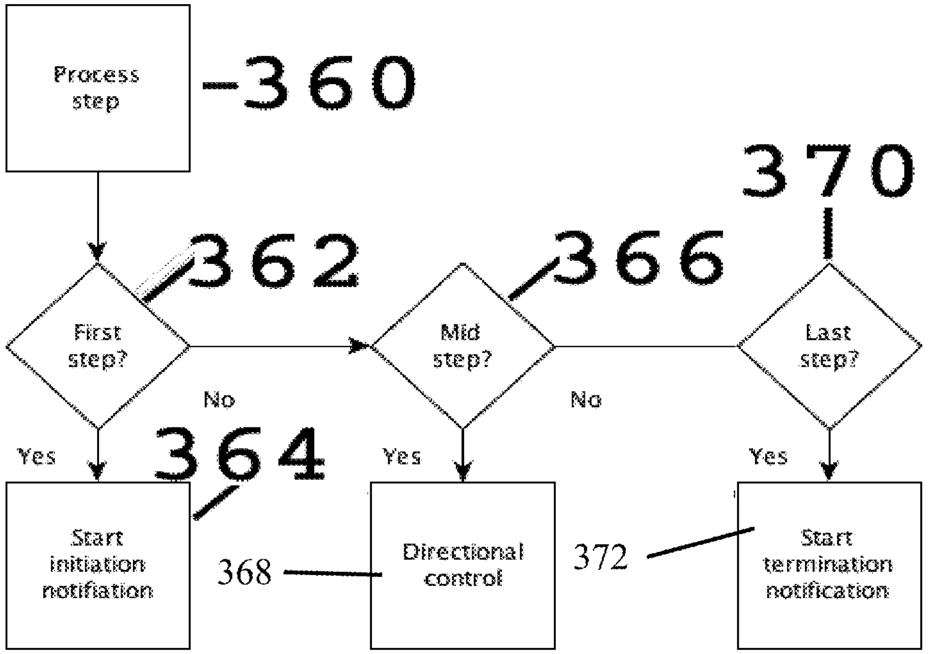
FIG. 13 is a flow chart showing a process step of one embodiment of the present invention.

FIG. 13 shows process step 366 for processing chain step 100. At first step query 362, the system determines if the current chain step 100 is the first step. If the chain step 100 is the first step, the system starts initiation notification 364. The chain processor indicates via an event that a chain has started allowing other processes to be activated. The initiation notification may directly or indirectly activate the processes. The initiation notification may also activate fixed processes (or skills) available in other supporting technologies. If the current step 100 is not the first step or the last step, the system allows directional control of the steps of the chain 98. The chain can move forward or backwards depending on the directional control 368. If the current chain step 98 is the last step 370, the system starts the termination notification 372. The termination notification enables the chain processor to indicate via an event that a chain has completed allowing other processes to be indirectly activated.

Figure 14:
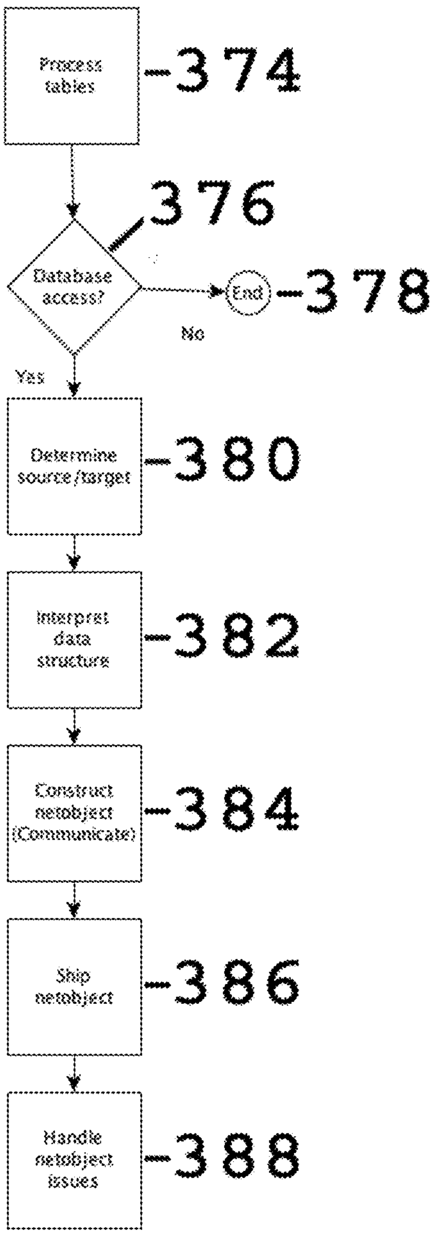
FIG. 14 is a flow chart showing process tables of one embodiment of the present invention.

FIG. 14 shows process tables 374. If database access is available at database access query 376, the system determines the source database and/or target database at determine source/target 380. If database access is not required at database query 376, the process tables ends 378.

The system interprets the data structure 382 to identify the source/target so that the data and/or other information may be properly accessed, updated, modified, deleted, and/or inserted. The system constructs a netobject 384 to construct a netobject so that the data may be accessed across multiple systems. The system then ships the netobject or receives the netobject at 386. The system then handles any netobject issues at handle netobject issues 388.

Transaction GUI—Look-up machinery—The authority action and reason are queried from the database as the user types. The possible permutations of authority actions and reasons, as well as their permutations, are stored in separate sets of tables. The look-up methods and classes are shared between the sets of tables by supplying a parameter that indicates which set. Tables for authority actions include procedures, drugs, items, services (includes consults), user defined action translations (doctor's version of a procedure) and the permutations table. The table set for the authority reasons appears to require less diversity. New tables for either may be discovered as the system matures. It is also possible that another set of look up tables may at some time be implemented (although what it would be is unknown as of this writing).

Preferences:

Users can alter the layout of the screen by simply dragging objects from one place to another, and the system will reproduce the altered layout each time the user logs in.

FIG. 15 provides additional information concerning Reasoning Chains.

Reasoning Chains:

Users can record a series of changes in the screen layout and the presentation of data. The data can then be presented in the best possible way for consecutive steps of a process.

For example, a physician has a tendency to look at the same sequence of places in paper records for the same diagnostic though process.

The user can save the sequences under an assigned name, loading each for the appropriate review process. The user then clicks a single button repetitively and the system will constantly reorder the presentation to match the user's review process.

The user may save the sequence of reviewing data on the screen. The user may position the data in the desired location. The system will then store the location of where the data is located. The system will also store the display size of the data so that the user's preferences will be saved. The system will associate the data location and the display size of the data with the user. Because some information will not be needed by a user, the user may indicate which data to be displayed. The system will indicate which data to be displayed and display the data to be displayed at the location and size indicated by the user's preferences.

Because the users may require different information depending on the type of user, the data to be displayed, the data location, data size may vary depending upon the type of user. Each user may specify the individual user's preferences. In one embodiment, the viewing preference may be designated by a hierarchy of the nation id 102, region id 104, community id 106, facility id 108, department id 110, responsibility id 112, group id 114, and user id 116. The system checks for viewing preferences in the most specific category. For example, the system checks for user id 116 associated with the viewing preference. If no viewing preference exists for the user id 116, the system will check the next higher level, group id 114, until it finds a viewing preference for data.

User experience—Doctors must be able to save and re-use an order with its procedure, diagnosis and detail. The selection of a saved order is integrated with the dynamic selections made available by the permutations generator.

One embodiment apprises users about the available procedures or diagnosis that match a selected diagnosis or procedure (respectively). Only certain diagnoses belong to a given procedure and vice versa. Physicians strongly resist systems which force actions into a narrow set of options. The system guides decision making to help the physician gain the desired values.

The transaction process will store each combination of diagnosis, procedures and other details and rank them by frequency of use. The higher frequency items may be listed in higher priority than the lesser used on a selection list.

The user experience includes automatic prompting of possible selections based on the generated permutations, historical frequency of use and custom descriptions. By default, the user always has access to the system generated descriptions and defined descriptions that are set to public accessibility. Some custom descriptions, re-usable saved orders and selection by frequency of use are specific to a geo-location key.

The system examines the code associated with each phrase combination looking for commonality. The list of available permutations automatically collapses to the proper description when it is clear that the lines are duplicate references to the same code.

The effect of automatic reduction will appear as a "smart" process which finds the correct code/description when the user enters a similar code description.

Options include generating permutations, maintaining a single permeation set, ascribing a known code to a dynamically specified description from a user. Some of the functions may need to be triggered by events. For example, a physician may enter an unknown code/description. An admissions person may then receive the physician's permission to associate the description with a known code/description.

Permutation generation is housed in a special panel and can stand apart from real-time processing. Assigning relationships between user-defined descriptions and known codes may be accessed from the chain step screen. The two examples show different capabilities which may not be available to the same users.

For example, the admissions person receives an order with an unknown description. The admissions person makes an assumption as to which known description it may be related. The system returns the transaction to the originator showing the assumption of the relationship. The originator confirms the relationship between assumption and the known description and the order processes, in effect, from the start of the chain. Otherwise, the originator indicates the proper relationship. The relationship between the assumption and the known description is added to the table and is known from that point forward for that provider.

Another example would have a normal maintenance like sub-panel prompt for the relationship. The administrative person may contact the doctor to receive his direction and approval. In this example, the system would capture a reference indicating how the user gained the doctor's direction and approval.

Handling conflicts and counter indications can be supported by real-time guides, but will be best served by batch-like system responses. The responses will be all grouped together in a list that displays in a scrolling text box. Significant warnings are handled with some special emphasis.

1. Summary of user interface lookup features
2. Random lookup based on permuted descriptions
3. Save and use orders as re-usable models
4. User defined descriptions
5. General or shared selection options
6. User specific selection options
7. Selection option priority based on historical selections Documentation—Permutation generation automatically creates variations of a procedure or diagnosis descriptions. A given description is parsed for its constituent words and a set of new descriptions are generated for each possible organization of the source phrase. Only words that are medically significant are included in the permutations. Common words may be ignored and not included in any of the generated variations. Abbreviations are translated into meaningful words, which can be included in permutation generation.

Source tables define the words that are to be excluded from generation or to be replaced with a translation. Complete source entries can be excluded based on containing a word or phrase, such as "no longer used". Word case is set to lower case including the first letter in names. Consistent case makes search and matching easier. Generated permutations work in conduction with user specific custom descriptions and re-useable saved orders.

Data import source—Data sources are supplied collections of data usually packaged as a text file. The file contains codes and related descriptions that can be loaded into the C-EMR system as things to order or reasons for an order. For example, a thing to order may be a procedure and then the reason would be a diagnosis.

Description—Source files are described by the target data. The description comes from the system target word definition which must exist to allow a file to be imported. Descriptions are intended to inform the purpose of the import, in effect, the kind of data that will be targeted, such as ICD-10 codes and their descriptions. The descriptions are user defined. In one embodiment, the descriptions are not included with the source file. The same definition process that makes a kind of file available also specifies how to extract the needed information from each of the lines in in that source file. The context in which the information is expected to be used is also specified.

Source file—Each source file is pre-defined in the system permutations targets including the expected name of the file. Actual file names may vary and can be altered at import time by editing the file name directly. Sources of information have a tendency to name files in a consistent manor where the contents of the file and version are referenced in the name. For example the United State federal government provides data from their H-CUP website for the ICD 10 codes specified by the World Health Organization. The source references "Clinical Classification Software (CSS) for ICD-10" and the file name is "ccs_icd10_2006.csv".

File extension—Text files have trailing identifiers, called extensions that indicate the formatting of the data within the file. Some operating systems rely exclusively on extensions to determine how to read a file. While most actually look inside the file and determine how it is formatted. Operating systems from Microsoft® rely on the extension, while Unix®, Linux and OSX® look inside the file. The extension is maintained for the sake of compatibility between systems. Some common examples are:

.csv Comma Separated Values (tabular data)

.txt Text (free form)

.dsv Delimiter Separated Values (tabular data)

Most files cannot be imported without a pre-processor because they have unformatted data. Files must have a method of identifying what the data means, in effect, data that describes the data. This kind of data is called "metadata" and usually is at the beginning of an importable text file. Files that do not contain metadata or contain random kinds of data include;

.pdf Portable Document Format (free form text and images)

.html Hyper Text Markup Language (free form text and layout code)

Context—Contexts represent why a specific process wants to access a given data store. The context system allows software to find needed data without having to know where or how it is stored. Normal databases and their structure are called an external context. The understanding needed by an application to gain access to data is called an internal context. Each data element is automatically mapped for type, structure and other characteristics which are translated to a like set for other database elements that are substantially similar or are for the same purpose.

Users can map translations and override names as needed. The relationship between internal to external contexts is not a rigid one-to-one direct connection. Internal contexts do not have to abide by the rules of a database of the structure of tables within. Multiple internal contexts may reference the same data in the actual database. Another way to look at contexts is that the external context represents where the data lives and how to gain access. Internal contexts are not concerned with the physical mechanics of database access. Internal contexts can be thought of as "why" and "when" an application needs to gain access to the data. The three values that are needed to identify a context have no meaning by themselves. Only the combination of the three values creates a reference to information. The values may be named for convenience.

The user may want to know something about an employee but only in terms of annual reviews and the costs of operating a business. In context, the user may reference the need to know about an employee in respect to personnel and the controls of a business. The context would then be employee, personnel and accounting.

Field—The name of the target element of data within the target of the permutations generator. The data element is that place into which the generated permutations are to be saved. In most cases it is expected that the target is the same from file to file. The ability to define a target data location is included to allow support for other targets which may need to use the permutations generator.

Code column—The column number from which the system is to extract the reference code. The reference code is a constant value that various generated permutations will be translated. The code represents a commonly accepted identification for a process or description, for example diagnosis and procedures. Column number is that column position in the source file being imported where the first column from the left is 1, the second is 2, and so on. Count the columns (starting with 1) by counting the definitions for each column documented in the first line of the source file (assumes .csv file format).

Data column—The column number from which the descriptions are to be parsed into various permutations. Find the column containing the description associated with the code on a given line in the source import file. The description usually has a set of words which may or may not be in a natural order. Different users may reference the same code using differing combinations of the descriptive words. In some cases the user will only know or expect one of the words and will need the system to help locate the best collection of words.

The located description may not be in a natural order for speech. Each possible code may have multiple descriptive phrases where the most significant words are listed in different orders. The orders align with the priority a particular person may apply to the set of possible words. The generated permutations allow different users to assume different priorities for the possible words associated with a known code. The system automatically generates a complete set of the same words ordered in different priorities.

Compress—Should the import process skip parent entries including only the payload (last child) lines? (Eliminates the more general lines in favor of only the more specific). Some source files will have a single line representing each code while others will have a hierarchy of descriptions. In these cases, the codes are defined from the general to the specific. Starting with the first character or characters which repeat for a section of codes. The repeating section is defined once with the greater detail listed afterwards. For example:

001 very general 00101 more specific 00101-001 refined specificity

Data is organized in an inverted tree where the actual coded definitions are represented only at the terminating leaves. Compression skips all of the non-leaf values and generates permutations only for the usable leaves. The result is a collection of codes that are accessed directly and usable as found. Files where there is one entry for each code do not need to be compressed.

Delimiter—Character or characters that indicate the boundary between columns of data in the source import file.

Quote marks are usually not referenced when determining the column boundaries. In tab and comma separated files, quotes distinguish between a column containing only numbers and columns containing a more random assortment of keyboard characters. The following comma separated file fragment shows the metadata on the first line (data that describes data). Values start on the second line and quotes are omitted when the value is expected to only be numeric:

"person_id", "name", "address", "age", "balance", "last_transaction"

"0001", "Gary", 43, 230.00, "2010 May 02"

"0002", "Fred", 22, 00.00, "2010 May 03"

Spaces have been added after each comma to make the data easier to read. You can see that Gary is 43 years old and owes $230. Notice the lack of quotes on the actual age and balance values.

Parsing—The system will read the first line of the source file and assume that the name and number of the columns is defined by the values. It will be assumed that each of the lines will contain the same number of data columns.

Delimiter types—Comma and tab are the most common and usually adhere to the structure described above. Space is unique because it tells the system to separate each and every word into different columns. In this form quotes are usually non-existent or ignored. Be aware that line feed (LF) and form feed (FF) characters will cause the source file to display poorly. Their use is rare, but may be encountered.

GUI Experience—The user starts to type either an authority action or reason. In a perfect world the user would be able to start with either the action or the reason and then have the system help find the other. For example only a known sub-set of possible diagnosis can be associated with a procedure and vice versa.

For the purposes of this discussion, assume the authority transaction starts with a procedure. The user types into the action field. The display shows a list of possible options. System definable "parameters" define the number of characters to be typed before automatic look-up displays the corresponding selection, the number of items displayed at one time and the number of identical characters that must be entered to show type-ahead. For example, if the number of characters that must be typed is 4 then the system would lay quiescent as the user types the first 3 letters. The list of options will then start to display after the user types the 4th character. Likewise, the list will be 20 items long if the items to be displayed are defined as 20.

The system presents additional characters (highlighted blue) as "type ahead" to the right of the curser when it is known that there are no additional options. For example, assuming a listing of 20 possibilities where each one the first 19 start with "chronic" after the user has typed "chr". Since the last one is different (say it starts with "chu") then the balance of the word ("onic") displays to the right of the curser (in this case including the space). The user presses the right arrow or clicks to accept the type ahead or just keeps typing. The evaluation of identical words could extend beyond the displayed list when there are buffered items known to be contiguous with the displayed list.

The process repeats as the user continues to type whenever the next n number of characters is known to be the same from selection line to line.

Current implementation of permutations generator and search support.

Physician Orders (Physician Directives)—Physician orders are line item centric. In fact some people mix the words for line items and order where each of the line items in an order, are simply referred to as an "order". Physicians customarily issue a set of directives which represent tasks to be performed in a variety of departments and facilities. The system supports the creation of a set of directives (for example a physician order) where each of the items in the set do not have to be related.

The system automatically determines to which departments and facilities any one of the items is to be sent. For example, a physician may order a procedure which requires a stay in the hospital, various tests on the patient's blood, an x-ray, a few drugs and a surgeon. In the example set of directives, the system would automatically start authority chains for lab work, radiology and admissions and the surgery consult.

The CEMR system groups line items into orders. The word "order" in the system, refers to a collection of one or more order items. Each order in the collection is referred to as an order line item or line item detail. Orders can be split, replaced, extended, or otherwise modified. It is possible for a line item in a new order to take the place of a line item in an earlier order while other line items in the same order are not related to the old order, only the new.

Reasons for Sharing Authority—

There are a finite number of reasons that a patient can be referenced by more than one provider. Under modern conditions, each of these reasons has in common a transaction-like process which implies the authority.

The CEMR system institutionalizes the reasons and provides a standardized platform for authority driven patient record access. The reasons all have the transaction-like requirement in common, but vary in how the transaction relates to the patient.

It is generally assumed that physician orders start when a physician chooses a course of action and end when that action is performed.

However, the physician directives and orders can traverse multiple steps and departments and then generate requests for more information or results. In fact the "order" starts at the time the patient first presents and includes all of the events that take place as it is processed and then the ones that take place as a by-product of being processed.

For example, a relay of a physician order to a hospital pharmacy is generated to tell the floor nurse that a drug has to be administered. The action of filling the prescription and administering the medications are extensions of the original order. So too are the confirmation notifications from the pharmacy (ready to pick up and delivered) and the ones from the floor nurse, in the example.

At first it may then appear that the paper trail following a physician order must eventually terminate the point and person of origination. That too can be exceeded when the provider takes additional actions as a direct reaction to returned results.

In our examples above the authority needed to see specific medical information followed the patient from one service to the next. Which bits of information became visible at each step is dependent on the area of expertise at that step in the work-flow. For example the pharmacy or radiology or the collections person in a physician office all need to see different sub-sets without having access to all.

Vehicles for Sharing Authority—

Each of the following example reasons for sharing medical information have analog methods in which that information is shared. The reasons and vehicles include these examples:

1. Physician orders
2. Patient transfers
3. Referrals

4. Consults
5. Admissions/Clinic sign-in
6. Provider transfers (changing provider)
7. Simple send or request for access authority All of the reasons and vehicles for sharing authority can be represented as a transaction. The reasons and vehicles can be represented by the same kind of transaction. The only differences are the level of skill and location of the originator and the places the transaction stops and then terminates. Placing a physician order to a department in a hospital can stop at hospital admissions, one or more departments, the floor and then coding. At each step a reverse transaction may be generated as a result of a problem or a result.

Requesting a referral follows similar steps through a work-flow that stops at different locations and skills. The referral request is a transaction that must leave a paper trail and provide authority to access patient records. The transaction may stop at the front desk of a clinic (admissions) and then on to a specific person. The step at which the referral moves past the front desk should result in some form of returned acknowledgment. All followed by an acceptance or rejection of the request and eventually the results of the patient visit.

Both examples could be viewed as "orders" or a transaction similar to an order. In the CEMR system, these transactions may be referred to as "Authority Transactions".

Linkage between patient records in disparate systems—The CEMR system uses the same transfer mechanism for all of the authority transactions. The transport has the ability to track and move transactions through a dynamic list of steps and stops.

All transactions of all types have to first resolve patient alignment between disparate sources of medical information, referred to as alignment. Alignment uses known linkages between different sources. In addition, the option to resolve additional information sources is made available when a patient presents. The system eliminates the need to blindly search systems for possible matches to patient records in other systems. The transfer or sharing of authority provides a reliable and consistent method of resolving alignments. Any given facility has a set of patient records for the patient—if not new ones are created as of that visit. The need to see records in other facilities comes when the patient visits a facility with a different computer system.

In some cases, the existing linkages suffice. Other cases require additional information. There is a natural flow to the need to know. A physician needs to know the medical history of a patient that has been referred. The referral process automatically relates the patient between the two facilities (the referring and the referred). The check-in process makes permanent the linkage between sets of medical information in different computers. The new history collected during the patient visit is then automatically available to the referring physician who also needs to know.

Accessing Medical Records—

In the case of referrals and consults, the patient information can precede the patient. The referred facility can align the incoming patient record with local ones with the help of the patient when he or she presents. The alignment is a linkage between the records in the two disparate systems which is now available when the same patient visits yet another facility. Patient records are aligned as a natural by-product of the normal ebb and flow of patients.

Some transactions may go only one step. For example, a patient "event" is a transaction that is an instance of the patient at a specific point in time and at a specific location. The transaction is created at the time the patient checks-in. The receiving staff (such as reception at a small facility or admissions in a hospital) identifies the patient and matches the patient to any records currently available in that facility. All of the transactions of one embodiment must proceed through that process.

Examine the case of a single step sharing of authority, for example a simple patient visit. The transaction starts with the patient. Alignment of the real physical patient to known medical records also takes place (such as the local facility or shared information).

The CEMR system then presents the caregiver, such as the physician, with an automated list of only those patients that are ready to be seen. In effect, the check-in process has generated a transaction that simply becomes a member of the list. The attending clicks on a specific patient item on the list and the correct and complete medical record for that patient. The act of seeing that patient is also a step in the transaction process. The listed item should now be showing, not as ready to see a physician, but as now being seen. The transaction has progressed to another step. The patient is then checked-out, but that does not close the transaction. The physician must complete recording of the medical record.

Flow of Authority—

The following graphic depicts a unified view of the flow of authority. This is the general path that authority takes in any form of information sharing. The objects highlighted in yellow are examples of authority transactions (the stack highlighted between B and C of FIG. 16 and how they would fit in the authority chain's work flow. FIG. 16 shows example forms of authority. Key to the parts of FIG. 16:

A) Incoming authority transaction
B) Intra-facility authority transaction
C) Transfer or Share of authority transaction
D) Steps in the flow of authority transactions
E) Specific definitions for the flow of each kind of authority transaction
F) Outgoing authority transaction
G) Automatic sources of information for an authority transaction
H) Direct translations from provider specific terminology to industry standard coding A) Incoming authority transaction shows an authority transaction that is coming from another facility. Traditionally this would include giving a copy of medical information to another provider for a consult or referral Indeed may providers still think in terms of "transferring" or "copying" medical records. Using the technology, it is only necessary to share the authority, which in turn, grants direct access to stored medical information.

This form of authority transaction is likely to require both patient identification (Identify actual person and alignment with local records) and community linkages. The linkage between the facility sending the transaction and the one receiving the transaction may or may not already exist. If the linkage exists, the receiving facility will automatically be granted access to the records from the sending facility per the authority transaction. If not, then the receiving facility will identify the patient and match any local records to the incoming authority transaction to create the linkage and to grant access to the medical records at the sending facility.

B) Intra-facility authority transaction—Authority may be shared within a facility. The person receiving the authority may be the only professional to view the records. For example, check-in a patient, get the records and hand the records to the doctor in a paper system. This form of authority can persist until all of the service and related record recording is completed. It is also possible that authority goes to another person in the same facility. Think in terms of a simple check-out process in a clinic. It is customary for the patient to carry a piece of paper listing the procedures and possibly the diagnosis to the front desk. The person at the front desk is receiving authority to see at least that much of the medical record. It is another step for an authority transaction.

C) Transfer or Share of authority transaction—Transferring and sharing authority are transactions that give access to another medical provider, which may or may not be in another facility. Transfer of authority is similar to consults. The patient requests that his or her medical records are sent to another physician, such as when a patient changes primary care givers (e.g. moves to another town). Sharing is when the medical record file is to stay active while allowing another provider to serve as primary for example, when one physician is on call for another.

D) Steps in the flow of authority transactions define the steps for targets (list of possible steps for each kind of authority transaction). Central definitions that standardize and define the possible steps may be used in any of the paths of the various kinds of authority transactions, for example, Clinic, to admissions, to radiology.

E) Specific definitions for each kind of authority transaction include matrices that determine which of the steps and what actions are to be taken along the way for a given type of authority transaction. The steps for any facility and the departments within can be customized by establishing the steps and actions in the matrix.

F) Outgoing authority transaction shows Authority transaction going to another facility. Traditionally, a patient would be given a document to carry to the other facility. The doctors may spend a moment on the phone or a fax may be sent or requested. In each of these cases there is an explicit grant of authority to medical information. As described above, an authority transaction may be sent to another facility. The originating facility is providing some form of paper trail (audit trail) documenting and providing access to medical information.

G) Automatic sources of information—Various sources of information can automatically be added to the authority transaction. System tables containing information for the user, provider and the patient are all used to fill in as many elements of data as possible. There are other tables, which include definitions for the facilities and departments expected to receive the authority transaction. An authority transaction can contain nearly 100 elements of data, yet it is possible to create and send a transaction with less than 10 entered or selected values.

H) Direct translations from provider specific terminology

Physician Personalization—

The CEMR system supports automatic translation from the words used by one physician to another or in relation to industry standard codes. The entity maintaining the CEMR implementation has the ability to receive authority transactions with the words the originating provider prefers or has a habit of using. The receiving staffer may correspond with the originating provider to correct the wording. For example, admissions staff for outpatient radiology in a hospital may have to correspond with the physician to get a physician order fixed for processing (which may delay service reducing the patient satisfaction with the institution).

Principal item descriptions in transactions can be automatically corrected so that providers are not required to change habits and practices. Such automatic correction allows the receiving facility to avoid constantly correcting transactions (i.e. physician orders). Translation is optional. The provider can elect to start using the terms or codes expected by the receiving facility by simply using them (no changes are required).

Reasoning chains—The user interface has a great deal of flexibility in the order and position of information displayed. Information is divided into topics based on the kind of information, including but not limited to allergies or diagnostic history. Topics can be viewed individually and separately. For example topics may include patient demographics, allergies, drug, diagnostic, procedure, vaccination and other histories as well as insurance information. The order of topics on the screen, which topics are open, the sort order of the data as well as the position of the columns of data are all adjustable according to the user's customization.

The system has the ability to set user preferences for the order of topics and the order of information within a topic. The prescribed order is always the initial display for the same user. Users navigate the information to answer questions. The order in which the questions are asked tends to follow a pattern. Questions are answered by selecting and organizing topics, ordering the information contained within the topic and positioning columns of information to gain the best and fastest access to the resultant answer. The variable nature of the system user interface allows for easy access to answers. Information can easily be reordered or reorganized with just a few mouse clicks.

Chains of reasoning take the preference capability to the next level by providing automated access to a series of preferences. Each combined user interface organization is intended to answer specific questions. The user would manually make such changes as the need arises. Reasoning chains consist of one or more steps where each step is a complete definition of how the data is expected to be ordered and displayed. With a single mouse click, the user can step through the chain and the entirety of dynamic settings.

For example, a collection of steps to answer a question about how a patient has experienced labs might include moving the labs topic to the top of the page, opening the topic, ordering the information by date and lab, and then moving the lab test panel column to the far left. The example is a simple chain of reasoning. Complex chains can continue the process answering a collection of questions in a predictable order. Chains are a recording of user actions that change the appearance of the display. The actions are traversable allowing the user to roll backwards and forwards through the recorded changes to the display. Examples include opening a topic. The history methodology records and allows the playback of changes the user makes in the appearance of the display.

Preference—Preference objects define a one-to-one relationship between a given user and reproducible state of the system. A user has a defined Logon object in which a given user can have many Preference objects. Preferences are typically named for the topic for which the preferences are to be reestablished each time the same user revisits the same part of the system.

Requests for a given set of preferences are made by a matched pair of names for example; get(objectName,preferenceName) from the PreferenceSet object. A single PreferenceSet Object is constructed at user logon time. The PreferenceSet Object represents a single user and can contain many preferences. The preference is known by the combination of the user and the Preference name. In one embodiment, only one preference set object is constructed at a time. The PreferenceSet Object is carried throughout the system during a user session.

Preference settings are accessed by a preference id that is human readable as the name of the preference. Preferences are loaded at session start. Preferences are set by manipulating the target GUI control for which the preferences to be set. Changes to the stored version of the preferences by a different program or session may be lost if the user acts to change a preference. For example, moving a topic dialog to another position in the topics list would be recorded in the preferences table. Each new preference change replaces the one currently stored in the database. Changes are applied (saved to the database) at session end and loaded at session start. Optionally, it may be possible to save session preferences to the database in real-time. That is, each time the user changes the display a commensurate recorded value is sent to the database. Session preference changes would be saved in the event of system failure. Real-time session preference recording is very expensive on network overhead. Therefore, real-time session preference recording should only be used when loss of display preferences would pose a significant risk or interruption.

Preferences consist of an identifier used to recall a given stored preference and a set of values. Preferences are different from options or other dynamic settings. Each of the preferences is created and saved by the same program that applies the preference values. Programs and process are not intended to share preferences. Users of one embodiment are not expected to share the same preferences with other users. A preference is unique to an object within a specific program and to a specific user. The same user accessing the system from any location will have the same preferences applied to the session.

The programming that generated a preference Object should be capable of interpreting the values stored within. The preference setting is recorded within the preference Object as free-form information. Preferences only have meaning or are applicable when the assumptions made by the originating program are taken into account. Values are stored within Objects of this type as generic String message. The message is standard to the system and can be automatically converted into a variety of array formats. Conversely, free flowing text or values can also be stored.

Naming Preferences—

Preferences require two values to be identified. The first is intended to specify the environment (class, event or other object) to which the Preference is to be related. The second value is the kind of preference for that object. This allows for multiple kinds of Preferences for the same event or object.

For example, in the help editor the size and location of the pop-up window is stored when a logged on user changes the window position or size. The word "Window" is used as part of the name buildWindowPreferences and findWindowPreference respectively.

Topic Interpreter—Interpreted programs are called topics. Each topic represents a specific area of information usually associated with a primary database table. There need only be one actual program which is the interpreter. The programs that the user sees and interacts with are simply data models behaving like programs via the topic interpreter.

Topics can be grouped into commonly needed data for a specific kind of user. The groups are called user groups which are defined in the access_group table. Topics can belong to many groups. In one embodiment, users belong to one group.

Programs are defined in two tables, one that defines the existence of the program and the other that defines the behavior of the program, topic_specs and topic_specs_objects respectively.

The interpreter runs from the main CEMR program class which houses the various topic instances. Collections of topics are displayed in vertical alignment as single topic bars with a graphical arrow (triangle) and the name of the topic. Help may be attached to the topic description.

Clicking on the array "opens" and "closes" the topic as a screen region on the topic bar. Data is organized in rows and column in spreadsheet like fashion. The initial arrangement of the columns and which data elements from the database table display are defined in the topic_spec_objects as initial order. The column order can be changed by the user by simply dragging the column header to a new location along the horizontal axis. The new positions are stored as preferences which are automatically reapplied each time the user logs in.

Preferences for sort order column order and column widths are available and automatic. The same is true for the order of topics on the main display and help dialogs.

A single entry in the topic specs table defines the existence of a program. Entries are added to the topic specs objects table to add usable data, display and logic. Adding the program to the list access_topic table for a given user group makes it available. Available programs all display on the main screen in the order specified, first by the access topic which may be overridden by the preference system. Advanced features are automatically available in the defined topic program without any requirement for definition.

Topics are defined as collections of object specifications where each defined object reflects a data element. The spec can be displayed or not depending on other needs as the program is defined. The order of the specs is not relevant to the display, but it is relevant to the processing of data. Object specs with lower positions in the order are processed before those with higher numbers. This can be important when adding logic or defaults.

A variety of data sources are available to the topic program at run-time, including, Data from the database, in-memory, operating system run-time and user defined variables Reasoning chains allow the user to create operational protocols which change the presentation of information by moving and opening topics and relocating display columns, chain their width or sort order. The changes to the display are automatically applied each time the user clicks on a single "next" icon. Reasoning chains provide a way to operate and navigate the system automatically. Each click of the same icon makes a single step in the reasoning chain which adjusts the display and data accordingly.

Topic programs can be maintained via a topic program called Topic Program Maintenance, which addresses the definition of the spec objects. The most common way to create and maintain the topics is through the initial load SQL script.

Topic bars are instantiated for each topic as straightforward TopicBar objects. Topics, however, require a unique Topic class which extends the Topic Object. Topic bars control access to a given topic. Topic bars allow topics to be shown, hidden or moved in the display order. Hiding and showing may be controlled by an arrow on the left side of the topic bar. Clicking on the arrow changes the show/hide state and alters the arrow. The arrow points to right when the topic is hidden and points down when the topic is showing.

Changing the display order of the topics is controlled by a mouse drag gesture started on the display test showing in the topic bar. Topic bars are dragged up and down the screen. Releasing the mouse when another topic is indicating mouse focus will reposition the topic bar being dragged to that slot.

Litigation support is in the form of "snap-shots" which are recorded copies of patient information frozen in time as available when the medical provider reviewed the patient record. The system automatically takes snap shots of only those topics which are medically relevant based on the topic program snap shot switch in the topic spec definition.

Topic Definition—Programs are interpreted by the sequence number. The order in which columns are populated is controlled by a specification of column position. Logic can set a value into another column or collect values from other columns.

Each row in the topic_specs_objects table represents a single programmatic step. The steps are executed in sequence as specified by the process_order field. Interpreted programs have a wide range of data sources including system and user defined variables, table columns and literal values. It is important to note the order of processing because data may not yet be available. Examples include using data from a table column that will be processed by a later program step.

Sources of Data and Priorities—

Table cells can be populated by more than one source. The following shows the order of priority that will arbitrate when there is more than one data source:

- Default values that are general to the system have the lowest priority
- Values include those that come from the host web page, logon information or the system date.
- Generic system values include those that translate using the form @name and literals
- Repeating items have priority over defaults
- Values that are duplicated from the previous row replace (assuming that there is a previous row) generic defaults
- Default values that are topic specific have priority over repeating values
- Values which are only available in the current topic have priority over repeating values for example; the name of a drug. Topic specific values are derived from table fields or database record
- Values that are the result of logic have priority over topic specific defaults
- The fact that the value arrived via logic has greater priority than any specific data source. Values from any source that are delivered by logic have the highest priority Including Variables—

Data from the table is assumed to be from the CURRENT line being processed. New variables established when the interpreted program is running can be set and updated at any time.

Special characters are required for pre-defined CEMR and user defined variables, use leading @ and ? respectively. Values within the system may also be available.

1. For example a table column or java program variable. System variables must lead with the hash sign ("#").
2. For example a table column with the database name "zip_code" would be accessible using the hash #zip_code. The same holds true for values that are being managed by the system run time.
3. For example #gridColumns. Literals must take the fore @"value". A list of the pre-defined variables is available below.

Values from the current row contain the target table data as far as it is processed. The row continues to contain all of the source database table columns, which remain available until processing of the row is complete. At the end of processing each row is paired-down to the display columns.

Variables and literals can be used to define the selection requirements when requesting a record from the database. A variable or literal can be used as the defined data source for a given table column. For example, assume that you want to read data from a database table and you need 3 values:

1. user's id
2. the word "Unityware"
3. table value

Assume that table column is named zip_code, the definition would be:

@user @"Unityware" #zip_code

Using Variables—

Some sources of data have special syntax in the form of a leading character. Values from factory defined and user defined variables require a leading character, @ and ? respectively. Database table and display table values are also available using the leading character "#".

Factory pre-defined variables always start with the "@" character for example @time. Literals, fixed data values, can be added to the program using the pre-defined variable "@" in the form @"any data". The program gains access to a literal via the "@" pre-defined variable and then uses the literal as an immutable because the literal is in quotes.

User defined variables are created with the reserved word "set". A user creates a variable by setting a value. One example for setting a value may be set ?myvariable (values). Data placed into variables can be a collection of values from other variables and text. For example, the syntax to place into a user defined variable for a first name in one column and a last name in another column would be (assuming the column names):

set ?myvariable (first_name @" "last_name)

Any text, including spaces will be included and can be placed as a literal. One embodiment uses a pre-defined variable for a space called: @space.

As a general rule of thumb:

- @name translates into system values
- @"value" translates into the literal value between the quotes
- ?name translates into user defined variables
- #name provides access to values in the display table.
- Access to predefined values is collected from the host web page, logon, user or operating system. For example, date and time are determined by the operating system. User id and facility id come are determined by the login and host IP address is determined by the host web page.

Please note that the system variables are case sensitive. As of the first release the available system variables may include but are not limited to:

Patient
@blue
@community
@date
@dateformat
@dialect
@empty
@facility
@facility
@green
@height
@hostname
@iconpath
@iconsize
@ipaddres
@ipport
@language
@nation @numericformat
@opacity
@program
@programaccessgroup
@programclassset
@programcommunity
@programfacility
@programnation
@programregion
@red
@region
@serveripaddress
@serveripport
@serverunavailable
@socialformat
@telephoneformat
@time
@timestamp
@topic
@topicheight
@user
@virtualapplication
@virtualprogram
@virtualstructure
@virtualsystem
@width In addition, patient related values are available after a patient is selected. These system variables are labeled slightly differently with each concatenated word capitalized. Within the patient specific system, variables are “switches” that can only translate into the words “true” or “false”.

These system variables are named using the words that most closely resemble the options to which they represent. The system variables include the following:

@PatientId
@PatientuniversalId
@PatientNameLast
@PatientNameFirst
@PatientNameMiddle
@PatientNameSalutation
@PatientNameSuffix
@PatientSourceId
@PatientSoundexFirst
@PatientSoundexLast
@PatientSoundexMiddle
@PatientPhoneticLast
@PatientPhoneticFirst
@PatientMaidenName
@PatientNickName
@PatientTitle
@PatientDegreeId
@PatientSocialSecurityId
@PatientStatsBirthYear
@PatientStatsBirthMonth
@PatientStatsBirthDay
@PatientStatsDeathYear
@PatientStatsDeathMonth
@PatientStatsDeathDay
@PatientStatsGender
@PatientStatsRace
@PatientStatsEthnicity
@PatientStatsNationality
@PatientStatsRegionId
@PatientStatsCitizen
@PatientStatsMaritalStatus
@PatientStatsBirthCity
@PatientStatsMultipleBirth
@PatientStatsBirthOrder
@PatientStatsStudent
@PatientStatsLivingWill
@PatientStatsDNR
@PatientStatsOrganDonor
@PatientPrimaryProviderId
@PatientPrimarySourceClinic
@PatientPrimaryFacilityId
@PatientPrimarySourceSystemId
@PatientPrimaryComments
@PatientPrimaryMedicalWarnings
@PatientHomeAddress
@PatientHomeStreet
@PatientHomeUnit
@PatientHomeCity
@PatientHomeState
@PatientHomePostalCode
@PatientHomePoBox
@PatientHomeCountry Switches

| | |
|---|---|
| @PatientFlagHIVLimit | Does this patient have HIV/AIDS and require special restrictions on sharing of medical information? |
| @PatientFlagPhysicLimit | Does this patient have psychological medical services with special restrictions on sharing of medical information? |
| @PatientFlagLocalAccess | Can medical records be accessed at the local source of stored information? |
| @PatientFlagBetweenClinics | Can medical records from clinics be accessed at any authorized clinic? |
| @PatientFlagClinicHospital | Can any medical records from clinics be shared with any authorized hospital? |
| @PatientFlagHospitalClinic | Can hospital medical records be shared with any authorized clinic? |
| @PatientFlagHospitalHospital | Can hospital medical records be shared with any authorized hospital? |
| @PatientFlagShareEmergency | Can medical records be shared outside of authority in emergencies? |
| @PatientFlagRecordRestricted | Is this patient under special security and requires at least 2 logged on users to gain access? |
| @PatientFlagRecordRisk | Is this patient a public figure where medical records are at greater risk of being comprised |
| @PatientFlagPersonRisk | Is this patient a victim requiring special protection of medical information? (rape, battered wife, etc.) |
| @PatientAtRiskRecordReason | Description of the reason or reasons that this medical record is at greater risk of being compromised |
| @PatientAtRiskRecordAction | Id code indicating the re-active action that the system should take when this record is accessed |

-continued

| | |
|---|---|
| @PatientAtRiskPersonReason | Description of the reason or reasons that the patient is at risk |
| @PatientAtRiskPersonAction | Id code indicating the re-active action that the system should take when this record is accessed |

Additional values from other tables are referenced when transported by the authority. These variables will function if the related table is referenced during a given transaction. Although it may seem that all of the supporting information will always be available, it is not the case. Transactions can be based on one of the other items transported by the authority.

Logon
@LogonNation
@LogonRegion
@LogonCommunity
@LogonFacility
@LogonDepartment
Transaction
@OrderDeptOrderNumber
@OrderPatientIdSource
@OrderPatientTarOrderId
@OrderPatientUnityId
@OrderPatientUniversalId
@OrderDeptOrderNumber Using the symbol with quoted values @"value" translates into the literal value between the quotes. Literals are almost any value, but it is proper practice to use letters and numbers.

?name translates into user defined variables. Single words without spaces or other special characters are supported in user defined variable names. For example, ?SampleDate uses the syntax: variable ?name "value" to create new variable and set it to a specific value. The user can create a variable without a value by not entering a value.

Plain words will translate into interpreter table field names. Program table names are the table column names used as fields by the interpreted program. They are defined in table_fields. You can find them via the Universal Database Manager which is available from the main panel for the Unityware server The program table names are the variables to gain access to values in the displayed table. The program table names are used for those table columns which are set to show. For columns that are not showing, use one of the other variable types. Values will automatically be from the current table row.

Logical Operations and Math—Mathematical expressions can be added to logic using literal values and variables. The generally accepted symbols for arithmetic are used (see below).

The syntax needed with the use of logic and math operators is straight forward and consistent with the commonly accepted practices. Both math and logic symbols syntactically expressed as value symbol value, for example 2+2 or A>3.

The following details the available math symbols and their function. The symbols are listed in order of the priority in which they will be processed:

Raise to a power ^
Multiply *
Percentage %
Divide /
Add +
Subtract −

Logic is expressed using a collection of symbols and reserved verbs. Orders of priority (nested expressions) are supported using parenthesis. Nesting is supported in both math and logical operations. The following are the logic symbols:

Start of priority control in nested math or logic: (
End of a nested section of math or logic:)
Less than: <
Greater than: >
Less than or equal to: <=
Greater than or equals to: >=

Logic is orderly and as simple as possible and practical. The syntax is constructed as "verb value target". The following details each of the available reserved nouns with a description of function and an example:

if: Test the relationship between two values
  Syntax: if argument action
    Numeric example: if @days>30 set warning_flag "Y"
and: Join two arguments so that both have to resolve true
  Syntax: if argument and argument action
    Numeric example if @days>30 and age equals 60 set warning_flag "Y"
or: Join two arguments so that either or both have to resolve true
  Syntax: if argument or argument action
    Numeric example if @days>30 or age equals 60 set warning_flag "Y" else: Join two arguments so that one has to resolve false while the other must resolve true
  Syntax: if argument or argument action
    Numeric example if @days>30 or age equals 60 set warning_flag "Y"

Logical actions are expressed using a small collection of reserved words called simply, "verbs". It is a design consideration to minimize the number of verbs needed to express logic.

if: indicates that logic is to follow
  Syntax: if(argument) action
    Example: see examples below
and: alpha numeric test for more than one argument being true or false
  Syntax: if(argument and argument) action
    Example: see examples below
or: alpha numeric test for only one of two arguments being true or false
  Syntax: if(argument or argument) action
    Example: see examples below
else: alpha numeric test that automatically creates a test for the inverse of the preceding logic
  Syntax: if(argument or argument) action else argument action Example: see examples below
equal: Test comparing to text values for equality
  Syntax: if(A equals B where A and B are variables or literals
    Example: see examples below unequal: Test comparing to text values for non-equality Syntax: if(A unequals B where A and B are variables or literals Example: see examples below Commands are also available and follow the same format as logic:

set: Update a variable with a value

Syntax: set target value

Example: set days_here 30 get: Retrieve a value from a variable

Syntax: get source

Example: get days_here call: Request a result from a stored set of program detail lines Syntax: call value Example: call "aging"

start: Transfer control to a different stored set of program detail lines

Syntax: call value

Example: call "aging"

Some Examples:

if(% name equals @"john") set ?name @"have the name john"

if(% action_date unequals @date) set ?myvariable @"today" else set ?myvariable

@"Monday"

if(% name equals @"john") set ?name @"have the name john"

if(% name equals @"john") set ?name @"have the name john"

if(% name equals @"john") set ?name @"have the name john"

Gaining access to topics—Patient information is divided into categories called "topics". Each of the topics is a different aspect of the patient's medical record, for example, "allergies" versus "insurance". The details of each allergy and the list of the allergies become available for a given patient in the Allergy topic.

Program Access Groups—

Users of the system can gain access to a specific topic based on the access portal which is associated with a given facility or kind of facility. The webpage in which the portal resides identifies a Program Access Group which is a defined list of available topics. The system ships with a collection of implemented examples. Including:

1. All
2. Default Clinic
3. Default IT
4. Default Office
5. Default Review
6. Development
7. Order Processing
8. Support
9. System The program Access Group defines the available topics. The program Access Group also defines the topics to which a given access point is limited. The fact that a topic is available through a given access point does not automatically grant access to any given topic for a specific user.

Program Class Sets—

Users are assigned to sets of topics based on their need to know about the various kinds of patient information topics. Pre-defined groups of topics called "Program Class Sets" list a specific set of topics a given user can be granted access.

Only topics that are already made available via the Program Access Group can be made available via the Program Class Set. Topics referenced in a Program Class Set that are not a member of the Program Access Group will be ignored.

The Program Access Group defines all of the possible topics that can be access through a given portal. The Program Class Set grants access to selected topics with the access group. The system ships with a collection of implemented examples including:

1. IT
2. Medical
3. Operations
4. Processing
5. Support
6. System

Access Groups Versus Class Sets—

A specific topic is only available to a specific user via a specific access portal if the topic is listed in both the web page's access group and the assigned user class set.

Not listing a topic in Program Access Group will prohibit access from the web page referencing that access group. On the other hand, all of the topics listed in an access group are loaded each and every time the web page starts the CEMR applet.

It is therefore important to only include those topics that are required in a program Access Group. A secondary portal can be created to handle topics that are rarely used.

Access Implementation—

The Program Access Group is specified in the webpage using the "programaccessgroup" parameter. For example, <param name=programaccessgroup value="Default Clinic">. The Program Class Set is assigned in the user record.

Unification Server

The Unity server is a virtual environment that consists of real database of similar or disparate design. The form, function, structure, organization, content and actual database manager are no longer relevant to gaining access to information. The system creates an amorphous data environment by unifying applications and databases. Data access from a database is normally accomplished by knowing where and how the data is stored.

The Unity server accesses data based on context. In effect, data is accessed, updated or inserted based on the reason the data is needed. A set of context translators are employed to translate between how data is to be accessed and why it is to be accessed. Programs can gain access to information without knowing where or how the data is stored, only why the data is needed. In addition, the source of data as well as structure, competence, or other "fixed" characteristic can change without crippling the software or causing cascading failures across an enterprise of disparate databases.

All of the disparate databases become unified into a single data environment. Application software can be integrated without any interfaces and in many cases, without adding any software to the target system. Application software needs only know why it needs the data and the system will automatically translate to the location, connection and form in which that data is stored. Each application and its database exist in a "system space". System spaces do not have an interface and do not require application awareness.

It is also possible for the unified system to "heal" itself when there are failures or unpublished changes in one of the unified system's design. Alternate databases and applications can be employed for access when one of the unified systems goes off-line. In fact, automatic re-routing is accomplished without the system encountering an error and without delay. Applications do not need a database connection and can be isolated from the network in general. Databases need not be exposed to the network or other opportunities for access to be compromised.

Complete access to information can be accomplished with only two programmatic Objects. 1) NetObject and 2) Client. An example in program code is:

client=new Client( );

netObject=new NetObject(<internal context>, <directive>);

netObject=client.communicate(netObject);

In the above example, data can exist in databases at any location over the network or locally. Alterations to an implemented database will not cause the application to fail or require any programmatic changes. The translation can be adjusted to match or the system can interpolate the most likely correction. Data transportation via a NetObject has no metadata or any specifications about a database. The context is translated into database references at the last step before handing the data (or request) to any given database server. The detailed steps of the process will be discussed below.

Contexts

New contexts are automatically established when the system starts. The user can attach additional databases at any time and have the system generate translation support. Normal databases and their structure are called an external context. The understanding needed by an application to gain access to data is called an internal context. Each data element is automatically mapped for type, structure and other characteristics which are translated to a like set for other database elements that are substantially similar or are for the same purpose.

Users can map translations and override names as needed. The relationship between internal to external contexts is not a rigid one-to-one direct connection. Internal contexts do not have to abide by the rules of a database of the structure of tables within. Multiple internal contexts may wind up referencing the same data in the actual database.

Another way to look at contexts is that the external context represents where the data lives and how to gain access. Internal contexts are not concerned with the physical mechanics of database access. Internal contexts can be thought of as "why" and "when" an application needs to gain access to the data. For example, the internal context "Accounting", "Payroll", "Time" could translate into a table (external context) in the systemA.database:general_accounting.time_tickets over a network database connection in another facility. A similar context "Accounting", "Payroll", "People" may translate to either systemB.database:general_accounting.personal_records or systemZ.database:staffing.help_wanted. The difference could be caused by the source of the request, time, system availability or a host of other variables. The structure of the actual database is static and forces a specific set of rules for database commands. Translations can traverse table and database boundaries and do not have to reflect the actual database in which the data resides in any predetermined structure. Structure can be simplified and "de-coupled" from the actual database allowing applications to exist without being database aware.

Translation Matrices

The system employs a translation engine which implements translations matrices. A series of cross-translation specifications are generated when the server is started. These translation matrices can be stored, pre-generated or re-generated on the fly. The generated matrices are managed in memory for performance, but can also be stored persistently or off-line as needed. The generated matrix is a multi-dimensional set of arrays that is managed by a series of programmatic classes called aliases. Each aspect of the translation matrix is assigned a unique alias and is then handed to an appropriate alias manager. Other ways exist to construct, manage and access the translation matrices, such as a simple node network. Matrices are more than pointers from one place to another. Matrices can dictate or trigger time based events. The order aspect of the translation matrices can contain multiple characteristics, which can determine a temporal relationship, dominance, alternates, direct relationships and the like.

Organization sequences play an important role in the matrices system. The sequences can reflect the order of data in a table or a different order of the same information elsewhere. The sequences can also be used for typing and alignment. Sequences can guide conditional processing without the aid of expressed logic. The implication of logic allows the system to perform complex tasks based on the data and sequences. The current system employs aliases and alias managers including: 1) Columns, 2) Tables 3) Order, 4) Specifications, 5) Listener/Events 6) Connections and 7) Auto-join.

Database Command

NetObjects and messages are received by the Unification server and translated in stages from the minimal specifications to complete table based requests. The database command processor is started for a NetObject and processes translations by building on one result to feed the next. The SQL generator is automatically started once a translation reaches critical mass and can be acted upon.

Automatic SQL Generation

The server has an SQL generator which is driven by the translation matrices. The generator automatically picks the correct syntax for the brand of database on a given connection. After translation, generation of SQL, XML or other database interchange standard is accomplished with generally accepted techniques. Another option is to employ a "realizer" see U.S. Pat. Nos. 5,815,717 and 6,864,779, which give the system a dynamic and self-adapting code generator. Implementation results in code generation at the maximum efficiency known for each given brand of database manager.

Different databases have different implementations of SQL. The current generator automatically accounts for the different implementations of SQL and unique punctuation. In one embodiment, SQL is generated on the server closest to the target database significantly reducing network overhead to moving full SQL statements. NetObjects are transported with minimal overhead until the requests are close to the target database. System performance can thus be enhanced by connecting the Unity server and database server via a high speed dedicated connection. The clients can then access the system and gain access to data over slow connections.

Actions

External Context translations establish a common "understanding" of two dissimilar databases schemata. Any number of divergent databases can then be connected and accessed to a single common standard. Each of the divergent databases is aligned with the model providing the rules to translate between the model database and any of the connected databases.

Applications remain unaware of the actual database structure. An application is provided with an assumed data order which is then automatically kept constant as the application requests, stores or updates data. The server then handles the interaction with the database to access, update or save information.

NetObject

The NetObject is a streamlined data transport that can move data across a network with almost no overhead. SQL or any database specific form is rendered unnecessary (although the system can support traditional data dialogs). In effect, only the data moves across the network without any environmental or structural specificity. The NetObject is provided a single word that reflects the desired action. For example, QUERY or SELECT and a small collection of abstract words that reference the context. No other overhead or directives are required. For example, to reference an employee in context of being paid is different than the context of performance review. The first context could be "accounting", "payroll" and "staff". While the second context for the same employee could be "accounting", "personnel" and "staff". Any number of words can be used to reference a context. However, the system can address all situations using only three words. Netobjects can transport directives that directly affect the generation of SQL. For example, to range in a specific value or limit the size of returned result sets.

NetEvents

NetObjects can be relayed through multiple "tiers" of processing in a network. For example, result sets can be transferred whole to one point in the network and then parsed out as needed by nodes, servers or clients. The system also supports network events which can relay other kinds of events or trigger processes on their own. Like NetObjects, network events can be routed, interpreted or processed. For example, a collaborative application could receive events that report changes in other clients or elsewhere in the network.

The system manager GUI, called the Universal Database Administrator (UDA) employs the technique to make sure that the displayed information reflects the actual system state. The GUI accepts actions from the user, but does not change the display to match the user's actions. The display then changes when the server echoes a message indicating that the user's request has been accomplished.

The UDA sends messages to the server via a normal NetObject, but makes no changes to the display from the user's actions. The Unification server issues return NetObjects when the desired actions are correctly executed. The UDA then modifies the display to show the user the new state at the server. Clients of the server can receive responses to requests, problem reports, and unsolicited events over the network. Local events or network events can be triggered by any transaction or table access which the system is aware. The system also supports "plug-ins" which can be started based on a kind of transaction or a kind of database table access. The system also supports non-NetObject messages. Traditional SQL can be transported as a normal message or via a NetObject.

Triggers

Any action to which the system is aware can trigger an event, start a plug-in or cause subsequent automatic processing. Triggers are started when the system detects database access or a non-database transaction, for example a message. Triggers allow dissimilar applications to become integrated through the Unification server. Enabling two applications to behave together requires more than moving data. Frequently, there are processes missing that would have been automated between the systems.

The Unification server can translate similar information between dissimilar systems. The form, structure, format, design and other characteristics are re-created changing the data to match the target system. The missing automation between the systems can be added directly to the Unification server by adding plug-ins. New capabilities, which may replace manual processes, can then be fitted between the two dissimilar systems. The result is a processing environment that acts as a single system with consistent continuity between tasks, users and processes.

The server employs both transactional and data triggers in its own operation. For example, when there is a change to translation specifications. The server "senses" the change via a trigger and starts internal processes to synchronize the changed data with the in-memory generated translation matrices. Other examples include watching a specific table to trigger client notifications in which the clients to be notified are selected by a geo-location key.

NetObjectQueue

NetObjects can be created by remote hosts and sent over the network to the Unityware server for execution. In other cases the NetObject may be created on the same server as is the running Unityware server. NetObjects can be used by normal application clients, but are also used by the Unityware system.

The queue can allow NetObject transactions to wait for databases that have gone off-line to again become available. The queue also allows a NetObject transaction to wait for a planned database that has not yet been connected to the system. The queue can work in conjunction with the server's ability to re-route transaction on the fly. For example, transactions of a given type or containing a specific value could be auto-routed to a database that does not yet exist. The transactions would then automatically be applied when the target database does exist and is connected to the system.

Client

As the Client is the vehicle for transporting data (or commands), connections between Clients, Servers or Clients and servers become the transportation conduit in which data and commands are passed. A single Client and NetObject can replace virtually any communication traditionally performed between databases and applications. For example; an application can request metadata about a database or actual system definitions about the host computer on which the server is running. Clients can also support communications to and from non-Unityware complaint data sources or modalities. For example, communications messages with a government system.

Concept

Database translation goes beyond translating table and column names between environments. The Synthesizer system employs a "smart" translator that can accommodate variances in datatypes and column order. In a complex enterprise it is possible for table specifications to change without warning. Changes can be programmatic that suddenly expect new fields or new orders. On the database side, it is also possible to encounter database changes to table layout as a new or removed column, change the order of columns, or both.

The Synthesizer attempts to keep the system up and running by insulating the actual database specifications from that of a "Virtual Database". The Virtual Database can represent a plethora of different database managers on different host machines, running under different brands of DBMS. All of which suddenly become a single database environment. Data access availability is enhanced through automatic translation for datatype, column name, table name, organization, type of database manager, system location database location, or schema. Systems can stay on-line and operational without having to change either the program side or the database side. Such a system provides the software or database engineers with time to resolve the issue.

Virtual Databases are organized from the program's point of view. Tables from various implementations could easily be treated as related to a single Application. A table may have multiple Virtual counterparts. The Database Insulation process is executed from the unification server's Gateway class, which is the starting process for the server side of the system.

Figure 17:
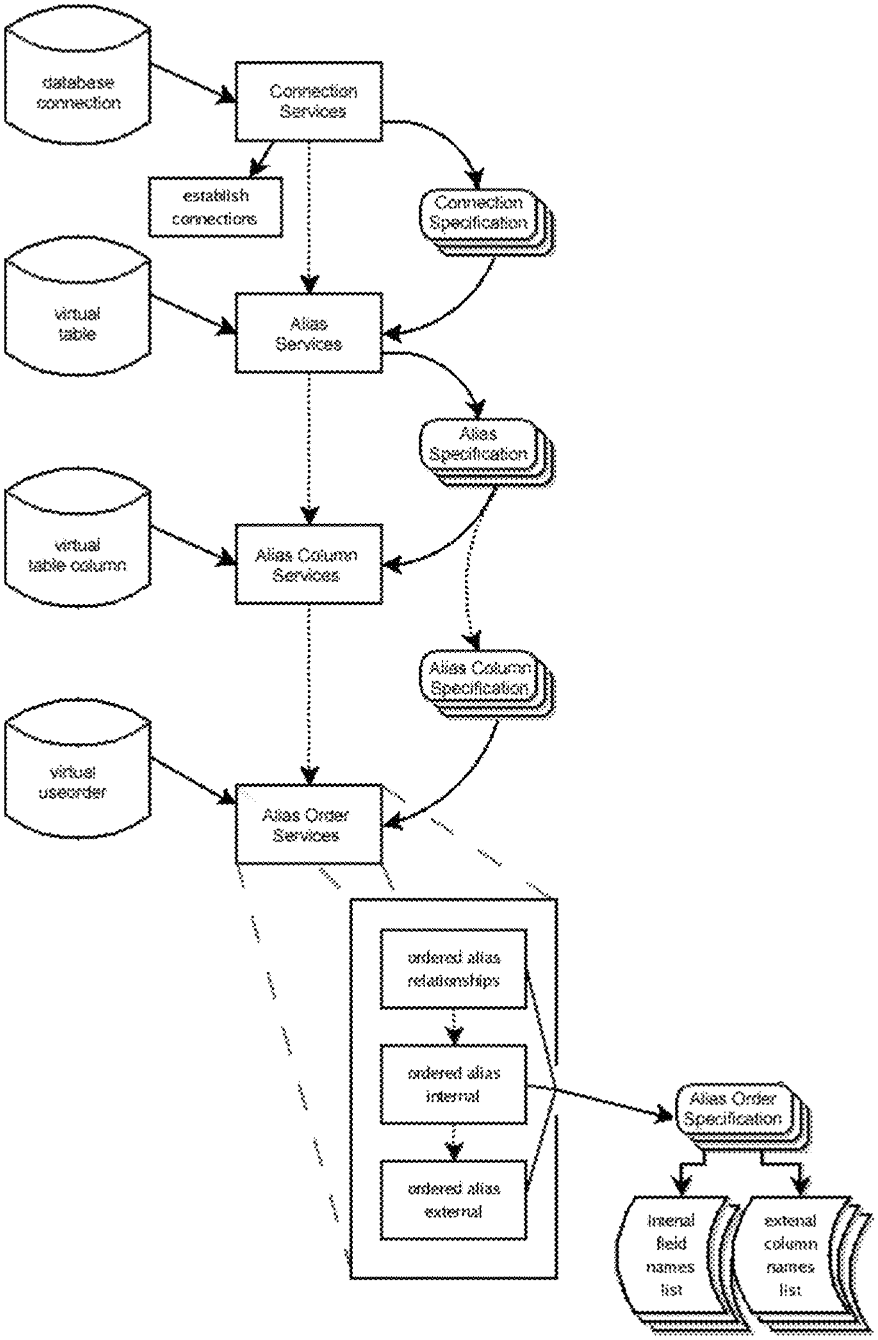
FIG. 17 shows the unification process of one embodiment of the present invention.

Referring to FIG. 17, the process is established at system server start time to limit the processing overhead that would otherwise be inflicted on the server. The above image details the initialization which prepares the system to support dynamic translation:

Object Assignments

The lowest level of detail is populated in the order the objects are added. For example, field order is determined by the chronology in which each field is recorded.

Ordering and comparative ordering is supported by AliasOrderServices and its children AliasSpecifications. Ordering does not affect the value or naming translation that is supported by the combination of AliasServices and AliasColumnServices. Ordering is a different kind of translation which responds to differences in the organization of internal and external data structures.

Ordering is the reason the system can interact with a database table where the column positions have changed, been added or deleted.

Added columns will not be populated. Deleted columns will cause any data submitted to that column to be ignored.

Translation Process

In one embodiment, translation is first achieved for the naming criteria using the same process to translate to external database as is used to translate to internal data structures. Naming criteria for internal data structures includes a set of words which have meaning to a user or application. Name for the "fields" in which one might find a context has no meaning. In the current implementation, there are 3 fields called either 1) System, 2) Application or 3) collection.

The names are arbitrary since the meaning changes with context. The three values could be called "context value 1", "context value 2" and "context value 3".

Naming criteria for external database (connection) conforms to the norm for databases for example and is named for reference in the system: For example;

1) Connection identification, 2) Schema and 3) Table name.

Figure 18:
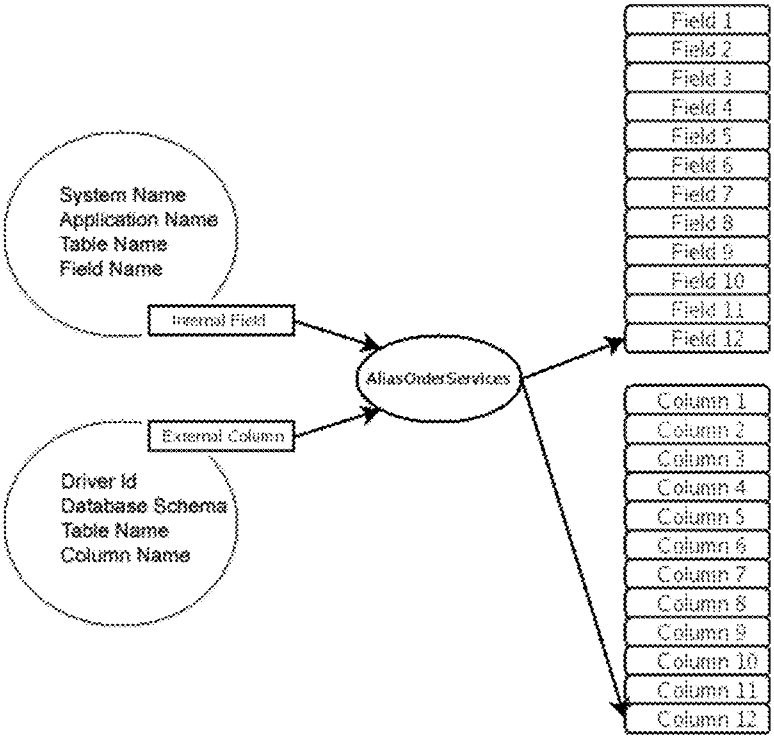
FIG. 18 shows the alias order services of one embodiment of the present invention.

Referring to FIG. 18, translating between the naming criteria of internal stored fields and external database columns uses a direct relationship. The relationship is defined by context. The combination of words that make up an internal context and the combination of words that make up an external context provide the meaning. For example; the Application name can translate into any schema. No explicit or implicit relationship exists between any single value on one side of the translation to a value on the other.

The relationship employed when translating between internal field names and external database table column names is less direct. This translation step accounts for differences in the order of the data elements and for changes in that order.

Data element names are translated directly using the table translation relationships established from the previous step. The values (not the data names) are then re-organized based on the implied difference in order described by delta between the translated column names and the original ones.

In one embodiment, the re-ordering is only attempted if the internal expectation of the data element order is different from the actual database table column order.

Automatic Inter-Context Translation

External contexts can be related to one another so that a client is defined and operates to a given internal to external context set (per normal operations). However the automatic external context translator can re-route the database request issued via a NetObject.

Current Implementation

The context translation process consists of a series of "cascading" converters called "aliases". Each converter feeds the next, working from the general to the specific. Each process has its own definitions. The core components of the translator are:

| | |
|---|---|
| AliasColumnConverter | Convert AliasColumnSpecification Objects to and from communication messages for transport across the network. |
| AliasColumnServices | Manages defined table column name translations between internal and external database concepts. |
| AliasColumnSpecification | Encapsulates a single relationship between an internal field name as known by the Synthesizer system and the external table column name as known by an external database Management System (DBMS). |
| AliasConnectionConverter | Convert AliasConnectionSpecification Objects to and from communication messages for transport across the network |
| AliasConnectionServices | Manages existing database connections providing services needed to take advantage of the database connections in the ConnectionSpecifications control array. |
| AliasConnectionSpecification | Each implemented database is represented by an instantiated specifications Object which contains the requisite information to connect to a specific Database Management System (DBMS) on a specific host machine for a specific view and schema. |
| AliasOrderConverter | Convert AliasOrderSpecification Objects to and from communication messages for transport across the network. |
| AliasOrderServices | Manages the defined column and field ordering Objects. |
| AliasOrderSpecification | Encapsulates the order of fields in the internal Virtual Database tables and the order of columns in the actual external database tables. |
| AliasServices | Manages sets of AliasSpecification Objects where each managed Object represents a translation relationship. |
| AliasSpecification | Encapsulates a relationship between two naming objects. |
| AliasTableConverter | Convert AliasTableSpecification Objects to and from communication messages for transport across the network |

-continued

| | |
|---|---|
| AliasTableListening Services | Maintains a listing list of external database table names to be checked for forced synchronization with in-memory representations. |
| AliasTableServices | Manages defined table name translations between internal and external database concepts. |
| AliasTableSpecification | Encapsulates a single relationship between a table name as known by the Synthesizer system and names as known by an external database Management System (DBMS). |
| Autojoin | Manages translation database table relationships for the automatic redundant processing. |
| AutojoinRelations | Manages a set of action rules associated with a given target table. |
| AutojoinRules | Contains the rules needed to automatically generate a subsequent NETObject. |
| AutojoinServices | Manages translation relationships for the automatic redundant processing where multiple tables are updated as a result of a single table update. |
| ContextConverterRule | Contains the specifications for a single directive using one of the action classes. |
| DatabaseCommand | Generate a syntactically correct line of SQL program code suitable for issuance to Database Management System. |
| DatabaseCommand Processor | Database command processor is a thread which is fired in response to a valid read operation being detected by the listener attached to the server socket channel. |
| DatabaseDriverFile Name | Locate the specifications file which defines how to connect to a given database Management System. |
| DatabaseGenerateSQL | This facility is a front end for DatabasePrepare and DatabaseCommand classes. |
| DatabasePrepareSQL | This facility 'cleans-up' components that will be used to generate an SQL statement. |
| DatabaseServices | Standardized database connection facility that should work with a database management systems from most vendors. |
| ImportMetadata | Supports the importation of database definitions into the Virtual Database definition tables. |
| ProcessSQL | Test bench, Not to be used in a production system. |
| SQLSyntaxGenerator | Create Structure Query Language (SQL) code from supplied NetObject set of specifications. |

Data element names internal to Synthesizer applications can be translated into table column names in legacy databases. Each defined possible translation is represented by an AliasColumnSpecification Object. Field names used by applications developed under the Synthesizer do not have to line up with the column names used in the database. The expected order of the columns in the database also does not have to match the database. This is handy when connecting databases from legacy systems.

Missing fieldname to column name relationships are assumed to be an exception when the table is defined as requiring translation. NOTE: reverse translation from a specific table column name into an internal field name is supported. The translation requires that you first look up the relationship between internal and external tables and then assume the same external table translation for the fields. There are other manages specification Objects employed by the SQL generation process. The set includes:

ConnectionSpecification
AliasColumnSpecification
AliasSpecifiation
AliasOrderSpecifiation
ConnectionSpecifiation Data movement between the alias cascade steps:

| | |
|---|---|
| Alias connection | External database view, schema table names, table column names, indexing structure and attributes |
| Alias order | Internal data element relationships, eternal table and key structures + references to internal and external contexts |
| Alias alias | Column names and specifications |
| Alias table | Internal context (complete) Internal context "reference", reference to implied order sorter and a set of column names, |
| Alias column | <3 field Internal context> + an internal reference name for the data element and a reference to an appropriate database table column name |

Data Elements

Internal database understanding is attached to an external understanding. The method of viewing a database by the Synthesizer system is called a context. Data is referenced by an internal context for an application and an external context for an actual database. In certain instances, the external context does not match an actual database. The relationships between the external database and the Synthesizer's external context can be modified by the translation layer. Translations allow for mismatched fields in form, scope or structure. Data elements can be concatenated, parsed, translated or modified to allow for smooth transfer of information to and from a given external database.

This area of the system uses the following components

Action Extensible class for objects that are used to translate between external contexts.

ContextTranslator Converts the form and quality of fields in a data row between formats of two database tables.

RowDataBus Attaches and transports two unrelated table rows with the intention of converting one to the other.

Translation Carries the translation support between the various steps of an external context translation.

External Database Table Column Order

The internal and external database table columns are normally independent of one another. The external database table columns determine the actual table column order to which all generated SQL must adhere. External table column specifications are added to the ordering translation context (usually before internal specifications). The act of installing the external specifications creates a default standard for the ultimate order of data elements.

Internal virtual table translation relationships and internal virtual database table columns are then added to the translation context to create one-to-one relationships between the external and internal table column names. The database column order, having already been defined by the external columns, directs the relationship construction to the internal analogous table column names.

Populate Useorders

Figure 19:
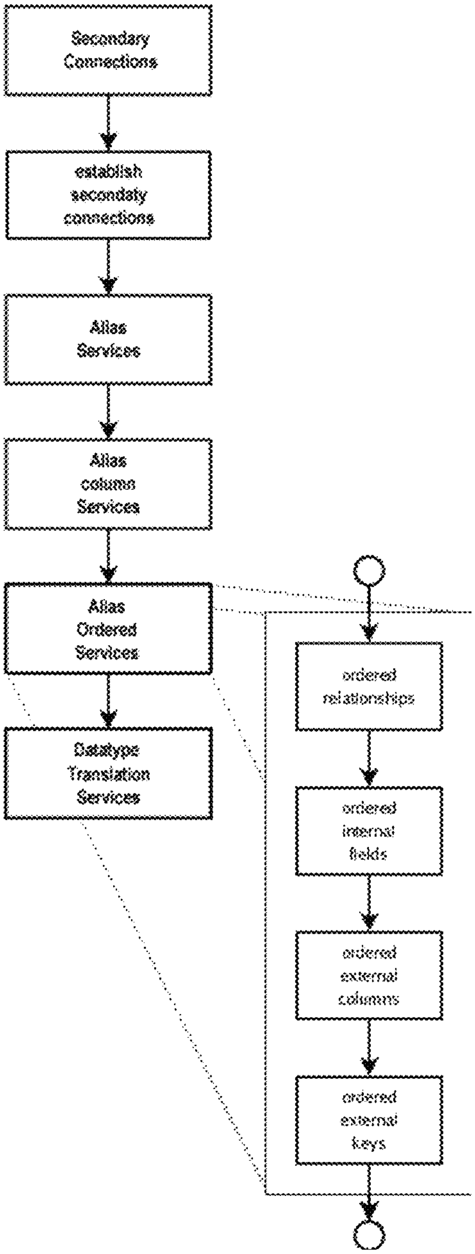
FIG. 19 shows the secondary connections of one embodiment of the present invention.

Referring to FIG. 19, the populate Useorder process is responsible for the creation of in-memory ordering Objects. For example, the ordered objects can represent the ordered translation context for internal to external database table columns. The populating process is initiated at a valid connection to a database and generates the AliasOrderSpecifications which will be used for translation when the server is accessed.

The ordered objects represent an ordering context consisting of 1) translation context 2) external database table column order 3) internal virtual table translation relationships.

The ability to establish a relationship between a set of external and internal table columns is called a context. Ordered translation contexts exist as AliasOrderSpecification Objects which are managed by the common AliasOrderServices Object. The order specification Object must first be created before any relationships can be installed.

Translation

Translation provides the transportation for related or paired data and specifications. At least two specification lists are transported through the translation process, including the source and target list of field names. The transported data starts out being described by the source list of field names. The translation process which acts upon this transport converts the data to match the arrangement of the target list of field names. The actual translation is performed by the ContextTranslator which acts on the contents of this object.

The principal use of Objects of this type is when there is an override list of field names which abridges the normal table layout. In this case the actual translation processing will not find the data in the expected alignment of a table layout (either principal or alternate). In fact, the data will be arranged to match a random list of field names as specified in the incoming NetObject. The ContextTranslator handles all of the actual translations, but it assumes that the source and target data element arrangements match actual database tables. This translation supports the distribution of data elements between matching a random list of override field names and one of the database table layouts.

Data elements are converted to align with the principal database table layout. The translator modifies the data elements resulting in a set of data elements that match the alternate database table layout. This Translator can then un-distribute the results data elements to match the now translated list of field names. The Translation transport (this object) can offer pre-generated conversion mapping between the source and target list of field names.

Softbus Implementation

The bus is intended to supply data from the source channel and receive into the target. Values in any of the fields in the source and target records are transported through Action Objects where each alters the data in some form of fashion.

The resultant values from one Action Object can be carried to the next via the bus by setting the bus with a switch that indicates which bus channel to write.

Normally from the source side, the options cause the bus to substitute the source side of the bus. Thus, the same value can be passed into multiple Action objects to another and be acted upon more than once.

The feature overrides the normal target field on the alternate side of the transaction. The process only works with single value reads via the getSourceValue(int) and single value writes using the setTargetValue(int,String) method.

Using any other setTarget( ) method will cause the value to replace in the source bus at the position specified for the target, producing random results.

Writes back to the bus that repetitively place the results in the same place require a clean read before write for each event. The system knows to place the resultant value into the same index position along the bus from the last read. Attempting to write back to the source bus without first having first called getSourceValue(int) will throw an exception.

Using the same target field name and setting the rule bus target channel back to 1 (indicates the source channel) causes the system to replace the current source information with the new results. The next step accesses the results as fresh data from the source channel.

External Database Metadata

Normal metadata is available for an external database connected to the system or is defined to be connected. Requests for metadata yield a metadata object containing a complete set of traditional database metadata. Normal metadata is not required for operation but is available should it be needed.

Translation Process Flow

Continuing to refer to FIG. 19, the translation process starts with collecting the available database connections. The translation process then creates bi-directional ordered relationships between the internal stored fields and the external database table columns. Additional description of the process is shown in the FIG. 20.

Different then the repeated model, preparation for Dynamic Translation runs right after Database connection Services is established as part of the process that establishes the secondary database connections.

In this case "secondary" means all database connections except the minimum required to start the Virtual Database Server service. This initial connection is less managed allowing the server to load the request specification needed to operate Dynamic Translation.

Another variance from the model is Ordered Services which is established in three steps:

Populate Relationships

Populate Internal Field Names

Populate External Database Table Column Names

1. Populate Relationships

Establishes the foundation for ordered internal to External name translations. Each internal Virtual Table is related to each external database table name.

2. Populate Internal Field Names

All of the internal stored fields related to a given internal Virtual Table are then placed into an ordered list within the Virtual table to database table relationship.

3. Populate External Database Table Column Names

All of the external database table columns related to a given external database table are then placed into an ordered list within the Virtual table to database table relationship.

The result is a bi-directional field name to table column name translation matrix. The relationship is ordered to provide both name translation and table or field order translations. The Synthesizer attempts to maintain the system operating by insulating the actual database specifications from that of a "Virtual Database". The Virtual Database can represent a plethora of different database managers on different host machines, running under different brands of DBMS. All of which suddenly become a single database environment.

Data access availability is enhanced through automatic translation for datatype, column name, table name, organization, type of database manager, system location database location or schema. The same is true for unexpected changes to the same list of exposures.

Virtual Databases are organized from the program's point of view. Tables from various implementations could be treated as related to a single Application. It is even possible for a table to have multiple Virtual counterparts.

The process is established at system server start time to limit the processing overhead that would otherwise be inflicted on the server if it ran each time a new client connected.

Figure 20:
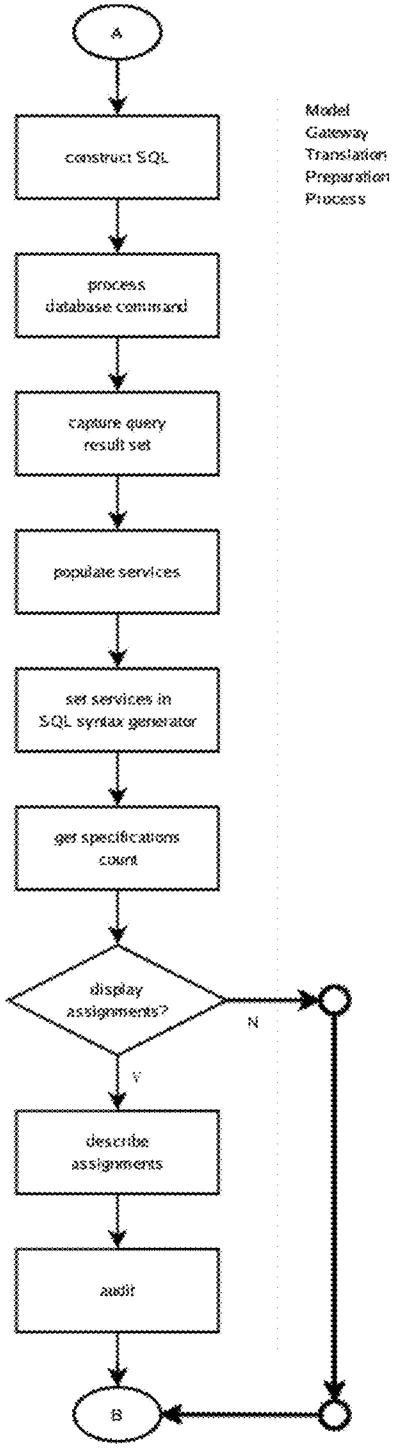
FIG. 20 shows the translation preparation process of one embodiment of the present invention.

Translation support includes field to column name, internal table to external table name, database connection, database schema, and column datatype as shown in FIG. 20. Translation support is automatically prepared when the main Gateway server is started. The process is broken into steps with each of the steps following the same model.

In each case SQL is prepared to query the database for request relationship data. The SQL is executed and then the database query result set is recovered. The resultant information is translated into an array and then supplied to one of the translation service managers. Optionally the results can be audited.

NetObjectQueue/TransactionQueue

Figure 21:
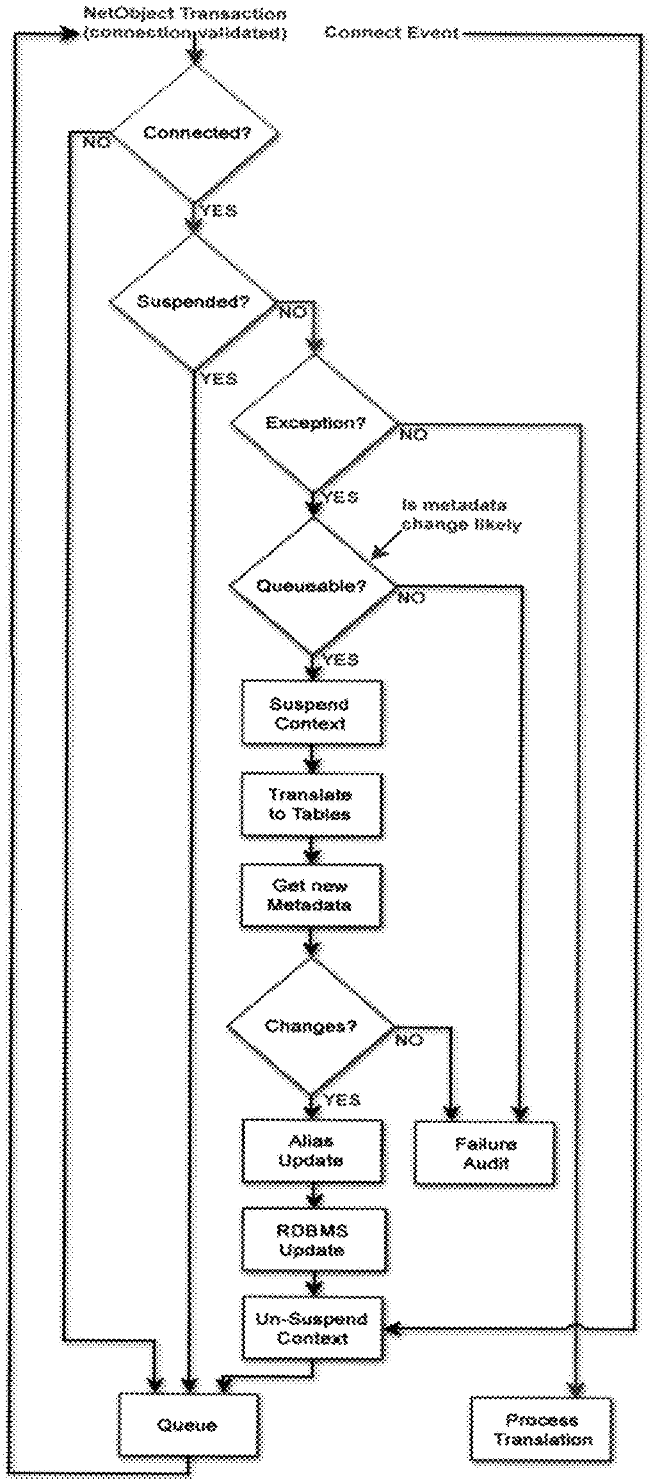
FIG. 21 shows the netobject transaction of one embodiment of the present invention.

Referring to FIG. 21, the queue manages the storage and retrieval of NetObjects between the originating request, where the object was created and the command processor intended to execute the transaction.

NetObjects can be created by remote hosts and sent over the network to the Unityware server for execution. In other cases, the NetObject may be created on the same server that is running the Unityware server. NetObjects can be used by normal application clients, but are also used by the Unityware system itself.

NetObject based transactions can be queued for later processing when a database becomes or is unavailable during processing. Queuing is intended to allow transactions to continue without respect to the availability of a given database.

Inability to access a given database can be caused by a missing table or an unavailable connection. The Unityware server allows client processes the ability to request database changes or requests that will become processed when the target database connection is restored.

Inability to access a given database or table may be intentional and caused by a user ordering a disconnect via the Universal Database Administrator} (UDA) GUI tool or a request received by the server via message or NetObject. Other causes include changing database permissions, deleting a table, or stopping the database server.

The machinery can be used to suspend a database while modifications to the data structure are underway. The queue contains untranslated NetObjects.

Translation can then take place when the database becomes available and the new target structure is known. In this way it is possible to create a database request before modifications applied after the database structure changes. The capability also supports normal transaction queuing.

Summary

SQL code is generated with the absolute minimum input requirements. A new NetObject is constructed and then supplied with a directive and possibly some data elements. The process requesting database access can discriminate between requests to insert data from those updating data already in the database without respect to the action that was actually requested. Both old data and new data can be supplied to the NetObject. The presence of both suggests an UPDATE while the presence of only new data suggests an INSERT. Additional communication efficiencies are gained for updates by automatically ignoring those values which are the same in bother new and old data.

The order of data values can be demonstrated by a simple SQL "INSERT" command: INSERT INTO 'TABLENAME' values('900121', 'Sam', 'Spade', '25987.92', '02/02/2005');

Any unexpected organization of the values shown can render the stored row useless. Of course, when the column names are used in the SQL code the order will have no effect on the resultant stored data. The Unity Server handles all of the internal to external data routing as it would when the target database has no external translations. In fact, as far as the application and the Unity translation matrix is concerned, the target database conforms to the database schemata of the target database.

Assuming that a target database conforms to a given schemata would create a data incompatibility under normal conditions. However, the External Context Translator picks up the transaction and translates it to match the format, style, organization and structure of the actual target database. The data, now matching the actual target database, is then sent to the SQL generator and on to the database. The same process is true for incoming data returned from the database in reverse order.

Although the model database does not have to exist, there are some additional capabilities when it is implemented. The transactions both to and from the various divergent databases all align perfectly with the model database. The transactions can be duplicated or rerouted to the model database without any additional processing or preparation. The server has an "autoroute" feature which automatically updates or queries the model in the event the desired target database is not available. No additional processing is required, since the data is already aligned with the schema of the model database.

Defining Relationships

Translations are defined by creating relationships between table columns in one database to the table columns in another. The relationships are established by "rules" where each rule has an "Action". The relationships can be one-to-one, but can also be many-to-one or one-to-many. In some instances superfluous data is discarded while in other instances existing data is expended.

Translations are defined in two sets, one set for translating values and table column names from the model database to the alternate database and another set for translating values and table column names from the alternate database to the model database. Both directions must be defined. In many cases the rules in both directions will simply copy the data unchanged. Data can also be modified in one direction and need to be unmodified for the reverse trip. For example, parsing and distributing a date field into unique day, month and year table columns in one direction will require combining the three discreet fields back into one in the reverse direction.

The existence of a translation rule set is defined in the generadb.virtual_translation table. The presence of an entry identifies that the external translation is expected for the referenced connection and table. It is assumed that a set of rules are established for translating to and from the target database.

Implementation

Rules control the flow of information. The order of translation is controlled by the order of the rules. Database tables on either side of the translation have no dominance, that is one has no more effect on the process as the other. The source table does not drive the process as the target table has no demand. The only assumed structure is the set of rules which orchestrates between itself and the source as well as between itself and the target database tables. Both the source and target tables are represented in a transportable object as lists of data in the expected order called channels. Table names on both sides of the translation are automatically converted into index positions at which a rule will take action. The rule finds the appropriate location on the channel and takes action.

Rules can address any location of the source of target list and do so in any order. Multiple rules can act upon the same locations and pass the results of one rule to the next. Ganging rules against a single location allows for complex alterations. For example, truncate a marital status value to the first letter capitalized. Ganging rules is accomplished by defining a rule where the results replace the source so that the next rule can continue processing. The last rule in the gang will update the target side of the translation or the data will be lost.

Rules are each assigned an Action which performs an elemental processing function, including but not limited to uppercasing a value or simply copying a value. Each rule must have an action. The most elemental is copy which transfers the value in the source channel to the target channel without making any changes (transporting the value).

Actions are named Action with the function appended. Examples include ActionCaseUpper or ActionCopy. Rules mate two fully referenced external contexts, where both are defined:

connection
View
Schema
Table
column (field)

The first external context is called the "Principal" and the second external context is called the "Alternate". The Principal external context is the model to which data organization and table column names must match. The Alternate external context is the actual database that will be queried or updated. The model does not have to exist. The model services as a standard for an application. The standard allows the application to be designed against a single known schema and allow divergent and dissimilar databases to be randomly accessed and new, unfamiliar databases added at any time.

The Principal external context is first in the translation definitions and remains the same for the same application for the same function. The Alternate external context varies to match the actual divergent database. Rules combine the name of an Action with values that define how that action is to be executed and on which table columns the action is to be executed. There are 4 values that define a rule for a given action:

rule_principal
rule_alternate
rule_rule
rule_logic

The first two (rule_principal and rule_alternate) override table columns in cases where there are more than one table column name. The difference between the first two rules is that rule_principal can only contain table column names found in the model database and the rule_alternate may only contain table column names in the actual divergent database. The first two rules are used to define one-to-many, many-to-one and many-to-many relationships. The first two rules are not used in the average one-to-one relationship.

It should be noted that rule_principal and rule_alternate are not directionally specific. Rule_principal and rule_alternate are not specific to translate to or from.

For example, distributing values from one field to many while translating from the model (principal) to the alternate (outbound data flow) requires that rule_alternate contain a list of alternate table column names. Reversing the direction in which the information is flowing (alternate to principal) would then require converting the many fields into one and also requires a list of table column names.

The following actions are example implemented actions:

| Action Object | rule_principal | rule_alternate | rule_rule | rule_logic |
|---|---|---|---|---|
| ActionCapCap | | | n/a | n/a |
| ActionCaseLower | | | n/a | n/a |
| ActionCaseUpper | | | n/a | n/a |
| ActionClean | | | n/a | n/a |
| ActionCleanAlphaNumeric | | | n/a | n/a |
| ActionCombine | Model field list | Alt field list | Separator text or empty for no space | n/a |
| ActionCopy | | | n/a | n/a |
| ActionDate | | | Not implemented | |
| ActionDistribute | Model field list | Alt field list | Parse character | Priority list (e.g. 1, 2, 1, 1) |
| ActionFormat | | | Formatting mask where # or the number 9 are replaced with the source data leaving the formatting as punctuation | n/a |

-continued

| | | |
|---|---|---|
| ActionPadLeft | Pad length is the resultant length of padded data | Character to use as filler |
| ActionPadRight | Pad length is the resultant length of padded data | Character to use as filler |
| ActionParse | Parse character | Token index at which to select data (which parsed token) |
| ActionRemove | Character to be removed from the data | n/a |
| ActionSubstitute | Character to be replace | Character to be installed at the same position in data as the character to be replaced |
| ActionTranslate | List of values to translate | List of replacement values |
| ActionTrim | n/a | n/a |
| ActionTruncate | Maximum length of text | n/a |

External Context Translator

The Unity server can be connected to a plethora of database brands and database architectures. In some cases, the divergent databases store ostensibly the same kind of information but are different enough to make it difficult or prohibitive to reliably interact with a given application. Additional databases with yet other architectures may also need to be accessed after the system is on-line.

The External Context Translator dynamically alters the data so that many disparate databases can appear and behave in a uniform way. For example, Reformatting, concatenating, parsing or rearranging the fields to match a common standard.

Functionality

Two major services are provided:

8. Translating actions between a database and an application
9. Automatically rerouting transactions to an alternative when the desired database is off-line. The two capabilities are inexorably linked.

Translating Actions

Order, structure and format of a database table are automatically altered "on-the-fly" to match a uniform standard. Multiple disparate databases are then available as if they have always been designed to the same common standard. The common standard can describe an actual database or can be a virtual concept.

Queries and updates are made without the need for SQL (or any other form of code) and without any awareness of the actual data structures or database architecture. Translation is between two external contexts without respect to any internal contexts. In fact, the translation can serve to dynamically decouple an internal to external context translation.

Transactions to and from a given database that goes off-line can automatically be applied to an alternate database without any effort or awareness by the application. In fact, the transaction can already be "in-play" when access to the target database is lost.

Rules are defined to establish how the data, in a given divergent database, will be brought into alignment with a defined and common standard. Rules link the data source and data destination field by field. Translations are "driven" by the defined rules.

Data is presented to the translator in a transport "bus" with which the rules interact. The whole of the source data is automatically arranged to align with the known table or field names on a given side of the translation.

Figure 22:
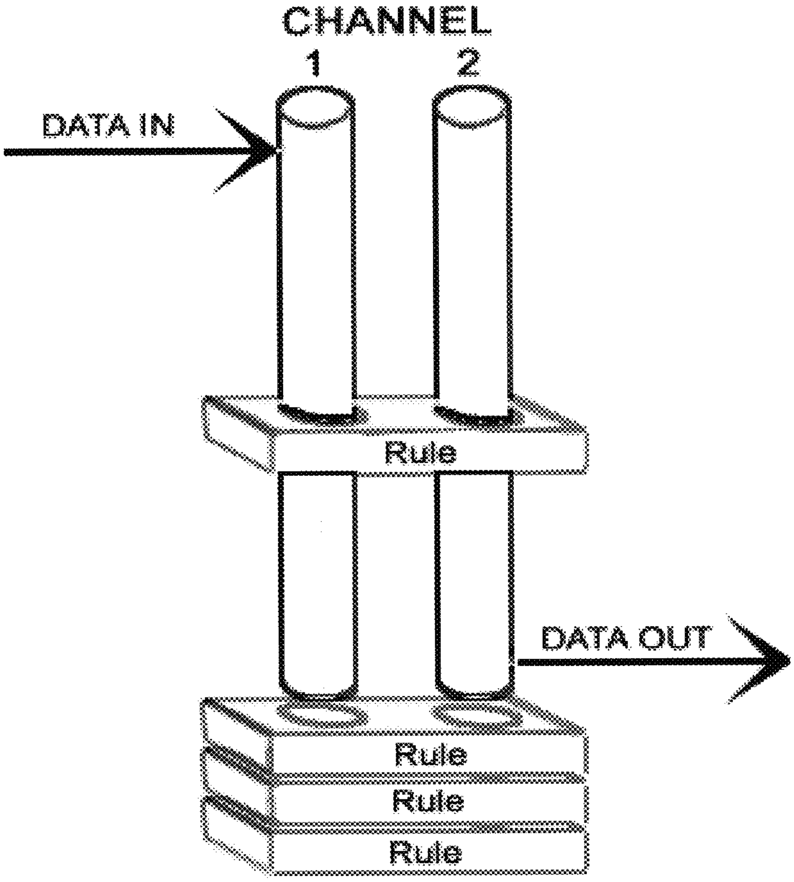
FIG. 22 shows the data unification of one embodiment of the present invention.

Referring to FIG. 22, rules and the bus act together to process or translate data where the rules represent the action and the bus represents the environment. The rules and bus work together to create dynamic processes where meaning or action can change to match the need at hand.

Rules transform data between the two bus channels where channel 1 can represent the source and channel 2 can represent the target. Data can be copied, modified or created within a rule. Rules slide up and down the bus to become aligned with the correct source and target elements of data.

Multiple rules can act on the same data and a single rule can act upon multiple source or target elements. It is also possible for a rule to act on only one channel or without a source of data.

For example, existing data can be parsed from a single table column from one database into multiple table columns in another, even in cases where the source data will not reliably parse into a fixed number of new elements.

Rules can take or place values in any bus channel. It is assumed that data arrives in the first bus channel and is returned on the last bus channel for the purposes of this description.

For example, a ganged set of rules acting on the same source data, pass information from one another through the bus. In this case, all the ganged rules (save for the last) could pick up data and update the data on bus channel 1. The last rule in the gang would then pick up data from channel 1 and update the data on channel 2. Rules automatically find their respective locations on the bus by the names of data, thus a rule must reference the actual name of a given data element in the external context.

Relating to Two External Contexts

The "Principal" external context defines the data architecture, while the "Alternate" external context is that actual source and destination of data. Requests from the application will be presented to the Unity server as the "Alternate" external context formatted to match the "Principal" external context. The transaction can be automatically rerouted to the "Principal" external context should the "Alternate" be unavailable.

Implementation—Application

Figure 23:
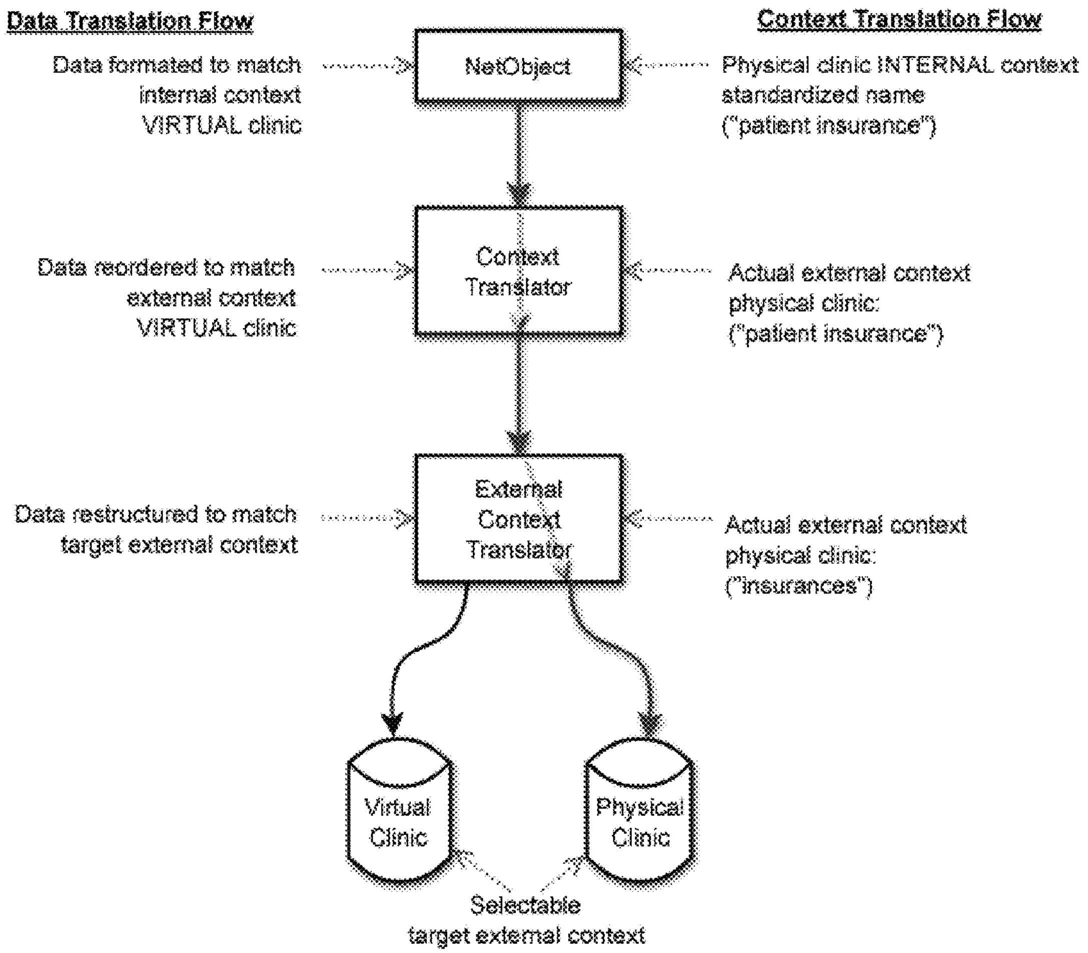
FIG. 23 shows the translation flow of one embodiment of the present invention.

Referring to FIG. 23, translation is accomplished with the Unity server's collection of context translation engines. The normal internal to external translation handles the re-assignment of names and tables. The external context translator alters the form and structure of the data to match with the target clinic database or the Virtual Clinic when the target is off-line.

Application data access via NetObjects uses the same methods as it would for any database access. Most of the NetObject implementation permutations are supported.

The most unique issue to keep in mind is that the context defined in the NetObject does not necessarily match the format of the data. In this case the NetObject is referencing an internal context and the format of information is assumed to be that of another and possibly dissimilar database. Notice that it is the format of a dissimilar database—not the actual target database.

The desired context is still referenced in the same way as when there is no external context translation. The only visible difference to the application is the assumed format of information. In practical use, the format and organization of a common database will determine the organization within the context, as if the information is in that form.

Implementation

DATABASE_TRANSLATECONTEXT: The External Context Translator is a data format and structure alignment processor that fits between an external remote database and an external Unity server context. The processor alters the form, structure and alignment of individual fields (table columns) between an external context and a remote database.

Translate context alters the current lists of data and external field names "after the fact" to align with tables of differing field counts and data formats. The process works by intruding on the connection between a database and its assigned external context. The client focuses on internal context that translates a specific (and possibly pseudo) external context.

The need to implement translation assumes that there are multiple similar databases that contain the same kind of information, including but not limited to Accounts Receivable for different companies. Translations can support the implementation of an "alternate" database or the unification of multiple similar databases.

Alternate databases assume that there are two dissimilar databases, the target database and the principal database, residing on different machines (or different connections on the same host computer). The target database supplies and stores information in the normal course. The target database is referred to as the "Alternate" database. The "Principal" database is a model that is automatically accessed when the target database is not available.

The application can update the "Principal" database each time it accesses the "Alternate" database. Relatively current data may be available when the target (Alternate) database goes off-line, assuming that the application updates the "Principal" database on each query or update.

The application updates the Principal database to allow the Principal database to remain current. The consistent updates will assure that the alternate is as current as possible when the primary principal database is not available. However, switching to access the Principal database when the Alternate is not available can be automatically handled by the server.

Unification of databases assumes that there are two or more remote databases which contain similar information. The data in the different remote databases is assumed to be of the same or similar topic and may or may not be structured differently, for example, the patient record in different brands of clinical systems. Unification of databases requires that the data in the database to be accessed can be used for ostensibly the same reason or purpose.

Each of the connected databases may not have a complete set of data when compared to one another. However, there is assumed to be a sub-set of each one that can be aligned with the others, such as a patient's name and address.

External Context

The external context acts as a constant to which an external database schema is expected to align. Variations between the expected schema and the known external context are used to indicate changes in an attached database's structure.

Applications rely on the consistency provided by a uniform internal context to access databases which may have vastly dissimilar table designs. There is no requirement for the internal and external contexts to perfectly align.

Context translations are pre-processed before being received by the Unity server to translate a unique external database into a uniform external context and a standard NetObject transaction.

Like-wise, outgoing NetObject context translations are then post-processed to align with an external database.

The actual table layout that is used to install data and fields in a NetObject can be common to multiple dissimilar database connections. The table layout used by the client is called principal while the actual layout in the target database is called alternate.

Principal database definitions can be pseudo or can belong to an actual database.

DATABASE_AUTOROUTECONTEXT: Autoroute context takes advantage of the common table layout shared by the clients. Transactions associated with multiple dissimilar databases can be automatically routed to a common database when the remote one is not available.

Access to the common database requires no effort on the part of the client since the clients share a single common layout as default. Routing simply defaults to the common database (which already matches form and structure) when the alternate database is not available.

The "model" database to which the external translator is aligned becomes the actual target if the directly referenced context translates to a remote database is not available. The principal database acts as a shared model dictating the way a NetObject is used. As stated earlier, the principal database does not have to exist. External translate context and external auto route context require either an expected data response or an expectation that a database table will be changed.

FIGS. 24-28 and the description below depict the steps in which data is processed when bound for the database from an application as "outbound". Outbound includes updates, inserts, deletes, and requests for data. Data returning from a database request as "inbound" is processed in reverse with the exception that it need not go through the SQL (or other database language) generation process.

Initial set-up is assumed to have been completed allowing the diagram to represent the actual process. The actual set-up requirements are covered elsewhere, with specific focus on the alias objects.

Figure 24:
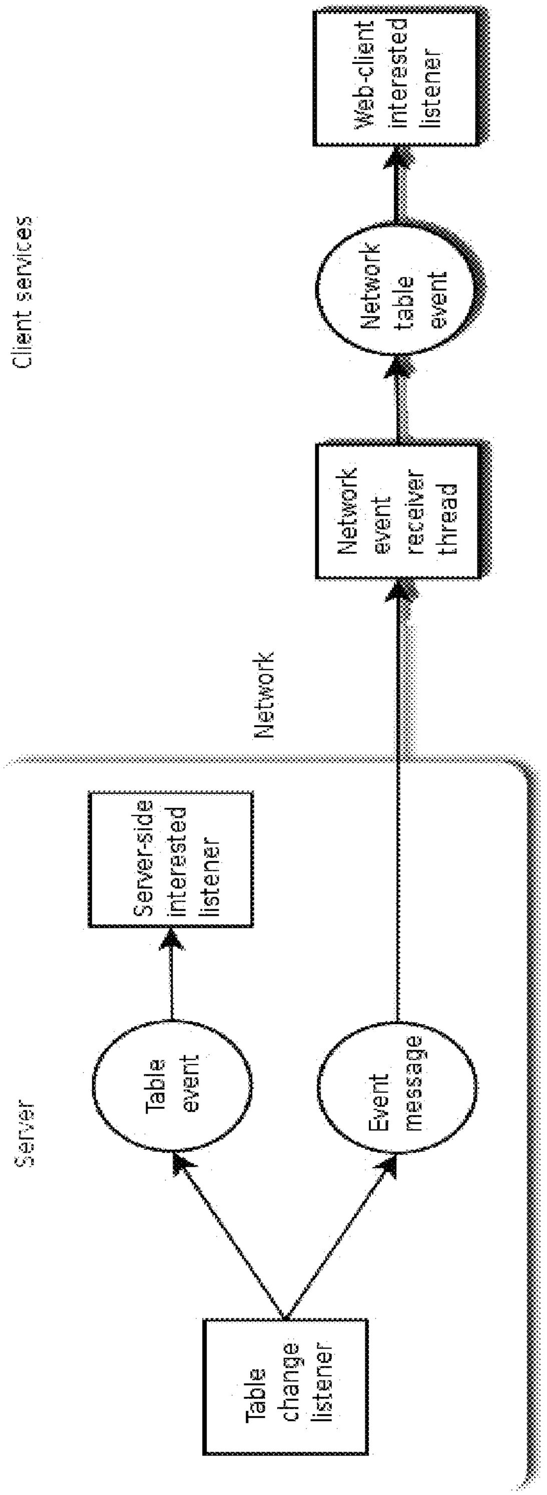
FIG. 24 shows the translation process of one embodiment of the present invention.

Referring to FIG. 24, NetObject processing request 500: NetObject is received over the network (or directly) from an application or device. The preferred process uses the received NetObject as the data transport through the various steps, although the current implementation is capable of operating without an internal NetObject.

Translate connection & connect 502: Referenced external context is translated into a known database connection. The connection is tested for availability. Lack of access to the referenced database connection (by option or connect attempt) will not be an error when autoroute is enabled and a referenced "alternate" database exists. Step 502 translates internal table naming criteria supplied in this NetObject into an external specific AliasTableSpecification translation Object.

Translate command and function 504: NetObject processor translates the expected actions needed to support the database request represented by the received NetObject. Although it is most common for NetObject requests to represent database access, they also represent events and communication.

Find data translation matrix 506: Field by field translation is accomplished by translating the encountered data, type and structure into coordinates in a prepared translation matrix. The matrix is generated at system start using specifications for known database brands and versions.

Update external translation 508: Install external database table naming criteria from translated internal naming criteria. Criteria can include table column names or names at any level in the database schema structure.

Find connected database accent 510: Get the list of parameters that will affect the way the SQL generator assembles code so that it is biased towards a given kind of database manager. The parameters also direct the punctuation of the generated code.

Figure 25:
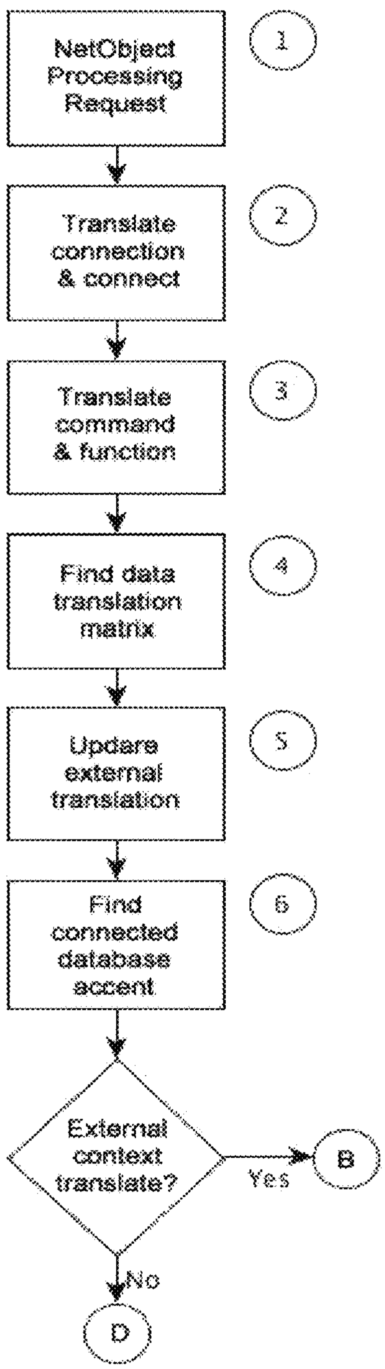
FIG. 25 shows the translation process of one embodiment of the present invention.

Referring to FIG. 25, Context translator 512: Looks for an external context translate in the appropriate alias table specification. If found, then external to external context translation is available.

Alias order translate 514: Reverse translate the current external context into a referenced external context also known as the virtual database. Run the translation through alias order services to convert to virtual references for most any aspect of a database design (tables, columns, etc.).

Replace NetObject context 516: Alter the current NetObject to properly reference either the actual target external context or the virtual reference for an alternate external context.

Process SoftBus 518: Execute rules defining relationships between table columns in two external contexts. Both external contexts can be representation of an actual database. However, one of the two will be considered an alternate and is therefore virtual (does not have to exist).

Figure 26:
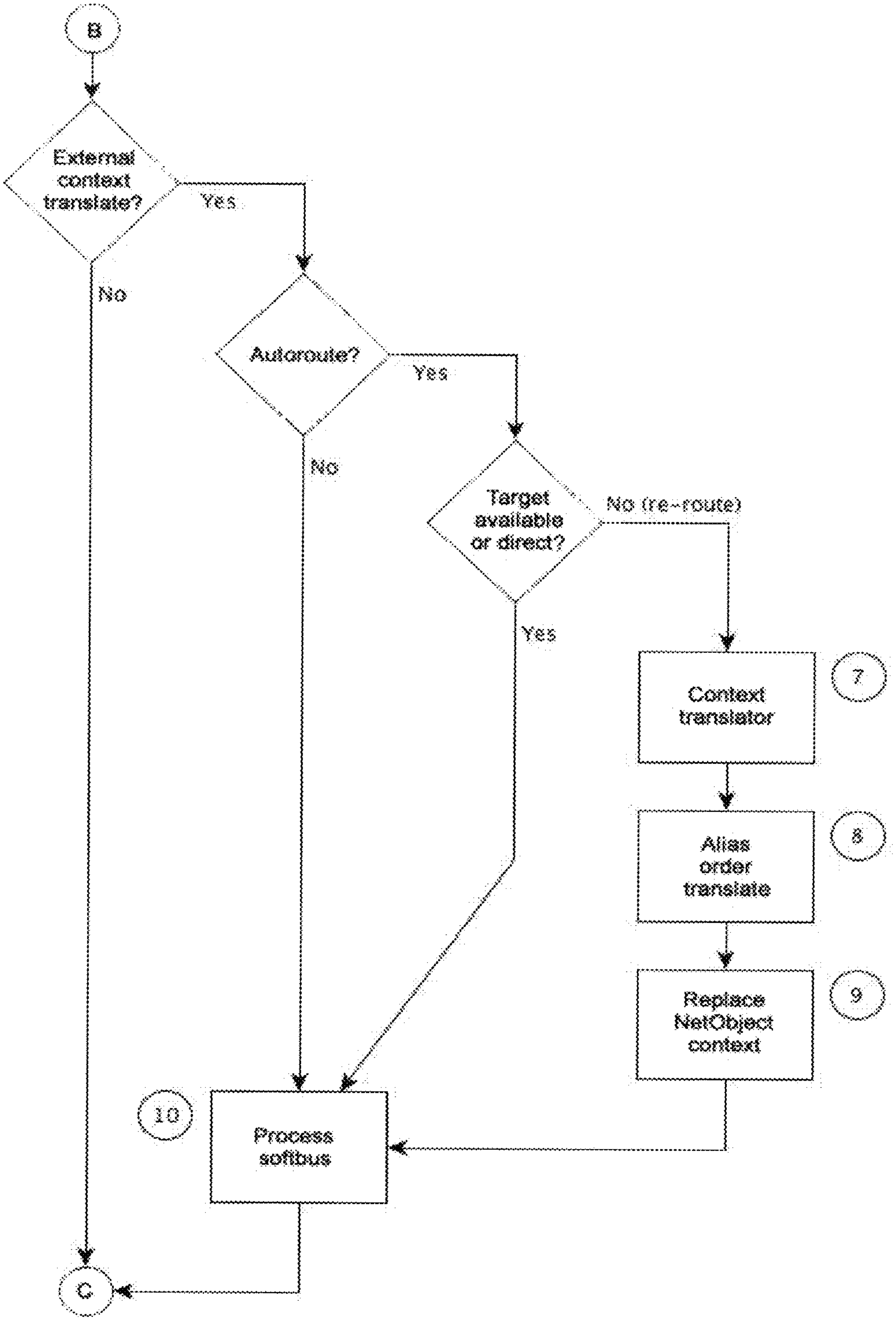
FIG. 26 shows the translation process of one embodiment of the present invention.

Referring to FIG. 26, Translate and order 520: Translate each use of names and establish the expected order. Table specific specifications and data are realigned and renamed for use in a different context. For example, table columns, column types, column names and keying. Field names and column names are relationships are established where one becomes substituted for the other. For example, data element names of the payload data, order control data, keying data or ranging data.

Range value relationships 522: Establish relationships between contexts and convert naming to and from internal and external contexts. For example, names of data elements, order control, keying or ranging names. Establish relationships between data within the target internal context where data and names align as well as related data. For example a few fields of start and end ranges.

Implied re-order processor 524: Reorders ordered values or names for a 3rd list based on inductance where a known 1st list is already related to a 2nd list. Known reorganization of the first list causes the reorganization of the 2nd list as a normal sort. However, the "coincidental" or implied relationship to a third list is also caused to re-order. For example, changing the order of all of the homes on a block would require changing the order of the house numbers. But houses on the next block over are only coincidentally arranged in the same order. Keeping neighbors aligned would require changing the order of the houses on the next block.

Implied re-ordering does not require an exact analog in the implied list as in the two rigidly related lists being re-ordered. For example, a missing field in the implied reference should not cause any problems for the explicitly linked first two lists.

Isolate data and structures by function and translate 526: Isolation and retrieval is processed recursively for the various kinds of data and names. Names are translated as a by-product of isolation followed by retrieval. For example isolating range values precedes retrieving those values. The same is true for most of the data and names being processed. For example, range data, column names, column types, keying data, keying types and the like.

Balance relationships 528: Balanced paired values and names. For example, start and ending range data.

Implied re-order processor 530: See 524 but this time it is only for those names and values which can change existing values in the database (update).

Discriminate columns 532: Perfect list of data to be included in transaction. For example, unchanged data from a previous query will be automatically excluded from transmission during an update. Saving unnecessary network or database overhead.

Figure 27:
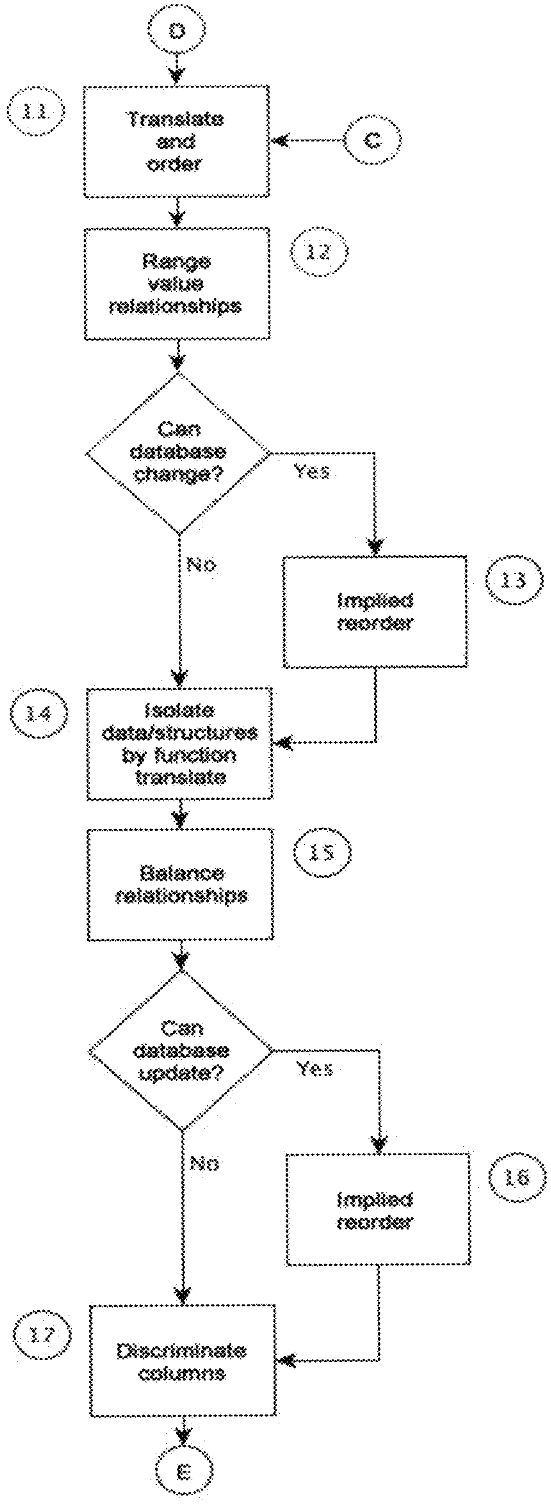
FIG. 27 shows the translation process of one embodiment of the present invention.

Referring to FIG. 27, Perfect order and invert 534: Renumber relative position index so that the numbers are continuous but in the same relative positions as the non-continuous source numbers. Translate current index sequence into its inverse. Set the translated reverse re-ordering sequence suitable for reordering the returned result set external columns back into internal order.

Discriminate columns and values 536: Implements value specific punctuation and finalizes data form. For example, adding quotes to values.

Process database specific accents 538: Re-perfect list to be included in transmission.

Generate SQL 540: Prepare rules and suggestions for SQL generation for a specific brand and version of a database manager. Code or other database interaction vehicle (e.g. XML) is biased to the needs and specifications of a given brand of database.

Request result set 542: Code generator translates prepared NetObject into appropriate command for the target database.

Update NetObject and transmit 544: Returned values from the database manager (if any) and installed in the source NetObject by requesting the data from an internal result set manager. Problems or the fact that there is no returned data are also incorporated into the NetObject for re-transmission. The Completed object is then transmitted back across the network.

Universal Database Administrator (UDA)

The UDA is a GUI tool for managing the Unification Server and other databases. The current state and detail of the translation matrices are available for review. Connections to databases are managed from a tree pane where each connection is listed by a friendly reference name. New connections can be created by replicating models which already contain the needed specifications for a given type of database.

The possible specifications, including IP address, port number, user id and password are added or maintained in a form-like window. The actual connection strings and driver information are pre-listed and can be edited directly. Variables in the form of HTML tags are inserted in the predefined connections string and drivers where the supplied values will be inserted.

New connections generate "orphans" which can then be assigned to an internal context. Connections in which the system already knows how to generate the context will automatically do so. Context and naming can be altered via the GUI at any time including while the system is running. Metadata for the external databases is also available. The Unity server also allows direct manipulation of the connected database.

The display reflects that actual state of the server and not simply the last change made by the user. The GUI data editing and the display are managed separately and do not rely on one another for timing or data. Thus, the display can accurately reflect the actual translation matrices and database information.

Operational Theory

Updates to the encapsulated TreeUtilities Objects are triggered only when this class receives a Volunteer event from the server. The events come in the form of unidirectional message which is consumed by the attached Client Object.

Changes to the server system database tables are only recognized when they are accomplished through the server and then only when a NetObject is used to request the change.

This class uses the Client class as its communication service to the database.

Figure 28:
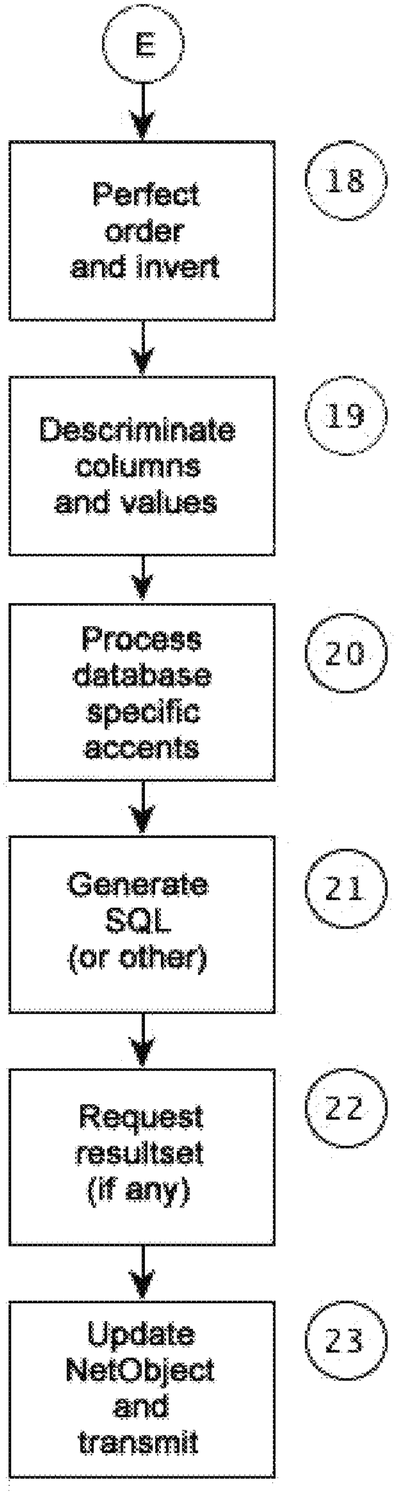
FIG. 28 shows the unification process of one embodiment of the present invention.

Changes made to the server system database tables from this class are not automatically reflected in the tree controls. Changes are reflected when this class receives the Volunteer event from the server. Reflecting the changes in this manner enables the display to only reflect the actual state of the database tables and not just the local request for that change. As shown in FIG. 28, collaboration is also possible since database changes are reflected each time a network-based event is received.

Implementation

It is important to note that the UniversalDatabaseAdministrator does not display changes made by the user in any of the navigation trees. The trees only reflect the actual known state of the database to insure and accurate synchronization and representation to the user.

Assured synchronization is accomplished by a closed loop of events initiated by the administrator to tell the server to make a given change. Successful changes generating events from the server which the administrator listens. Changes to the navigational trees are then made in reaction to a received event from the server.

This distinction is important because the user may notice the delay between the time a change is made and the time which is displayed in one of the trees. Also, it is possible for change not to be displayed should the request have failed at the server.

There is a special thread running of the class NetworkEventReceiver which translates messages from the server into network cable change events for which this class listens. Network table events are unique and that they do not start out as an event, they are generated as a simple communication message which has to be converted into an event by a receiver. Messages are created by the command processor on the server-side and immediately handed over for network transportation to the client side.

Virtual Logic

The system acts like an amorphous logic engine that can be implemented on a machine in a network (including direct access as a client). The Virtual Logic Server melds two technological approaches to application generation: 1) Object interpreter 2) Useorder interpreter. The Object Interpreter technology is an interpreter that is driven by flat records, where each of the records contains a fixed number of fields. Each visible object to be installed on the pasteboard is represented by one of these records with a fixed number of fields. These visible objects are instances of a given widget, when taken together represent a collection. The collection does not exist in the same sense as a program/class file or as a single data record. It only exists by virtue of a populated set of widgets which have been assigned to the same collection. For example; a simple collection that acts as a program with two screen labels and two fields as shown in FIGS. 29 and 30.

Figure 29:
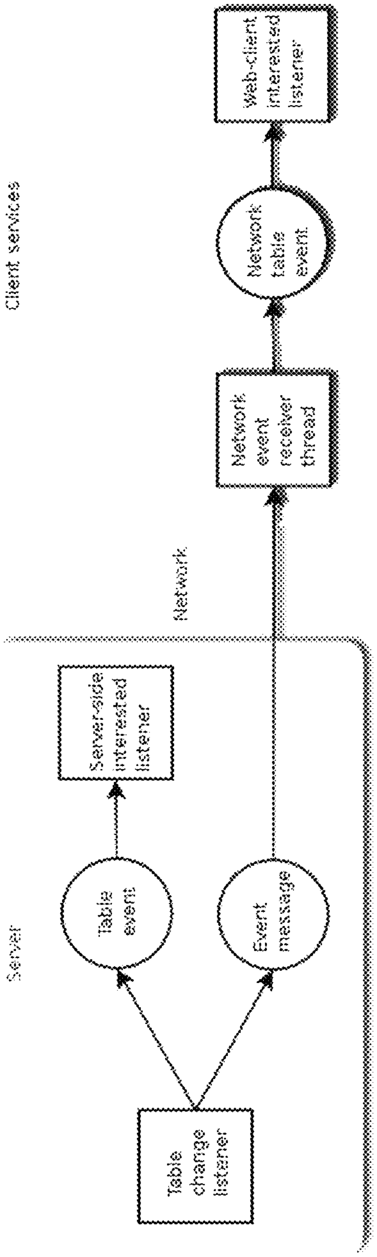
FIG. 29 shows an Async network events of one embodiment of the present invention.
Figure 30:
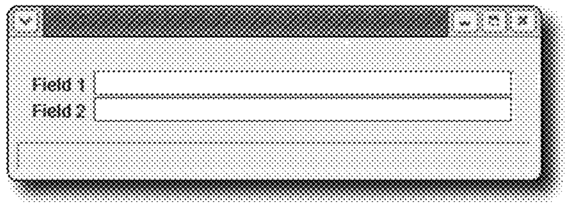
FIG. 30 shows an example of a virtual program of one embodiment of the present invention.

In the example shown in FIGS. 29 and 30, our fields and labels seem to be hanging in space without a relationship to one another. This is true to the point that there is no physical representation for a collection (or Virtual Program). However, there is a reference to the same collection in each of the stand-alone widget instances. Construction of a Virtual program declares that the virtual program exists. The existence of a given program within its universe is known by its relationship with the rest of a virtual environment. The program which interacts with the user is driven by one or more Collection of Structures, but is named as the combination of Virtual System, Virtual Application, Virtual Collection and Virtual Structure. The virtual environment is the hierarchy from the Virtual System point of view. Virtual Programs are the same hierarchy from a single Virtual Structure point of view (in reality system+application+collection+structure) also known as the internal context.

Figure 31:
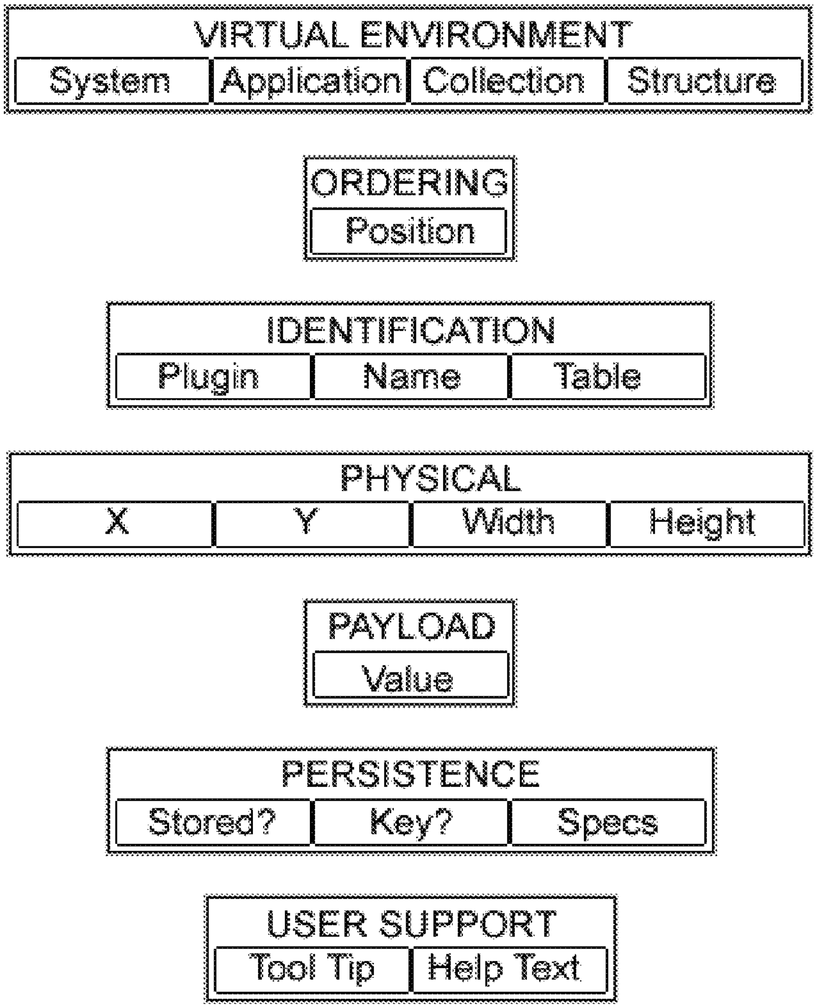
FIG. 31 shows a virtual structure of one embodiment of the present invention.
Figure 41:
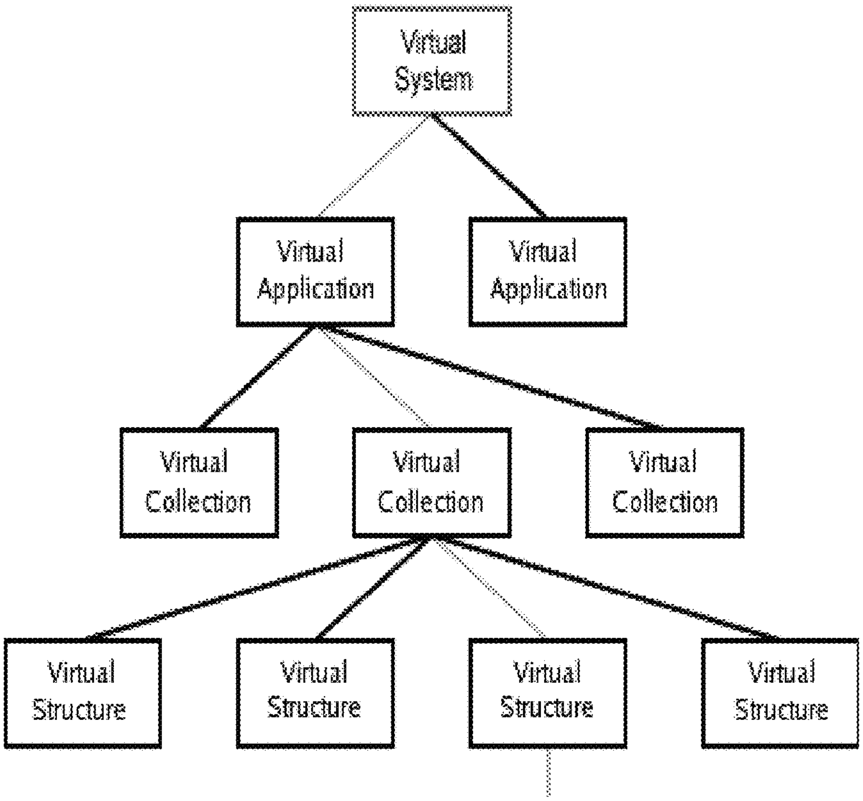
FIG. 41 shows a hierarchy defining the existence of a virtual program of one embodiment of the present invention.

Referring to FIG. 31, organizing a specific virtual environment or existence is hierarchical starting first with Virtual System as the most general and last with the Virtual Structure as the most specific (FIG. 41). The level of specificity increases (more fine grained) as more of the existence fields are used. Any form of process can be synthetically created by the system, for example, processes, reports, screens, communication or device control.

The organization defining virtual existence supports the development of Virtual Programs by a designer and is required internally for the Instigator to navigate. User-level Virtual Program execution does not have to be related to the existence defining structure. It is possible to have Virtual Structures from various parts of the hierarchy executing as a single seamless entity in front of an end-user.

Virtual Programs, when taken by themselves, do not have any physical form. For example; starting a Virtual Program which does not contain any objects will not produce anything. The activities of a program are defined by adding Widgets from a collection of Widgets. The Widgets are proxies representing specific molecular structures. The molecular structures can be fluid or can be a simple and fixed set of molecules. It is the collection and relationships of the molecules that becomes the process which acts like a program. Widgets represent the physical objects. Useorder represents the actions to be taken on the physical objects. Widgets are attached to a given Virtual program. Useorder can then be associated with a given Widget (see FIG. 32). Useorder can also be associated with other things including but not limited to a Virtual program. Useorder will be discussed in greater detail below.

Widgets & Molecules

The contents of a Virtual Program record will be discussed. Each Virtual Program record represents a single Widget. Each Widget has five areas of information in its definition: Identification, behavior, physicality, data and user support. For the purposes of this document, the synthesized program is an example simple screen/window.

Identification:

There must be an object added to the Virtual Program for each program part of program behavior. The identification could be considered a place to put a Feature. The place contains other specifications that will be used by the system to enact a Feature, including but not limited to display dimensions or processing order. Identification includes System, application, structure, collection and position.

System:

Virtual Programs and Virtual Tables are identified by name and the virtual system and application within which the Virtual Programs and Virtual Tables reside. Each virtual program or table is assigned a unique name when the program or virtual table is specified. Names need only be unique within the combination of system and application. The same name may be used in conjunction with other systems and other applications.

Table names do not have to be the same as Virtual Program names and do not have to follow any prescribed computer-based naming. For example; spaces can be included in the name.

Application:

Names for applications and systems have meaning in conjunction with the name of a virtual programmer table. The names for applications and systems serve to organize systems and data.

Collection:

Each virtual program is assigned a unique name when the program is specified. Both database tables and Virtual Collections share the same level in the internal naming hierarchy.-Virtual programs represent objects and their related actions. Virtual Tables represent translations to actual tables in an implemented Database Management System.

Structure:

Collections which share the same name, but have differing Structures, are assumed to be related within the same Application. Such collections perform very different kinds of mechanical functions. For example; a Database Table named Customers is the same conceptual level as a Virtual Program also called Customers. Structure could also have been called application discipline because a given collection may be called upon to perform the equivalent functions as normal computer programs written by programmers trained in a variety of disciplines including but not limited to communications, process control, and tabular accounting. The Structure identifies and separates the purpose of a given definition within a Collection.

Position:

The Useorder order provides a control on the order of things and events. The Userorder establishes a sequence in which data is stored or in which tasks are performed. For example, the Useorder can number a set of stored fields. The field with the lowest number will be stored first in the record. Each successive number assigned by Useorder will determine the positioning of the field in the record. In another example, a user attaches multiple features to a single screen field. The behavior engendered by the Useorder numbers would cause the behavior of the feature with the lowest number to occur first.

Behavior:

Features represent the smallest possible part of a program and act as building blocks empowering a user to create a very wide range of Virtual Programs. Behavior includes Widget, object name and internal context (data unaware method for access information from disparate database and sources.

Widget:

There are a fixed number of molecule-sized behaviors from which to create a desired total behavior. For example, WidgetButton is a graphical button from which a user may make the desired number of buttons on a given screen. Widgets can be any molecular computer function.

Object Name:

Objects that are part of a virtual program must have a unique name. For example, a user may create My_button and button_number_2 using WidgetButton.

Database Table:

Some objects represent actual data location in a database or a unified virtual database. There are also cases where it is possible for an object or set of objects to represent both a location in memory and a location in a database, such as a stored field. In these cases, the name of the object is actually the combination of the field name and the name of the database table (or file). For example; the stored field Vendor Name would have to be associated with a place in which it is stored: Vendor Name: Vendor File. The same is true if the data element is attached to a specific communications channel or message name including but not limited to Robot Identification Code: Com23.

Physicality:

Physicality may not apply to all objects added by a user. Screen coordinates may be needed when an object is to be displayed on the screen. Likewise, width and height apply to screens. Width may also apply to data sizes. Features represent the smallest possible part of a program and act as building blocks empowering a user to create a very wide range of Virtual Programs. Physicality includes physical dimensions and locations.

Useorder Interpreter

Figure 32:
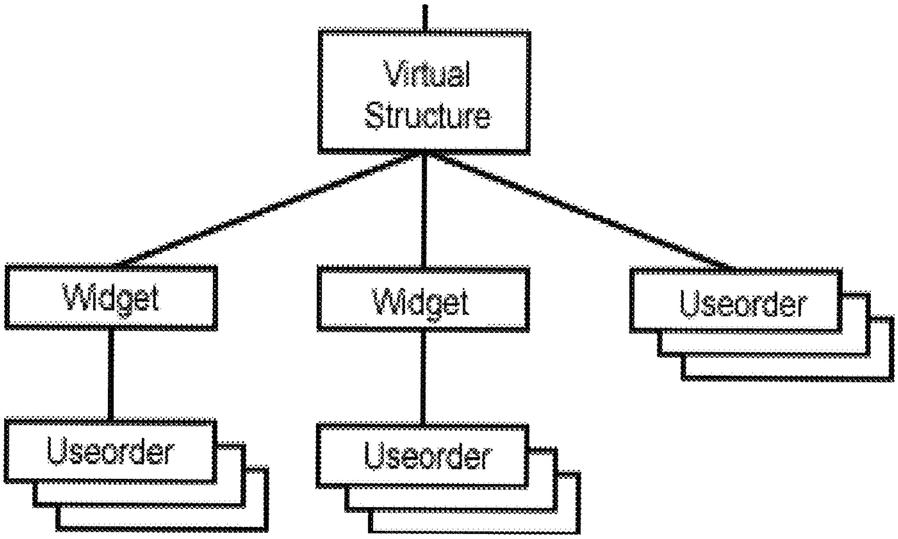
FIG. 32 shows an anchor widget of one embodiment of the present invention.

Referring to FIG. 32, the second melded technology is more dynamic but requires a sophisticated system from which to operate. The Useorder Processor combines grouped elemental behaviors into behavior sets of functional behaviors. The elemental behaviors may be used in combination with other elemental behaviors. A recognizable and useful behavior can be achieved when some of the elemental behaviors are combined.

The sets of combined elemental behaviors are attached to an instance of a given widget to which the combined elemental behaviors lend their behavior. A given synthesized program is the collection which juxtaposes instances of widgets with combined sets of elemental behaviors. Each widget in a set of widget instances, while taken together, represents a collection. The individual widgets also act as the connection point for sets of combined elemental behaviors. Thus, these widgets are called "anchors".

Each of the elemental behaviors is recorded as a "Useorder" and is represented by individual records defining a collection. The "payload" of these records is two sets of two fields.

The first value in each of the two Useorder payload fields contains a word or phrase and then a database reference. The second set of Useorder payload fields contains a reference to another element. The combination of the two sets defines an ordered hierarchy.

Each of these Useorder records represents two relationships; 1) the one-to-many juxtaposition of the Useorder record in relation to other Useorder records within the same collection and 2) the one-to-one relationship created by virtue of the physical fields within the Useorder record.

Synthetic Programs

The system synthesizes applications that execute over the Internet without having actual program code transferred over the web. The results include a major reduction in the size of the "program" and time required to initiate the operation of a session. Only text is actually communicated, so it would be possible to backup and send a "program" in the body of an e-mail. Applications become "boiled down" to their most elemental specifications. These specifications do not include any of the traditional "overhead" of a program and only contain the small amount of information that is unique to a given function.

Functions can include anything from the ability to update a database table to displaying an input field on the user's screen (via the web and the user's browser).

Other very small programs are started by an "instigator" program, which project themselves into the operations space of the reference-free, small central program. The central program acts as a "place holder" for memory based activities that will appear to be a single homogeneous program to the user.

Each of the small programs that have projected themselves into the central program is simple, reusable functions. These functions represent the smallest possible component of a running program including but not limited to the ability to out a label on the screen, or the ability to restrict data entry to only numbers.

These independent programs run as separate computer programs that communicate through the central program. The independent programs allow usage of other copies of the same program in each part of any application in which that particular atomic ability is needed. For example, placing a label on any screen in any system which is synthesized by this system would use only the same little program as the vehicle to present that label. Another benefit includes running family of copies of the little programs are only seen through the static central program giving the appearance of a single homogeneous program to the user.

Molecularity

Figure 33:
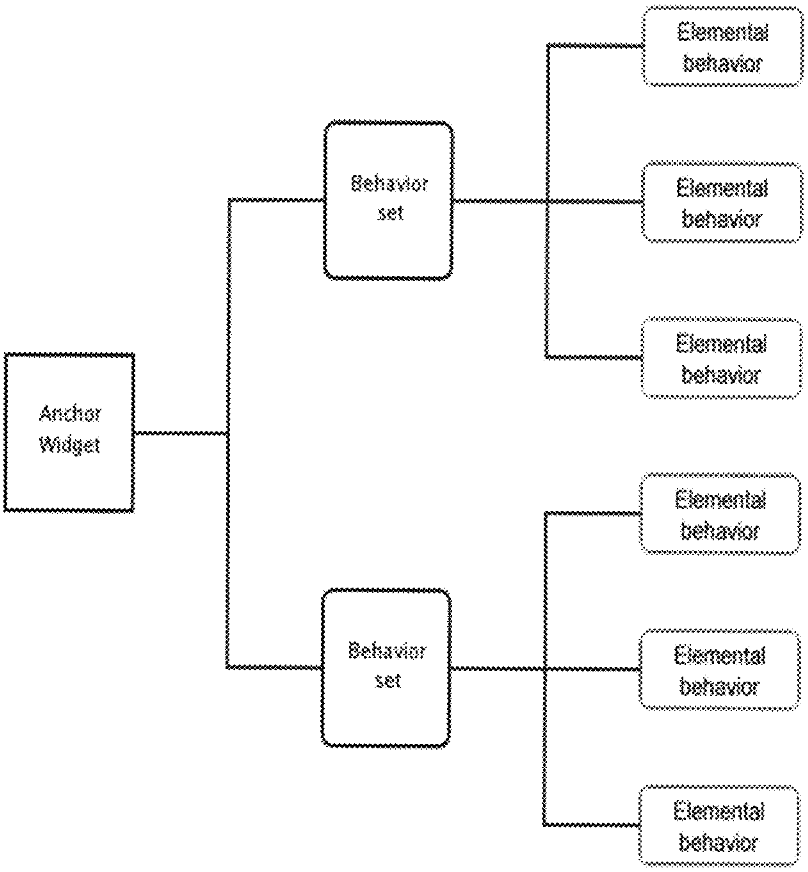
FIG. 33 shows a feature block of one embodiment of the present invention.

Referring to FIG. 33, these are "stackable" feature building blocks that automatically know how to pass information from the block on top through all of the blocks and into the system. The root block may have special responsibility.

The stackable feature technique blends SoftBus and feature packets. Each feature is molecularized to a level of single sub-function that has one input, one output and can interact with one variable. The "related" values correspond to the last field in the useorder table. The system uses the related values as a reference to direct the behavior of the molecularized feature. The related values are simple text. The data type is known by the feature such that the system does not require special marks to identify the data type. "Reserved nouns" also appear as simple text such that the system does not require any special marks to identify the data type.

Figure 34:
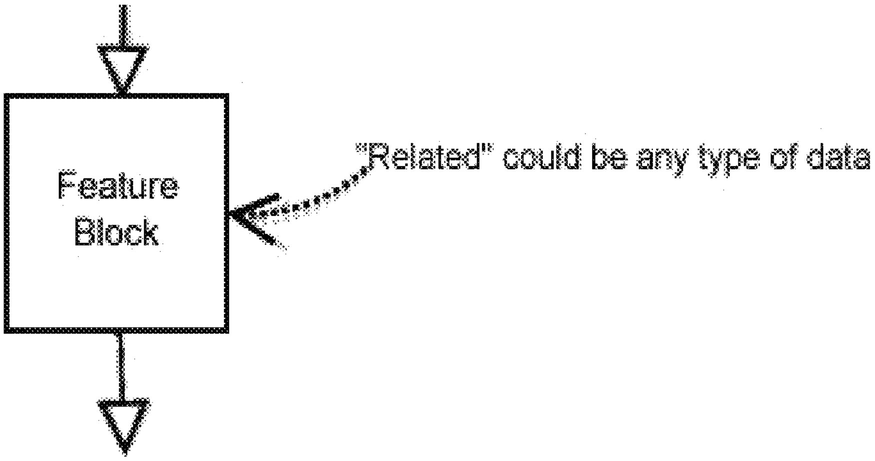
FIG. 34 shows a root object process of one embodiment of the present invention.

Referring to FIG. 34, information or decisions flow from the top of the feature stack starting at an object that has been rendered in the "desire editor, such as adding maximum and minimum values to a field.

Figure 35:
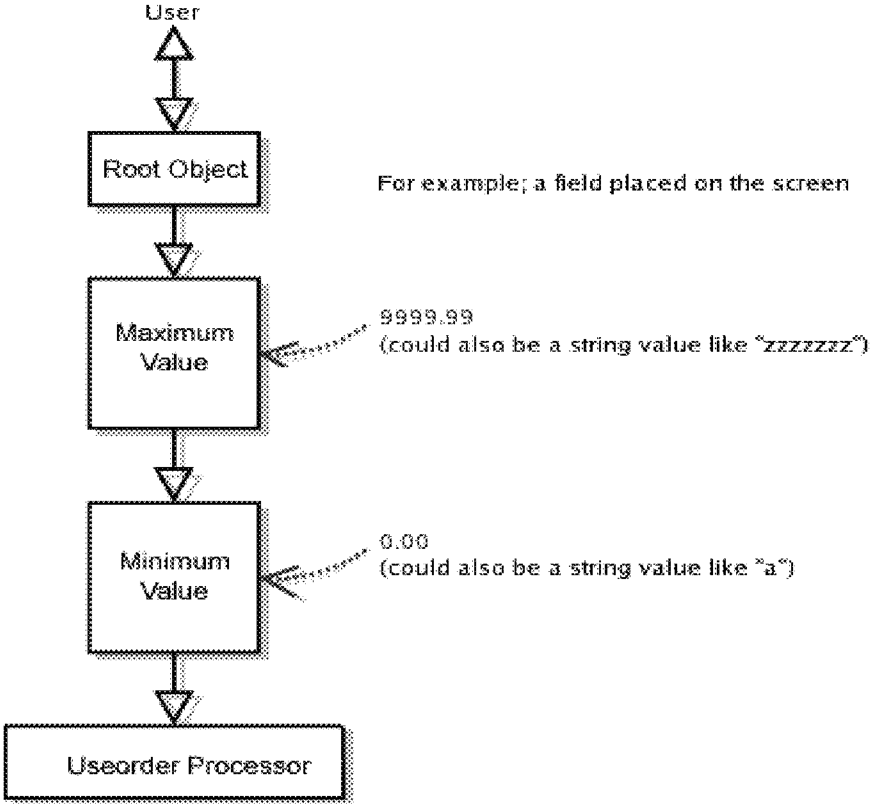
FIG. 35 shows a root object process of one embodiment of the present invention.

FIG. 35 shows how the stack of features would interact when relaying information provided by the user. There is also a need to process information that is being presented to the user. For example; in accounting the general ledger account (account id code) can be presented "masked" so as to automatically segregate its parts, the account code "1234567" using mask "##-####-#" would then display as "12-3456-7". The same can be seen in social security numbers, telephone numbers and postal codes. Some masking may need to consider changes caused by data storage in different regions, such as internationally, as the data storage may differ regionally.

Figure 36:
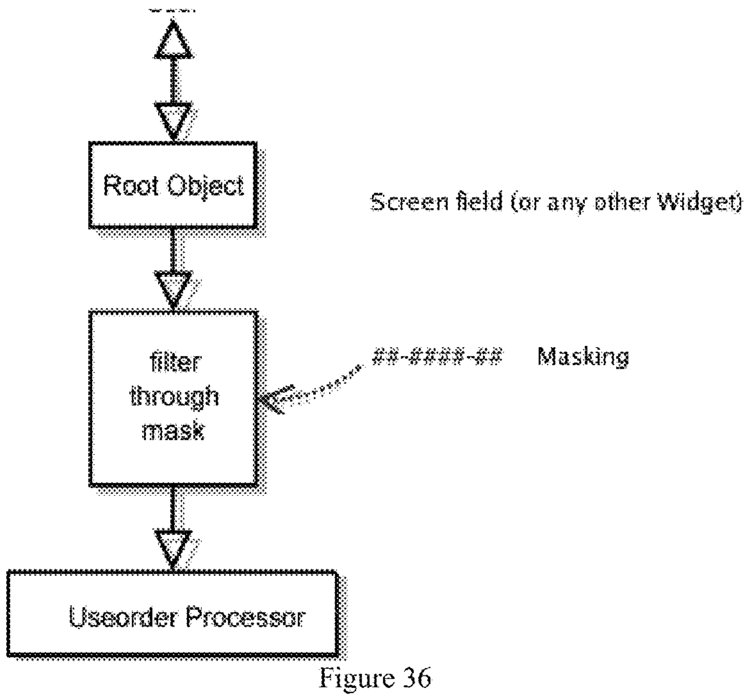
FIG. 36 shows a root object process of one embodiment of the present invention.

Referring to FIG. 36, another possible use would be in multi-language (human language) where the feature has a list of the same words in different languages. Since features would contain any text that is displayed to the user, the application would only need to send a code representing which language to present.

In this example, the use order processor sends a number from 1 to 5 instead of sending the actual text. For example, the use order processor may send the number 3 such that the label would be marked with the text "introduction".

Figure 37:
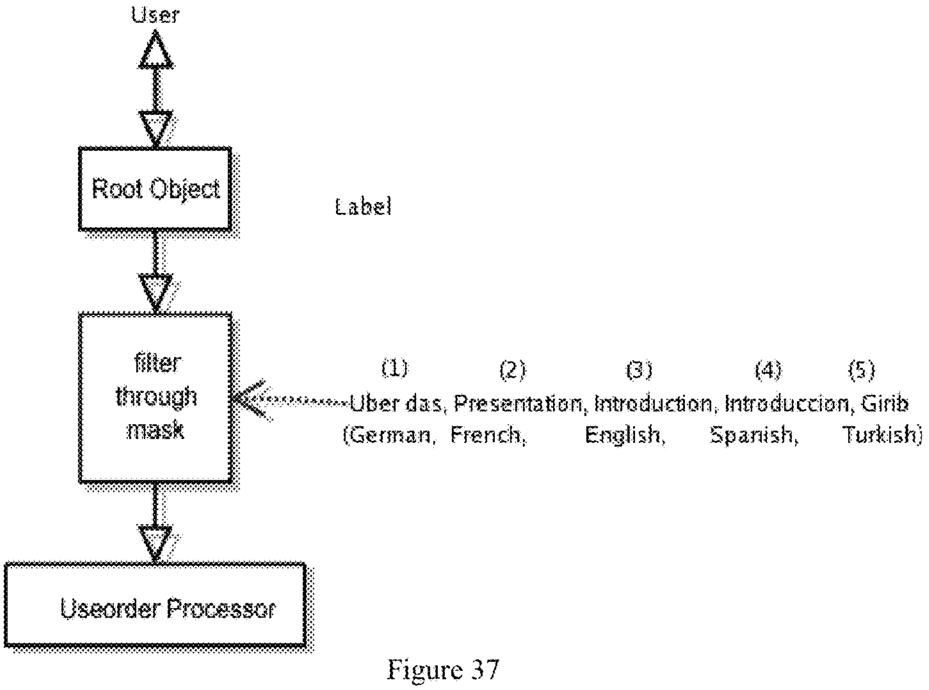
FIG. 37 shows a root object process of one embodiment of the present invention.

Referring to FIG. 37, the bus channels carry data between the blocks for a given instance. The same channels are then re-used for the next set of blocks. The blocks choose the input and output channels (and any in between) from soft specifications. It is also possible for a channel to be declared shared between blocks and therefore already have values when a set of blocks starts. Molecular structures defined by the widgets, which act as programs, then interact with the bus channels via the blocks.

Multiple use of the same feature: In certain instances, the sum of the effects of the same features placed multiple times in the same use order will be additive (logical and) or subtractive (logical or). For example, the net effect of this stack makes the system reject a user's entry in this field if the entry contains a "-" or "H" or starts with "!" or ends with "\".

Useorder in the Desire Editor

Each building block is represented in a table of available widgets.

Order Precedence

Columns of these building blocks are, in themselves, objects as such, they can have uses that determine their execution order.

Copies of used building blocks stored as "objects" could be added to other fields from an object store. These uses of features would automatically correct for local conditions. For example, if the new field is a different data type then the original filed from which the use order was copied, a prompt would ask the user for new values for any feature which contained a now invalid specification.

Communication between the molecules can take many forms including but not limited to "independent process" relationships, Inter-atomic program communications, Major events during startup, and Major events "inside" a Virtual Program.

Use Order's Organizational Representation

Use Orders contain multiple addressing mechanisms. Use Orders can be categorized as "coming from", "organization" and "going to". When viewed as part of the larger system, the addressing mechanisms provide a chronological sequence. From a chronological view, the use order describes "what came before", "what is happening now", and "what will happen soon". Normally this kind of data would be organized into a "tree" structure with a single common root node and the nodes would be related via a linked list. Organizing data into a tree structure allows for a single multidimensional representation of data.

Figure 38:
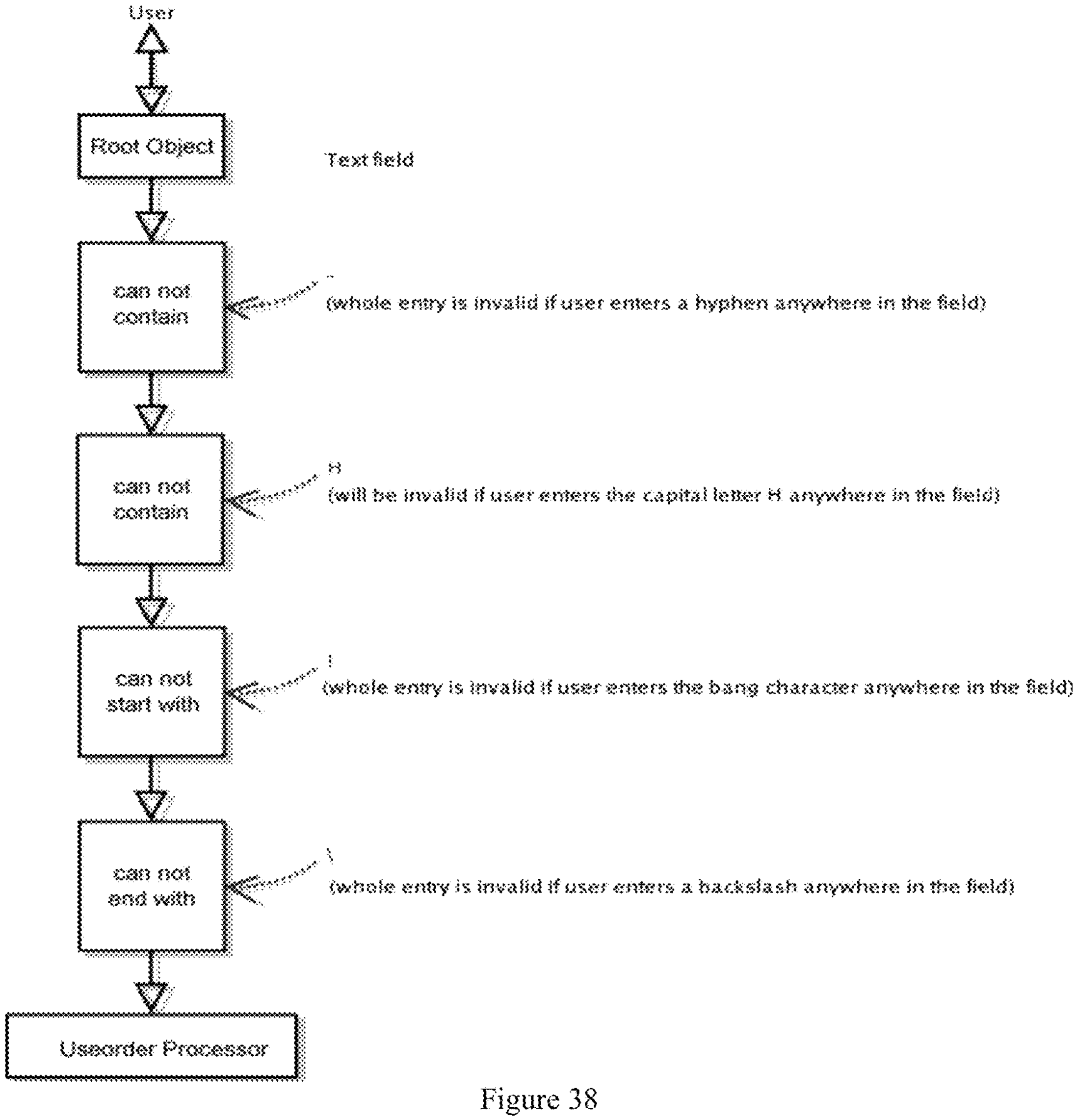
FIG. 38 shows a representation of data of one embodiment of the present invention.

Referring to FIG. 38, the Synthesizer needs unrelated clumps of data that are multidimensional which allows free-floating concepts that may or may not be represented in the same number of dimensions. The organizational relationships can opt to become related based on external stimuli. This data representation allows these optional and possibly temporary relations to occur cross structure. The same form of relationships in a standard tree structure would appear as random connections between nodes that do not follow the tree's branches. The relationships could also be viewed as multiple root nodes. The finer levels of granularity can become related. To make all of this work, the present invention creates ad-hoc link lists that differ from the current representation of the data. Each of the nodes will independently know its relative location in the multidimensional hierarchy.

Figure 39:
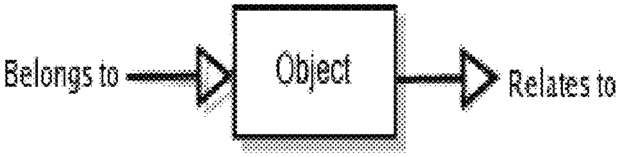
FIG. 39 shows a representation of data of one embodiment of the present invention.

FIG. 39 shows a single node's understanding of its place in the ordered representation. The model creates a rigid structure as a normal tree representation. New nodes can be created that relate existing nodes to add the dynamics discussed earlier. The "Relates to" reference creates local relationships. The new nodes can be created and deleted at will creating any number of relationships between any number of nodes. The system can operate with a smaller set of values for example; context without structure, a single ordering value, and ordered objects System:

Highest level of organization to which this Virtual Program is a member. Automated activities are usually arranged so that there are identifiable groups of software that has a natural and easy to understand relationship including but not limited Business Accounting or Satellite Administration. Systems are related sets of applications which are designed to work together for a unique common objective. Operational synergy can be established. For example, an accounting system could include the related applications: Accounts Payable, General Ledger, Accounts Receivable, Payroll, Sales Order, Purchasing, etc.

Application:

Software is arranged into groups within a given System. Each group represents a top level function of the System. A System includes general functions called applications. Applications are collections of virtual programs that, together address a common, definable need. Such programs include Accounts Payable, Payroll in a Business System, Word Processing, or Spread Sheet inside a productivity System Collection:

sets of objects that collectively form a recognizable component of a given system including but not limited to a program or a database table. These specifications, when taken as a set, can synthesize a virtual program. The virtual program simplifies the process of making operational changes and improves the speed in which the virtual program can be determined across the Internet.

Structure: Identifies a complete and functional Collection which may share the same name as another fully functional Collection but service a different computing Discipline. Collections which share the same name, but have differing Structures are assumed to be related within the same Application, but perform very different kinds of mechanical functions. For example, a Database Table named "Customers" is the same conceptual level as a Virtual Program also called "Customers". Structure could also have been called application discipline because a given collection may be called upon to perform the equivalent functions as normal computer programs written by programmers trained in a variety of disciplines including but not limited to communications, process control, or tabular accounting. The Structure identifies and separates the purpose of a given definition within a Collection.

Internal Context: System, application and collection can be referenced together as an "internal context". The internal context can be identifies as field 1, 2 and 3. The combination of a set of values creates a contextual relationship. Parent: a Virtual Program includes the objects (or components) that the system will use to synthesize an operational application. An operational synthetic application may also require access to a database or device which must also be synthesized or referenced synthetically.

The system environment must synthesize the program that is presented and interacts with a user, other programs or devices. In addition the environment must synthesize the functions that are normally performed by programs interacting with the database. Therefore, any given object being ordered in a Useorder could be a member of a program or other system function.

Objects are also connected to a given virtual program or virtual function less directly. While a data field is connected directly to a virtual program that is appropriately represented in the virtual programs Useorder, objects may add or affect the behavior of that field, such as placing a minimum or maximum value that can be accepted by the field. These objects may use all of the same machinery that the field object uses. Their object reference is the same as the field to which the object references are attached. For example, assuming a data field on a screen called CUSTOMER_ID, this object would be used normally for a given collection. The objects that will set the desired behavior for our example field can be added to the same object which represents CUSTOMER_ID. The object is still the same CUSTOMER_ID, the only difference will be the specifications that are being used. Any given used feature, which acts upon a given defined object, must be attached to that given defined object. In this way the correct behavior is attributed to the correct defined object. There are other kinds of used objects that are attached to the Virtual Program globally and not to a specific object.

There is no requirement for a parent Object when an object being used is the Root or top level [of a set of objects that appear to the eventual end user as a single programmatic component]. Used objects are arranged in a node network that forms a pattern that looks like a tree. The root object is the first node in the node network, as such there can only be one root node. A root node must exist for anchoring the node network.

Bundle: Relative execution timing. Bundles are one or more Useorder sets that are executed at the same time. The execution order is the same as the order in which the Useorder sets exist in the bundle. For example; a bundle could be all of the Useorder sets that should execute when a field gains or loses keyboard focus.

Ordered:

Name of the Useorder which may contain one or more ordered entries. Ordered entries are referenced in sets which either represent an order or state the existence of programmatic activities. Orders can define the relative position of an item within a list including but not limited to the relative position of fields (table columns) in persistent storage or the order in which processes are to be executed. Orders can define the existence of an object in a set. For example, an order can determine if any numeric fields exist. Orders can represent definitions such as the data type of a given database column (field).

Position:

Ordering list in which the relative position determines event Useorder. Position within a Useorder normally represents a relative order within a list. Unordered lists can also be represented, in which case the initial order would be arbitrary.

Instance: The same named order can be applied to the same Anchor Widget and in the same bundle as many items as needed. A sequential suborder is automatically assigned each time the same Useorder name duplicated. Instances allow for duplicate Useorder names and provide a way to specify the order in which the duplicated names are executed.

Object

Any object can be used in the following examples: the fields defined in a database table or an event order of factory supplied functions that have been attached to a defined field. Uses cause the ordering of events or data so that the Applications Environment can direct process features to process activities in a prescribed order or arrange data in a specific order. Uses must be named as a mechanism to enforce a list of known standards creating a reliable environment from which to direct real-time processing. The name becomes the method to find and to direct specific characteristics of a given program.

Selected names should have a clear relationship to the function of the Useorder and should be descriptive of the Useorder entries processing or ordering effect. A Useorder name of one embodiment should include a subject matter without alluding to any other function. This naming purity helps clarify the reasoning for creating the new Useorder.

Related:

Frequently a single Useorder entry requires a pair of values to properly establish a relationship such as a field name in a database that requires the name of the database table. Only with both paired values can a process find the correct field.

Most Useorder entries order actual data or processes. A Useorder may also order other Useorders. Infinity deep logical trees can be established by sequentially linking a parent use with another Userorder as its child. For example, multiple orders could be loaded when the system switches into Edit mode. Some of these orders do not have a natural relationship with one another, for example; can be in different parents. Loading unrelated orders can be defined as a Useorder which defines a relationship between otherwise unrelated orders. For example, the orders defining detail atoms should load as well as the names of the molecules when switching to Edit mode.

Target Object:

Relationships can be establishment between any defined objects.

Uses cause the ordering of events or data so that the Applications Environment can direct process features to process activities in a prescribed order or arrange data in a specific order. Uses must be named as a mechanism to enforce a list of known standards creating a reliable environment from which to direct real-time processing. The name becomes the method to find and to direct specific characteristics of a given program.

Selected names should have a clear relationship to the function of the Useorder and should be descriptive of the Useorder entries processing or ordering effect. The Useorder name of one embodiment should include only one subject matter without alluding to any other function. This naming purity helps clarify the reasoning for creating the new Useorder.

Target Related:

Frequently a single Useorder entry requires a pair of values to properly establish a relationship. For example a field name in a database also requires the name of the database table before a process would be able to use the field name.

Virtual Program Component

There are two distinct components in virtual program synthesizer, one called the instigator. The second interprets atomic elements that make up the definition for programs actions and behaviors.—

One method for embodying system design provides the instigator with a shortened list. A GUI interface representing the design would operate more quickly but would have built-in limitations in size and scope. Using a shortened list, a GUI could represent a synthetic object with a graphical object on the screen.

The preferred method uses a Useorder to represent an object. The Useorder can be used to define virtually any behavior and system. Useorder can be thought of the atomic particles, or each particle is an element of the most elemental material. Defining behavior using Useorders allows for a very granular definition of how any process or object becomes assembled. Objects can then be built (at runtime) on-the-fly to match the needs in any given synthetic program.

Synthetic Programs

The processor executes complex Useorder which contain multiple sub-Useorder (in a single loop). The in-memory array which contains the current Useorder sets is processed from start to end. The Useorder sets look for and react to Useorder entries that match the testing logic at the various depths of the horizontal Useorder record (starting left and going right). Therefore, only the Useorder entries that are related to the current environment are processed even though all of the use orders are examined. This is the same as creating a sub-set of the current Useorder array and then processing the sub-set. To create the sub-set, the system must process the complete in-memory array in the same way as it would process the logic to follow in the sub-set that would result in another array containing only the Useorder entries to be processed. The system could then process the sub-set with less logic.

The added complexity in processing actual logic and the inefficiency of double processing support encourages processing the entire array each time and then to act on only those Useorder entries that direct such action as the array is being processed. A preferred implementation includes all levels of granularity. Some Useorder processes may reference Useorders outside of the defined synthetic program. For example inter-application integration may represent the movement of data between two otherwise unrelated sets of synthetic programs.

Useorder Processor

Parent Useorder entries are not intended to be used to start a process outside of the processor. Only child Useorder entries start external functions. The parent entries allow the system to point to a single entry that is translated by the Useorder processor translate into a list of activities. The relationship between the Parent Useorder and child Useorder entries is a one to many relationship where the parent Useorder entry acts like a header and the many children Useorder entries act as if they are detail. Parent Useorders can be found using child orders. The orders are keyed by the synthetic context of the program and are therefore easy to find.

Useorder processing is capable of synthesizing computing tasks. To capitalize on the processor's power, a given collection of child (the many) Useorder can represent any active function. The function can, but does not have to, relate to the anchor object to which the parent Useorder entry is attached. Uses are constructed as an n dimensional array in the form of a hybrid node-network. Traditionally the normal inter-node relations are accomplished by assigning sequential numbers as a "node id" then the relationship is defined by having two fields in every node: 1 the id of the parent node and the current node's ID. The node that acts as a tree root for the whole node network has no parent ID. For example; where: ([parent node], [child node]):

In the Application Synthesizer, the node network has more than two coordinates to construct a structure that will dictate hierarchy at run time. The system uses the traditional node network tree. However, many such trees relate to one another in a global universe. Three coordinates that structure a multidimensional matrix used by the system creates a three dimensional space. Each of these spaces has its own node network. This method is faster and well suited for this application. The three coordinates exist as the first three fields in a horizontal record (table row) where these fields classify the system definitions into System, application and collection.

Rudimentary Example Organization

It is differing degrees of granularity similar to the vagaries of beach sand, with a concept that starts by looking at all of the sand as a single group and then another concept that looks at general divisions in the (or classifications) in the sand. It takes of few levels of this sort of categorization to drill down to a level that contains anything physical, in our example sand. The classifications are needed to allow the synergy application of computing ability (as imparted by the installed software). For example; while disparate systems may upon occasion be called upon to communicate or work together, applications within a system share and process as a family of abilities.

System:

Hard-coded software systems are comprised from a known, fixed set of identifiable software "parts". For example; in an office productivity suite (or System) may include a word processor, spread sheet, data base manager, graphics and presentation applications.

A System is the loose coalition of similarly minded software application products. The "System's" functionality is harbored in the separate, identifiable applications. However, information may be shared and even synergistically managed by combining features in the different applications from which the System is comprised.

Application:

Modern computer applications are normally too complex to be implemented as a single program or a small collection of programs. An Application is identified by the characteristic that all of its functions are aimed at a single, identifiable work set that has an analog in the physical world. For example, word processing has the analog of humans writing and editing documents. Accounts Payable has the analog of an accountant keeping a paper payables ledger, check book, bank reconciliation sheets, and historical or pending documents in files.

The computer based analog to all of these functions (and many more for this particular application) requires many separate programs, where some of these programs work on most of the information (loosely referenced above) and other programs work on only a small isolated set of the information in files or in working processes.

Collection is the first level of things that do something. Collections can be compared to the definitions of programs and data tables (files) in current modern systems. However, the reason for the term collection is that the lines that box in programs and data tables can easily be bridged or amorphously divided into things that are smaller than the traditional concepts allow.

The columns of a table and the functions of a program are both collections. One represents data while the other represents process. However, the rolls can be reversed, for example a collection of data elements in memory. Collections are therefore that set of definitions which specify what is represented.

The synthesizer calls upon collections to provide the driving concepts behind a "program", where a normally hard-coded program would have these concepts embedded in the program code.

The collection can easily be changed adding new functions or creating new or more complex processing relationships. These fundamental changes to the collection can occur while the "program" is in use.

Allowing changes in the collection adds an amorphous nature to the program (and therefor to the Application and System) that empowers people to easily make changes or improvements. New capabilities can be molded from existing chunks of other programs, even if the programs are unrelated. In effect, any combination of program design can at any time be declared an object unto itself, even if other objects share some or all of the selected components.

New objects can be created by making global changes and then tacking the new object into a program as desired. For example, the vendor name and other demographic fields (including various bits of logic documentation and the like) can be declared in an accounts payable vendor maintenance program as an amorphous object. Such a declaration has no effect on the running application. The resultant amorphous object could then be reused to define something that is similar such as the name and address of an employee. The new use of the amorphous object can be altered and still be managed as the same as the source amorphous object.

The database references, intra-program or inter-program communications and connections do not have to be adjusted. The modified object can then be dropped into the design of the customer maintenance program without the need for design function. The Application Synthesizer's design tool will automatically attempt to line up correct connections with the new connections and database connections in the new program. For example, in most cases, the design tool will recognize that any field that belonged to the vendor table should now be connected to the customer table.

A librarian allows the user using the design tool to store copies of amorphous objects for consistent reuse. Efficiency is garnered by separating the sequencing information that makes a given subset of the node network work for a given run-time Virtual Program from the sequencing information that selects the subset of the node network from the database. A single request to the database manager can result in a single message that contains a family of Useorder entries.

For example, a single database request for the collection "VIRTUALPROGRAM" yields a superset containing the Useorder entries for execution order, all related databases, all of the fields in each of all of the related database tables, and a plethora of used building blocks anchored to the objects in the execution order Useorder Use collections are managed by their internal context which is the reference to the reason a process is needed. Use collections need not be referenced by the actual Useorder name which is called Useorder, or by the node network parent—child pairs, called Used Object and Parent Object Leaf or root nodes could be identified by empty values, The Useorder structure is a hybrid tree structure in which the columns "Parent" and "Useorder" define the parent-child relationships within the tree. Instance allows duplication of the child node number. Instance eliminates the need to process all of the children relating to a parent to find that group of children.

Useorder table defines organization and also establishes relationships between source and targets. The Useorder also establishes the organization of the relationships. In the preferred implementation, the first four columns define an arbitrary point in space which is assumed to reference a given part of a software application. The remaining columns describe the makeup and operation of that part of the software application.

The next column "Parent" in combination with the "Useorder" establish the hierarchy within which the application is defined. "Bundle" column adds the temporal quality to the definition which allows for timing in events. "Instance" allows for duplication of the key and establishes an order within the definition established by the key. "Useorder" defines action by name, for example disabling or positioning a button. The "Useorder position" then establishes the order within which the set of related objects can be processed as the synthetic program executes.

There are two classifications of parent Useorder entries in a version of the Useorder processor. The first classification is a parent Useorder with its parent set to "ROOT". The second classification is a parent that has a parent Useorder set to something other than ROOT.

Any Useorder can be started as if it were a parent. A Useorder entry that is started directly (instead of by another Useorder entry) is a parent Useorder. No difference exists in defining a Useorder code for a parent or a child Useorder. The "data" that defines a parent or a child Useorder is inferred by how the entry is started.

Useorder entries that have ROOT as parent are assumed to be the first node of a Useorder hierarchy. Any Useorder with a ROOT parent that does not have a command (i.e.: may start with !) in used or used related may attempt to load Useorder entries from an external Virtual Program collection. The Useorder processor uses the *used* object to see if Useorder entries that belong to a collection of the same name are currently in memory. If no such Useorder entries are currently in memory, a Useorder load is attempted.

The Useorder processor is supported by a Useorder re-sequencer which provides a dynamic way for the system to modify its orders. An external stimulus, for example, moving the location of an object on a display or changing the flow of a process, will cause the re-sequencer to start and re-align the Useorders.

Virtual Programs

Construction of a Virtual program declares that the Virtual Program exists. The existence of a given program within its universe is known by its relationship with the rest of a virtual environment. The program which interacts with the user is driven by one or more Collection of Structures, but is named as the combination of Virtual System, Virtual Application, Virtual Collection and Virtual Structure.

The virtual environment is the hierarchy from the Virtual System point of view. Virtual Programs are the same hierarchy from a single Virtual Structure point of view (in reality system+application+collection+structure).

Figure 40:
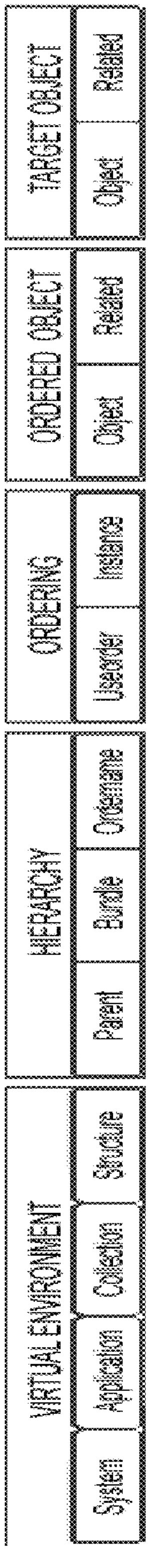
FIG. 40 shows a synthesizer system of one embodiment of the present invention.

Organization a specific virtual environment or existence is hierarchical starting first with Virtual System as the most general and last with the Virtual Structure as the most specific (see FIGS. 40 and 41). The level of specificity increases (more fine grained) as more of the existence fields are used.

Synthesizer

Referring to FIG. 40, the Synthesizer is an environment within which virtual concepts are collected to be solidified into conceptual programs. The conceptual programs represent capabilities that are permanently embedded inside computer software applications.

In the Synthesizer, the elemental capability is encapsulated within atoms and then made available via virtual representations. Atoms are the encapsulation of only the most elemental capabilities. Atoms are the distilled essence left when recognizable programmatic functions are boiled-down. The analog of programmatic Objects are created in real-time by the assembling atoms into various permutations of functions. The process continues building recursively, with each recursion producing more and more capable entities. Assembly iterations cease when the desired functionality has been achieved.

Desire Editing

In the preferred implementation, the Desire Editor creates a graphical environment for a user while designing a Virtual System. Designers can create or maintain the Widgets and functions associated with a given Virtual System, Application or Collection. The Desire editor enables a user to create or manage on two distinct conceptual levels. The first level is designing using Widgets and the second level is deigning with Useorder.

Widgets are the static components of systems which normally create structure of programs including but not limited to a field or button. Widgets act as the reference points for programmatic behavior. Program behavior also takes action upon widgets.

Virtual Collections are sets of building-block Widgets which are loaded into working memory to synthesize a running computer program on-the-fly. The most noticeable form is the Anchor Widget. The Anchor Widgets are "visible" on the open pasteboard when a Virtual Collection is edited. The anchor widget could be considered the "root" of a single Object in a running program. For example, a button that causes an event must be an Anchor widget while the supporting functions responsible for performing the function are not Anchor widgets.

Collections represent the potential of a program, not the actual program itself. In the virtual environment, there are no real programs. Representations of the program synthesize functionality during run-time. The Virtual Collection itself can also be thought of as a virtual widget to which other widgets and functions can be attached.

Virtual Structure Distinguishes the personality of the system being described to the Synthesizer. Structure is the anticipated computing behavior for the current Virtual program. Collections which share the same name, but have differing Structures are assumed to be related within the same Application, but perform different mechanical functions.

For example; a Database Table named "Customers" is the same conceptual level as a Virtual Program also called "Customers". Structure could also have been called application discipline because a given collection may be called upon to perform the equivalent functions as normal computer programs written by programmers trained in a variety of disciplines, such as communications, process control or tabular accounting. The Structure Identifies and separates the purpose of a given definition within a Collection.

Dragable Proxy is a standardized, encapsulated service for generating specialized events unique to each kind of list change. For example; adding or deleting an item on a list are different operations and generate different DragableProxie Events.

In normal use, more than one graphical proxy is in play. The first proxy is the one that shows when the Object is quiescent, that is, no activity from the user or from system generated motivations. Each of the items being proxied has at least one graphical Object to which it is assigned. No other item can share a quiescent graphical object. (The graphical object would not be visible unless the motive for the object being presented was something for it to represent).

Only one proxy is needed for all manipulation events within a given ordering editor or other listing container. This extra graphical object has special facilities to support interactive event-driven manipulation that can be directly translated to persistent data changes or system actions. Using a proxy to represent a collection of objects can save processing memory space and system processing overhead by allowing far less sophisticated graphical representation. Objects serve as a proxy when there is no need to support interactive manipulation.

The extra proxy, called the client proxy, is constantly kept current. Each time a new manipulation object gains mouse focus, known as a slot change, at least the display text of the proxies for which it may be used is replaced. The client proxy is maintained as invisible, but there are options to give it a visible border or make it opaque and always showing its text. The client proxy is the one that actually gets exported when a proxy is dragged from on context into another. The data to which the proxy is representing is then copied from the actual data source into the client proxy. The data has to be collected from the actual source because the original displayed proxy has little more than label text, dimension and screen position. The source data may be deleted if the process is part of a cut, copy and then paste operation. Please note that it is possible to not delete actual data at this time. The user may wait for confirmation that the data has moved to its new location. A brand new DragableProxie is then created to replace the one that was exported.

User Interface for Editing Orders

Ordered lists need a vehicle that enables a user to make changes that then become translated into changes in the underlying dataset. Any one of the graphical vehicles available for manipulating order can be used to represent an order being edited. For example a list of names where any name can be dragged to another position is suitable for a user interface.

Tools used to make modifications to a listed set of data elements need to be imbued with a high degree of malleability and need to appear to react in real time. Users can interactively define how a system will work. The amount of creativity applied to the design of a system is directly related to the effort it takes to implement that creative output. Therefore, a user interface has to help accelerate the effect of design changes. Being able to declare any set of objects as an object that can be manipulated, allows global "search and replace" design functionality such as assuming that all of the objects in a vendor definition are declared to be an amorphous object. Any manipulation of that amorphous object could have an effect on any or all of the objects within. Using an object in the context of a customer that currently defines vendor information would cause the appropriate changes in wording and screen location (should the objects be fields on a screen).

Human behavior is less linear than a one at a time model allows, forcing the user to keep track of previous and future changes. It would be preferred to allow the user to spread all of the pieces out on top of a table and then manipulate various bits in random order, Datasets represent a complete real-world "picture" of something. Graphical objects represent the datasets. The real-world something can only on the rarest of occasions be conceived or understood as a line with evenly spaced points. If our something could be represented in this kind of linear fashion then it would become possible to add creative works only by adding one thing at a time, but only having to think about one finite point at a time.

People deal with information as a whole attempting to develop a mental picture from the data. Therefore in most cases, an element of data is meaningless unless it is related to other data elements. Creative efforts also have to start with the abstract and then fill in the details.

The point Free Range is an environment that empowers by giving the user a place to put objects while disconnecting relationships between that object and other objects. These objects can come from different and even, incompatible places and left to roam free when the user manipulates various organizational representations. Objects in the free range are temporarily suspended. At any random point in time, the user can capture an object and insert the object into an organization. The simple act of insertion implies a variety of relationships which instantly form. For example, the object is now related to whatever the list into which it was inserted represents. The inserted object becomes related to other concepts in lists that have some form of relationship with the list. The ordered relationship also exists between the inserted object and the object now before it and then one after it in the organization of the list. The order itself could also be considered another relationship separate and apart from the relationships to the object before and after.

The conclusion is that any part of a represented concept that exists within the same "construct" (i.e. application screen) can be manipulated while any other part of the same construct is also in an incomplete state of manipulation. The Free Range is a freeform, multiple object manipulation environment. Where the user can start the action of manipulation of any part of a given design construct, and then start another and so on.

In some cases design may be best served by dissecting objects temporary suspended and then reusing components. The user can then place the objects that are laying about in a disconnected meta state either back into the same context or into a previously unrelated one. The design is malleable. The mechanisms in this system that mold and sculpt a system into being are also highly malleable.

Real-time requirement: Actual database changes do not have to be in real time. However, the user interface must behave as if those changes have been committed. For example, if a user directs the system to change the color of a button, the visible representation of that button must change. The requested changes must stay in sync with the actual work. Real-time takes on another meaning when collaborative work efforts are added. Changes made by user A need to instantly become represented to user B. The actual data represented by these changes must be changed in an orderly and controlled manor.

Changes must be reversible and audible. Such changes create a meta state in which agreed upon changes are represented to more than one user. The changes must be described in a transactional audit before or as committed to the database. The meta state becomes clear when users interact with the same data that cannot be exposed to the changes in the database. For example, various people around the globe are collaboratively improving a given data collection screen. At the same time, users are using the data collection screen. All of the collaborative developers must have all of the changes (the user's changes and other's changes) incorporated so that other changes made which rely on the earlier changes will make sense and work. Changed versions can be run at the same time and in the same environment as other running versions or the currently deployed application. The regular user cannot be interrupted or exposed to change. In the case of software system design, multiple versions of the same software would normally coexist but kept separate. The same issue is present in an environment with no application software. The analog of the replaced software is data in a database.

Proactive Network Traffic Optimization

Dynamic network buffering which can be optimized to significantly reduce the amount of data moving across a local or wide area network.

The effect allows systems running over the Internet to have performance characteristics close to those of systems running on a controlled high speed local area network. Event relays, a class, have a set of complementary network "Relay" Events intended to provide a way to move an Event signal down the network in client—server, three tier, and n tier topographies. For example, assume a set of Ordering Editors need the next page of data from the server side database manager's universe of a given data set. The editor process signals both the request for the next page of data and the request to relay that request in this single Event. Of all of the listing processes, the process that will accept this Event and then trigger a new Event is a first process that is listening for our example editor that has the ability to service the relay request and has the proper network visibility.

Network Events are generated to allow the system to move less information at a time and still fill all of the system requirements. The network events limit the data sets transmitted over the network. For example, assume a user is interested in items near item number 300 of a listing of 1000 items and that the display only allows the user to see 20 items at a time. Normally either all 1000 items get shipped or the server hands out smaller batches starting with the first item allowing the first set to display and then continue loading the rest as a background task.

Network Buffering

The Synthesizer's network buffering scheme allows for the transmission to start at 300 (or just before) and then stop moving data over the network when a specific number of items have been sent. The number of items sent in one of these batches can be dynamically set, but for the purpose of this explanation, assume that the page size is 100 items. The very first item transferred over the network (in our example) has a relative position in the universe of the source data set of 300. The same item has a relative index of 1 of the in memory page array. In our example, only 10% of the data items have been transferred that would have otherwise been transferred.

The Synthesizer's buffering schema takes into account that the GUI display itself is yet another data subset. In our example the GUI has items 1 to 20 (20 items display at once). The index into the GUI is referred to as a "slot" number which makes reference to the rectangular screen area used to represent the data item. Without examining the buffering on the server side, a three tier hierarchy of buffering that is intended to minimize all required system and network resources to maximize the perceived performance of the system to the user has been described. The GUI does not require its own copy of the 100 items or the original 1000 items. The GUI only needs enough to fill the display area. This reduces the amount of memory required in the client machine's windowing memory, which also reduces the risk of memory related problems.

Getting More Data from Memory

The client side processor replaces the small page in windowing memory as the user scrolls the mouse wheel or slides the slider bar to move the displayed list. As the list approaches a page boundary (the end of the data subset now in the client machine's working memory) a system Event is triggered that drives a request for another page from the server. If the page is already loaded the Event is ignored. The data from previous pages for the same data set are retained allowing the in memory subset to grow towards the population of the original source data set. Additional buffering of the same kind can be managed on the server side and from the link to the database manager. When properly forecasted, the user should notice no delays while reviewing data supplied from the server and should notice a marked improvement in the speed in which data becomes available when first requested.

Advanced Forecasting

Each application and user has characteristic behavioral patterns. These patterns can be harnessed to predict the chances that the user will soon need a resource that is not currently available or in memory. For example, some people like to scroll through lists to the ends reviewing and then re-reviewing the listed contents, while others like to quickly get to a spot make a selection and then move on.

Characteristics can also be garnered relating to individual implemented controls in specific screens of specific applications. For example, a listing of the countries of the world will more times than not be directed to a specific group of alphabetized country names. After a user has made a selection, the probability of that user returning the country list to change the selection (same session and same screen) is calculably small.

There are still other characteristics that should be tracked as driving information for a given forecasting model. One of the more unique characteristics is generated by the forecasting system itself. That is, some people and some applications are simply more predictable then other people and other applications. Therefore, the propensity for a given person and or environment to refine the system's understanding of that person or environment is in itself a forecasting tool. The more often the characteristics change (weighted for volume of actions) the less predictable. The system's reaction would be to expand page size and/or widen event bounties until the number of refinements drops within acceptable norms. Acceptable norms are also generated by the system by extracting simple weighted averages from the database generated by people and environments. A proper forecasting model would take into account the combined effect of environmentally driven behaviors, like the country list and the individual propensities, like a common desire to scroll around in lists and the generated characteristics and propensities from the forecasting system.

Bi-Directional Events

For clarity describing the technology, events that are initiated by any action that can directly be attributed to a user are called Events. Those Events that flow in the opposite direction and therefore are only indirectly triggered by user actions are called "broadcasts".

Broadcast Events work much the same way as traditional Events and are built to match the Java language standard as closely as possible.

The customary methods to fire the Event and remove the listener are named as follows: instead of fireMethodName it becomes broadcastMethodName. In place of a simple add (listener) and remove(listener) methods there are add(DragableProxie), add(UseorderEditor), remove(DragableProxie) and remove(UseorderEditor).

Implementing in Software

Chain of events . . . There are a number of Events in the Synthesizer system. Each of the events is designed to narrow the scope of Events that are already a part of the GUI windowing system. The theory being that using an "interrupt" in the form of an Event will give objects a chance to react to narrowly defined systemic events. For example, assume that 17 GUI components are populating an Open Free Range wherein the components can be manipulated. One of those objects is dragged until it intersects another component at random. In this example, all of the objects within the Open Free Range are informed of an event where one of the objects encounters another. The actual Event carries enough information for each of the Objects to determine on their own if there is something they need to do to react. Continuing with our example, the user may want a selected set of the objects to change color as one of these objects, selected at random, has its color changed. From this simple example, you can see how dynamic the user's experience can become.

To make all of this work, the present invention enables Events to tag other events which can tag other events. At each point where one event triggers the next is logic that limits which of the events to which a particular listener will pass along to the next. At these decision points, more than one Event can be triggered. In other cases, the conditions interpreted by the logic at the point of listening will choose from a list of potential Events to trigger. For example, when an object intersects another object and neither of them are inside the other (just overlapping), the Synthesizer system triggers Events for each of the types of objects involved in the intersection. This is a case where one event triggers more than one Event to be relayed. When the same object is moved away from the object into which it intersected, a different set of Events are triggered to tell the objects to abandon any current potential for insertion.

It is the same chain of events that triggers the encounter Events as triggers the abandon Events. The Difference is that each of the listing points evaluates if the objects intersected or separated. Some of the chains are documented here. This is not an exhaustive examination of the chain of events. The following assumes that there are more than one DragableProxie Object and more than one UseorderEditor Object currently within the Open Free Range The following is the processes documented step by step showing how it works in code—we can remove it if it is too detailed Drag a proxy or proxies from listing editor to Open Free Range chain of events MousePressed Event from a DragableProxie Object mousePressed( ) gets the Event—sets item in play flag and a reference copy of the Event source is madeMouse starts to move to drag the proxies, mouseDragged( ) gets the Event—stores a copy of the source Object's bounds if first time sets up drag, triggers dragableProxieDragStartEvent( ) Here starts two analogous chains of Events. The first one for the Order Editors currently registered with this Free Range. The other is for the Free Roaming Proxies. checks boundary state for slots and whole editor if slot state change, triggers dragableProxieSlotChangeEvent, if dragged Object is partially outside of the editor, trigger dragableProxieOffEdgeEvent, if state of being in the editor changes, if Object was dragged in then trigger dragableProxiePayloadExportEvent, if Object was dragged out of the editor trigger dragableProxiePayloadImportEvent triggers dragableProxieEvent for location Following drag start Event, the UseorderEditor sets an in drag flag up then triggers UseorderPossibleExportEvent Following possible export Event—we switch to FreeRange. creates visible representation of the drag proxies so that the part of the proxies hanging off of the editor edge is still visible. Now we have a proxies being dragged and is now hanging partly in the source editor and partly in this Open Free Range. Follow the chain as the user continues to drag the proxies out of the editor. Following off edge Event from above . . . evaluates the source action, if proxies has left the editor, capture proxy's parent editor name, if this was only a re-ordering within the same list, trigger UseorderOrderEvent, if proxies is dragged back into the editor, fireUseorderPossibleExportCancelEvent, repair display listing. Now we return our attention to the DragableProxie which triggered the off edge Event and now triggers payload export Event.

DragableProxie Object triggers dragableProxiePayloadExportEvent. Order Editor hears the Event and we switch to UseorderEditor dragableProxiePayloadExportEvent( ) in UseorderEditor: seals the DragableProxie Object, set the source editor's title in the proxies release the current in memory copy of the proxies delete the removed editor item trigger UseorderExportEvent create a new DragableProxie Object for this editor's next manipulation event, send panel screen area to exiting proxies, repair the listed display Following the UseorderExportEvent, trigger freeRangeEvent, install proxies extracted from the incoming UseorderExportEvent into the Open Free Range. Here the chain of Events reverses directions to tell the sources of the Events about post event conditions. Instead of triggering an Event, the interrupt is provided via a broadcast which is the inverse of an Event.

UseorderExportEvent then triggers //broadcastDragableProxieNewFreeRoamerEvent, if data was deleted then trigger freeRangeDataDeleteEvent if generic data events are set to trigger then trigger freeRangeDataEvent. From here we will choose to follow user action concluding the drag operation. This chain started with a user starting a drag operation on a DragableProxie Object. Now, discussing the same Object still being dragged, User releases the mouse button and processing returns to the DragableProxie Object. trigger dragableProxieDragEndedEvent, reset font and graphical sizes, reset border and terminate drag mode Dragging proxies from the Open Free Range into one of the order editors which share the same range again starts with the same chain of Events. A mousePressed Event triggers the same initialization and then the beginning of movement follows also with the same chain.

DragableProxie Events are generated as the proxies move within the Free Range. This chain turns onto a very different path when the proxies intersect one of the editors. The intersection starts two chains, one chain for proxies and the other chain for editors. The Event triggered by the proxies is intended to be heard by editors. The Events triggered by editors are for the proxies. Proxies send encounter events which tells any editor that is experiencing an intersection with the source proxies to evaluate the possibility of accepting an insert of those proxies.

From the other direction the editor sends an "is interested" Event. If an editor shows interest in a proxy, the editor then sets the proxy's "under contract" flag on a first come first served basis. The editor gets an "is interested" flag set. Such a configuration allows any mixture of many to many relationships between proxies and editors. For example, a group of proxies being dragged all need to be placed under contract when any one of those proxies encounters an editor. Likewise, all of the proxies have to be evaluated by the editor to see if it will allow each one of them to be imported.

Options.

Open Free Ranges: The following includes the options as defined in the initial version of this system:

isDuplicateProxiesAllowed
isFreeRangeManagingGraphics
isGeneratingTranslatedEvents
isGeneratingGenericDataEvents
isDuplicateProxiesAllowed (Are proxies containing the exact same datasets allowed to be Open Free Rangers at the same time?)
isFreeRangeManagingGraphics (Has the host class provided its graphical context on which new Free Rangers are to be visually added?)
IsGeneratingTranslatedEvents (Should Order Editor compound actions be translated into their multiple constituent Events?)
isGeneratingGenericDataEvents (Should this Open Free Range generate a data Event each time any data Event is triggered?)

Finding Source FreeRange.

Both FreeRangeEvents and the FreeRange Object carry the class type and Instigator assigned index needed to identify a given Open Free Range. getParentClassType( ) returns freeRangeOwnerType, which is the known type of class to be used as a consistent reference point. getParentIndex( ) returns freeRangeOwnerIndex, which is the numeric ID assigned by Instigator for a given type of Widget Object.

The same methods exist for FreeRange Events and the FreeRange Object itself. These values can be used in the Instigator to point directly to the anchor object to which the source FreeRange is attached.

Another way to implement: two values will be needed to find a given Open Free Range. The first is returned by getParentClassType( ) which is a string value matching the type of widget to which a given FreeRange object is anchored. The second value is the sequentially assigned index of the anchor widget as it was originally assigned by the current session's Instigator. Both of these values are constantly available in working memory while the Instigator is running. The values point to the anchor Object and not to this Open Free Range. Both values are also available in this FreeRange Object. The facility provided by equals(freeRangeParentClassType, freeRangeParentIndex) method allows you to scan all of the current FreeRange Objects and compare both values, listed above, to find the one that matches.

In addition the FreeRange class of Events has various pointing values encapsulated within. Another option includes extracting the Open Free Range's ID from a FreeRange Event via the getFreeRangeID( ) method.

Direct Order Manipulation

A single class is the only mechanic needed from which a user can manage the order table. Orders are normally managed automatically by the system. This Order User Interface enables a user (in this case "user" is a member of the Synthesizer lab) to add, remove, review and reorganize order list entries.

A single order entry can represent a method in real code or other use entries. Entries can carry data, but the data is never user level. For example, a value can be compared to a value collected from the user.

Order list entries are presented as iconic representations listed in the same order with the same number of order list entries.

Order editors are visual containers that allow the user to manipulate graphical proxies as an input method that the system then translates into actual computing processes.

Order editors can be selection tools providing the same functionality as a GUI list box. The editors can also be tools that allow for the random and instantaneous reorganization of the items within. Editors can also be used as a source or target GUI Object empowering the user with an easy to learn and intuitive mechanism to define complete data structures.

Like any such tool the building blocks are that of data insertion, copy and deletion. Order editors can represent organization of data and can contain the data as well.

Order editors can be used in ways that are not instantly obvious such as a GUI trash can or clip board. Order editors generate interrupts in the form of events that support most modern topographies, including those of the web. Changes to persistent storage can dynamically switch from one style of topography to another. For example, In an n tier architecture that includes wide area networking, one might prefer that a database system is presented with transactions as close to real-time as logistically possible. When the network bottlenecks at random junctions, the application software might not be able to become re-optimized.

Order editors (order as in organization) can produce events to tell the system when processes should take place assuming the optimization discussed earlier.

The difference is that editor is still able to produce events to support a plethora of other optimizations, including fully buffering with the end client system. Therefore, the user's computer can be accommodated with little to no visible downturn in perceptive performance. The properties of an n tier topography carry inside the user's computer. For example, if 1 million records are present in the database are narrowed down to a set of 25,000, the data is at one end of the network and at the other end of the network is a display. The display only has 20 items visible at a time when scrolled.

Any subset of the data can be shipped to the client as long (in this case) as it is greater than 20 elements but 1000 could have been delivered. Now inside the client machine the GUI environment does not need to be managing that many elements. Certainly, the user does not want to wait for the whole set to load into a list box. The order editor only loads as many records into the GUI buffer as need be displayed, allowing lists to start very fast. The rest are loaded into a buffer that mimics persistent storage. The order editor is told how much data exists in this universe of this data set and the amount of data in working memory.

Data is then presented to the GUI interactively—producing the same kind of speeds traditional list boxes can demonstrate. However, the Order Editor knows when the data subset in the buffer is near the end and can generate events to request additional subsets. This gives a single list control the speed and power of multitasking. Ordered lists need a vehicle that enables a user to make changes that are translated into changes in the underlying dataset. Datasets exist within the confines of a database management system which also act to serve that data.

Database management software can be installed on one machine while the software that operates upon that stored data could exist on another. The user may be interacting with yet another machine.

Steps: A Graphical User Interface (GUI) instantiates one or more OrderUI objects and passes in the following values.

Inputs to an instantiated OrderUI object:

1. Order name Order list population: Each object is supplied with the name of a specific ordering list. The list that the name represents may or may not exist. The name of the list passed identifies which order will be affected.

2. Order list population: The list is expected to be constructed as a standard array, with the node count in node zero. The supplied list contains all of the fields found in each record (row) of the order table in a multidimensional array. Input to this class is initiated by the appearance of an icon whose name can be found in the list provided by the calling class from which this class was instantiated.

The editor creates a complete collection of proxies when proxies represent themselves. Each potential item is preconstructed and only displayed when appropriate. Any manipulation is on the GUI component exposed by the proxy. In contrast, proxies are manufactured as needed for manipulation and export when representation is provided by the editor in the form of a manipulatable button or label.

Order Manager Facilities

Each of the calls for supporting services into the Use Order Editor has been designed to require as little new information as possible. To simplify implementation, systems built with this class can become much more dynamic. The tradeoff required to make the calls so simple is that the first call made to this class after it is instantiated must pass enough information to enable an in-memory database owned by the instantiated object created with this class.

The order of events is: 1) Instantiate UseorderEditor, 2) Call the Order Manager's "getEditor( )", 3) Then make calls to modify the displayed list, 4) The First call "getEditor( )" does not, by itself, cause anything to happen on the display. Instead, it returns a fully populated JLayeredPane object that has the display populated with the supplied items with all the requisite listeners installed. You have to place the returned JLayeredPane in a compatible display container (that is compatible with a javax.swing.JLayeredPane) and add any listeners that you need for your program to process.

However, the calls to supporting services automatically update the display. It is possible for a Use Order list to become so voluminous that the sheer volume either risks memory or unacceptably slows network performance. This class has a special kind of event that, when listened for, requests more entries in a given Use Order. The concept is that the program which this class is implemented becomes a server that transfers requests and results for more items. Network performance is greatly enhanced due to the savings of data transfers relating to items that are not currently displayed in a given editor (this class).

Multi-Tier Data Architecture

All of the existing Use Orders are stored in a database, including the items in a given list. The server side makes a database request for a subset of the database which is to contain all of the items of a given Use Order list. A definable subset of these items is transferred to the client and is stored in an in memory "page" array. A still smaller subset is displayed. The displayed items are the only ones actually populating the GUI control. The rest of the items are paged from the in memory page array as needed. The result is that a large number of items being downloaded to the client will not slow the initial display of those items. Likewise, the balance that has not been displayed of the downloaded items continues in the background while the user has already been granted full access to the GUI control. When the display needs a different set of items, it makes a new request of the in memory page array in much the same way systems make requests for subsets of data from a database manager. The process is quite fast because only the client computer has to do any work and all of the data being manipulated is in memory so new subsets are brought to display fast enough to make it seem as if all of the data was already on a traditional GUI control. The same process extends across the Internet.

An event is generated when the user scans the control to the end of the in memory page. While the user is viewing the newly displayed items, the system reacts to the event. This class only issues the event if the event does not manage the processes required to start once the event has been generated. For example, most of the items needed for a given list are not transferred from the server over the Internet to the client that is in the process of editing that list. Enough items would have been transferred to enable the user to see the localized effects of the items that are available and the smaller subset that is currently being displayed. The user then adds, deletes or modifies the local order. Items being reordered are expected to be repositioned near the spot on which they started. The change request travels back through the system to the server which then requests the modification to the database. In this example, the items that did not load with the first page, never load. The entire network overhead that would have been consumed is saved, helping to assure reasonable system performance.

Tracking Change in System Design

The change recorder is responsible for the baseline Widget and orders as well as detail of any changes since the baseline. The keystroke or other form of detail of each and every change to the work is collected in real-time. The changes are therefore always in synchronization with the combination of the baseline and the current operating model. The detail can then be saved to persistent storage as version history control or be used as a program to dynamically move the version of the work either backwards or forwards at any increment of change. In other words "version" becomes a signpost marking a point in a change stream, where the last version is the application of all of the detail changes up to that point and the next version is the application of all changes up to the next version mark. In a Synthesized system, the whole of the system can be moved back through development time and then forward again stopping to exercise the system at any graduation in between. For example, a user may need to prove that a system could not have generated a specific data anomaly at a point in time, the existing system could be copied to another computer and then have the request number of changes reversed to make the system in the exact condition it was at that time in history.

More importantly, the finely grained nature of this kind of detail change history allows the development and implemented versions of a designed system to operate on the exact same computer as the exact same copy. Problems relating to human recording of versions or implementations are eliminated because there is always only one copy. For example; a potential change to the work can be made in a collaborative environment or standalone without affecting the version that is now implemented. This is especially true in software where changes are a normal part of a products life. Should the change prove to be of benefit, the change could then be implemented by simply telling the system that it is implemented. There is no need for any copying, installing or implementation processes. The new version is simply instantly in-place.

Assume that normal change recording could be likened to a camera where the first picture becomes the baseline and successive picture become a record of changes. To extend the analogy, Integrated change history and version control could be likened to video tape where each and every change is captured in detail with each frame being a point in time. Where the analogy fails is in the area of being able to reverse and re-apply changes. This would be like a backwards video camera where any frame could be randomly selected and the physical world would revert to the exact conditions present at that point in time. Obviously this cannot take place in the real world, but it can take place in a virtual world. For example; Objects, documents, software or designs could be moved dynamically through time and the computer can then synthesize the same computing environment it did when it first encountered the same conditions.

Steps

Referring to FIG. 41, the recorder stores a copy of each successive Softbus supplied, but only when there is a difference between the last stored copy and the presented copy. The system global change count is communicated via the Instigator and is greater than 0 when the snapshot request was external to a widget which has this process instantiated. The global change count is 0 when the class that initiates the snapshot request is the same as the class that instantiated this recorder class. Normally this class is intended to be instantiated by a widget, but there may come a reason to have another kind of class use the camera.

Figure 42:
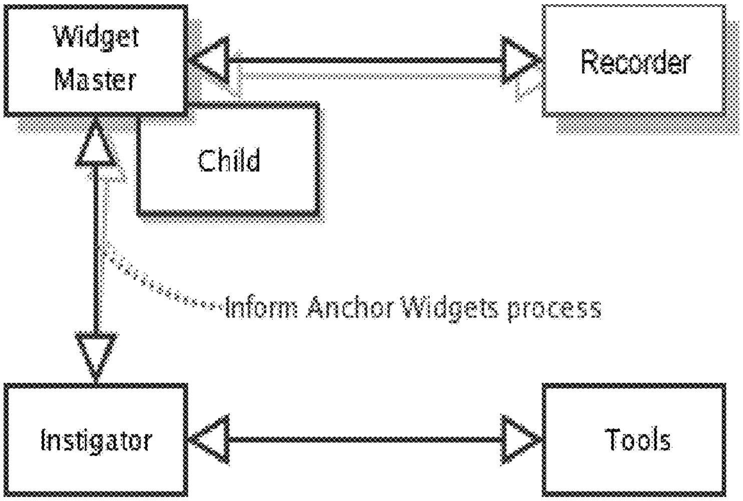
FIG. 42 shows an editing session enabling the modification of a system design in collaboration with at least one or more users of one embodiment of the present invention.

Each instantiated has its own change recorder and records all of its own changes. Therefore, the complete list of all changes for a given desire editing session is the sum of all of the individual lists from each of the anchor widgets. See FIG. 42. A complete list is called a registry, due to the fact that it is not the actual list, but just a copy that also contains address information needed to find the actual list in the source anchor widget. The process of creating a complete central list makes use of the informAnchorWidgets( ) method in the Instigator. The Instigator has a single copy of WidgetEditTimeTools( ) instantiated, which serves as both a repository for session events, and a library of tools from which the lists in the repository can be processed. A class file creates a reference variable using a class similar to: protected client.synthesizerEnvironment.WidgetChangeRecorder historyCamera;

Instantiate once when needed, for example have a method that may or may not be run: for example; private void createHistoryCamera( ) {historyCamera=new WidgetChangeRecorder}. The next step is to establish the baseline for the session history. Note: the zero value indicates that this snapshot should not have a system key and therefore is locally initiated. For example; requestWidgetTakeBusSnapShot(0, softbus); The first time a snapshot is taken creates the baseline change entry. this line will also create the baseline, if it is the first time a snapshot is taken: requestWidgetTakeBusSnapShot(2301, softbus); When it is specified (non-zero) it is added to the stored change as a key allowing easy discrimination between changes from different widgets stored in multiple locations.

From the foregoing, it will be seen that the present invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A method for accessing and processing medical record data of at least one patient using a computing device, the method comprising:

- the computing device accessing an authority chain as a result of a user ordering a directive requesting a specific action for the patient wherein the authority chain is stored in a table;
- the authority chain defining a task to be performed;
- a chain identifier associated with the authority chain that identifies the authority chain;
- at least one chain step associated with the authority chain, the chain step identifying a task to be performed and at least one user to perform the task;
- a function call associated with the chain step, the function call identifying a computer function to be performed by the computing device;
- a chain step number identified in the table wherein the table associates the chain step number and the chain identifier with the chain step, the chain step number identifying the sequence in which the computing device performs the chain steps of the authority chain and the function calls of the chain steps identified in the table;
- a current chain identifier that identifies the authority chain to be currently performed by the computing device;
- a current step identifier that identifies the chain step number to be currently performed by the computing device, the computing device initially setting the current step identifier as the chain step number associated with the first chain step of the authority chain when the authority chain is initially started;
- the computing device accessing the chain step associated with both the current chain identifier and the current step identifier stored within the table ("the processed step");
- the computing device performing the function call identified by the processed step;
- the computing device incrementing the current step identifier to progress within the table to the next chain step and the next function call associated with the next chain step stored in the table; and
- the computing device performing the next function call identified within the table by the next chain step after the computing device performs the function call identified by the processed step.

2. The method of claim 1 wherein the chain step identifies the user to perform the task by identifying a department of the first facility associated with at least one user, the computing device forwarding the task identified by the processed step to the department of the first facility for performance of the task by a user associated with the department of the first facility.

3. The method of claim 1 wherein the chain step identifies a specific user to perform the task, the computing device forwarding the task identified by the processed step to the specific user for performance of the task by the specific user.

4. The method of claim 1 wherein the chain step identifies a specific type of user to perform the task, the computing device forwarding the task identified by the processed step to the specific type of user for performance of the task by the specific type of user.

5. The method of claim 4 wherein the type of user includes doctors.

6. The method of claim 4 wherein the type of user includes nurses.

7. The method of claim 4 wherein the type of user includes doctors identified by specialization, the computing device forwarding the task identified by the chain step to a doctor of the identified specialization for performance of the task by at least one of the doctors of the identified specialization.

8. The method of claim 1 further comprising:

a start authority chain identifier associated with the chain step, the start authority chain identifier identifying a second authority chain to initiate during the chain step;

at least one chain step associated with the second authority chain, the chain step of the second authority chain identifying a task to be performed and at least one user to perform the task;

a function call associated with the chain step associated with the second authority chain, the function call associated with the second authority chain identifying a computer function to be performed by the computing device;

a chain step number associated with the chain step of the second authority chain, the chain step number identifying the sequence in which the computing device performs the chain steps of the second authority chain and the function calls of the chain steps;

the computing device setting the current chain identifier to the second authority chain after the computing device initiates the second authority chain;

the computing device setting the current step identifier to the first chain step of the second authority chain when the second authority chain is initially started;

the computing device accessing the chain step associated with both the current chain identifier and the current step identifier ("the processed step"), the computing device performing the function call identified by the processed step;

the computing device incrementing the current step identifier to progress to the next chain step and the next function call associated with the next chain step; and the computing device performing the next function call identified by the next chain step after the computing device performs the function call identified by the processed step.

9. The method of claim 1 further comprising:

the computing device accepting a user input to add an additional chain step within the authority chain;

the computing device associating a chain step number with the additional chain step to identify the position of the additional chain step within the sequence of the authority chain;

the computing device associating a function call with the additional chain step wherein the computing device will perform the function call of the additional chain step as the computing device processes the additional chain step.

10. The method of claim 9 further comprising:

the computing device querying a database of a second facility to retrieve a medical record associated with a first patient, the medical record including at least one field that provides information about the first patient;

the computing device accessing the at least one field;

the computing device converting the information in the field to text;

the computing device translating the text to conform to a system defined standard; and the computing device storing the text in a second database as a second medical record associated with the first patient.

11. The method of claim 1 wherein an application running on a wireless device receives the notification message, the application displaying the notification message alerting that the next chain step is available for processing; and the wireless device connecting to a remote data source to receive information collected throughout the chain.

12. A method for accessing and processing medical record data using a computing device, the method comprising:

the computing device accessing a first patient's medical records;

a viewing order stored in a table accessible by the computing device, the viewing order establishing the order in which the first patient's medical records will be displayed, the viewing order associated with a user and a data set of patient medical records;

a facility identifier associated with the viewing order wherein the facility identifier identifies a facility for which the viewing order will be displayed;

a first view sequence step identified in the table that defines the viewing order for displaying a data set of patient medical records, the first view sequence step identifying data to be displayed during the first view sequence step;

a second view sequence step identified in the table that defines the viewing order for displaying a data set of patient medical records, the second view sequence step identifying data to be displayed during the second view sequence step;

a step identifier that identifies the view sequence step to be displayed by the computing device;

the computing device accessing the viewing order and the view sequence step identified by the step identifier;

the computing device displaying the data identified by the view sequence step identified by the step identifier found within the table;

the computing device accepting input identifying whether the computing device should proceed to a next view sequence step or return to a previous sequence step identified in the table;

the computing device incrementing the step identifier if the computing device should proceed to the next view sequence step identified within the table; and the computing device decrementing the step identifier if the computing device should return to the previous sequence step identified within the table.

13. The method of claim 12 further comprising:

a first viewing order associated with a first user;

a second viewing order associated with a second user wherein the second viewing order varies from the first viewing order;

a first user identification assigned to the first user wherein the first viewing order is assigned to the first user identification; and a second user identification assigned to the second user wherein the second viewing order is assigned to the second user identification.

14. The method of claim 13 wherein the viewing order is associated with a user, the user customizing the viewing order according to the user's preferences by modifying the viewing sequence step of the viewing order.

15. The method of claim 14 wherein the computing device displays the medical records associated with the viewing order;

the computing device displaying the medical records for which the user has been authorized to view.

16. The method of claim 14 wherein the user accesses a medical record associated with a second patient;

the computing device accessing a second patient's medical records;

the computing device displaying the second patient's medical records according to the viewing order.

17. The method of claim 12 further comprising:

a next field selection wherein the next field selection causes the computing device to display a next data set identified according to the view sequence steps in the order established by the viewing order.

18. The method of claim 17 further comprising:

a next patient selection wherein the next patient selection causes the computing device to display the data set identified in the first view sequence step of a next patient's medical records.

19. A method to be performed by a computing device to access and to process data associated with a first patient, the method comprising:

the computing device accessing an authority chain as a result of a user ordering a directive requesting a specific action for the first patient wherein the authority chain is stored in a table;

at least one chain step associated with the authority chain, the chain step identifying a task to be performed and at least one user to perform the task;

a function call associated with at least one chain step, the function call defining a function to be performed by the computing device;

a chain step identifier identified in the table, the table associating the chain step identifier with the chain step, the chain step identifier identifying the sequence in which the chain steps and the function calls of the authority chain will be performed;

the computing device accessing the authority chain and the chain step identifier, the computing device accessing the chain step identifier within the table to determine the order in which to process the chain steps and the function calls of the authority chain;

the computing device processing the chain steps of the authority chain according to the chain step identifier found within the table;

the computing device performing the function defined by the function call of the chain steps found in the table while progressing through the chain steps of the authority chain found in the table wherein at least one of the function calls displays data to the user.

20. The method of claim 19 further comprising:

a chain step number associated with each chain step, the chain step number identifying the sequence in which the computing device performs the chain steps of the authority chain and the function calls of the chain steps;

a current step identifier that identifies the chain step number to be currently performed by the computing device, the computing device initially setting the current step identifier as the chain step number of the first chain step of the authority chain when the authority chain is initially started;

the computing device accessing the chain step associated with the current step identifier ("the processed step"), the computing device performing the function call identified by the processed step;

the computing device incrementing the current step identifier to progress to a next chain step and the function call associated with the next chain step; and the computing device performing the next function call identified by the next chain step after the computing device performs the function call identified by the processed step if the next chain step exists; and the computing device ceasing to process the authority chain if the next chain step does not exist.

* * * * *